US012673176B2

(12) United States Patent (10) Patent No.: US 12,673,176 B2
Dantanarayana (45) Date of Patent: Jul. 7, 2026

(54) DUAL CHAMBER PATIENT INTERFACE WITH AIRFLOW REGULATION

(71) Applicant: RESMED PTY LTD, Bella Vista (AU)

(72) Inventor: Muditha Pradeep Dantanarayana, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1077 days.

(21) Appl. No.: 17/639,228

(22) PCT Filed: Aug. 28, 2020

(86) PCT No.: PCT/AU2020/050903
§ 371 (c)(1),
(2) Date: Feb. 28, 2022

(87) PCT Pub. No.: WO2021/035306
PCT Pub. Date: Mar. 4, 2021

(65) Prior Publication Data
US 2022/0409839 A1 Dec. 29, 2022

(30) Foreign Application Priority Data
Aug. 31, 2019 (AU) ................................ 2019903204

(51) Int. Cl.
*A61M 16/06* (2006.01)
*A61M 16/00* (2006.01)
(Continued)

(52) U.S. Cl.
CPC .... *A61M 16/0622* (2014.02); *A61M 16/0003* (2014.02); *A61M 16/0666* (2013.01); *A61M 16/0875* (2013.01); *A61M 16/201* (2014.02)

(58) Field of Classification Search
CPC .......... A61M 16/0622; A61M 16/0003; A61M 16/0666; A61M 16/0875; A61M 16/201;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

CN 207666957 U 7/2018
CN 207694052 U 8/2018
(Continued)

OTHER PUBLICATIONS

"*Respiratory Physiology*", by John B. West, Lippincott Williams & Wilkins, 9th edition published 2012 (8 pages).
(Continued)

*Primary Examiner* — Elliot S Ruddie
(74) *Attorney, Agent, or Firm* — Nixon & Vanderhye P.C.

(57) ABSTRACT

A patient interface may include a dual chamber cushion assembly having a nasal chamber and an oral chamber. The nasal chamber may be arranged to deliver pressurized breathable gas to a patient's nasal passages, and the oral chamber may be arranged to deliver pressurized breathable gas to the patient's oral passages. The nasal chamber may be pressurized to a different level than an oral chamber to promote nasal breathing. An air passage may fluidly connect the nasal chamber and the oral chamber so that pressurized breathable gas may flow from the nasal chamber to the oral chamber.

26 Claims, 56 Drawing Sheets

(51) Int. Cl.
    *A61M 16/08*       (2006.01)
    *A61M 16/20*       (2006.01)

(58) Field of Classification Search
    CPC .............. A61M 16/20; A61M 16/0066; A61M
               16/024; A61M 16/0605; A61M 16/0683;
               A61M 16/0816; A61M 16/16; A61M
               16/161; A61M 16/208; A61M 2016/0027;
               A61M 2016/0033; A61M 2202/0208;
               A61M 2205/15; A61M 2205/21; A61M
               2205/3331; A61M 2205/3334; A61M
               2205/3365; A61M 2205/3368; A61M
               2205/3379; A61M 2205/3389; A61M
               2205/3561; A61M 2205/42; A61M
               2205/50; A61M 2205/502; A61M
               2205/75; A61M 16/06
    USPC ...................................................... 128/206.24
    See application file for complete search history.

(56) References Cited

U.S. PATENT DOCUMENTS

| | | | |
|---|---|---|---|
| 5,560,354 | A | 10/1996 | Berthon-Jones et al. |
| 5,687,715 | A | 11/1997 | Landis |
| 6,123,071 | A | 9/2000 | Berthon-Jones et al. |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,397,724 | B2 | 3/2013 | Sher et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2006/0237017 | A1 | 10/2006 | Davidson et al. |
| 2007/0006879 | A1 | 1/2007 | Thornton |
| 2009/0044808 | A1 | 2/2009 | Guney et al. |
| 2009/0050156 | A1 | 2/2009 | Ng et al. |
| 2009/0114229 | A1 | 5/2009 | Frater et al. |
| 2009/0133696 | A1 | 5/2009 | Remmers et al. |
| 2009/0159084 | A1 | 6/2009 | Sher et al. |
| 2010/0000534 | A1 | 1/2010 | Kooij et al. |
| 2011/0162654 | A1* | 7/2011 | Carroll .................. A61M 16/06 |
| | | | 128/206.21 |
| 2011/0315143 | A1 | 12/2011 | Frater |
| 2013/0199537 | A1* | 8/2013 | Formica ............ A61M 16/0616 |
| | | | 128/205.25 |
| 2014/0102456 | A1* | 4/2014 | Ovizinsky ......... A61M 16/0066 |
| | | | 128/205.25 |
| 2015/0047644 | A1 | 2/2015 | Baiko et al. |
| 2015/0059759 | A1 | 3/2015 | Frater et al. |
| 2015/0335846 | A1* | 11/2015 | Romagnoli ........... A61M 16/06 |
| | | | 128/201.13 |
| 2017/0035979 | A1 | 2/2017 | Pedro et al. |
| 2018/0193582 | A1 | 7/2018 | Pedro et al. |
| 2019/0160240 | A1 | 5/2019 | Bothma et al. |
| 2019/0224435 | A1 | 7/2019 | Pedro et al. |
| 2020/0206446 | A1 | 7/2020 | Blaxland |
| 2022/0257890 | A1 | 8/2022 | Zoellner et al. |
| 2022/0409839 | A1 | 12/2022 | Dantanarayana |

FOREIGN PATENT DOCUMENTS

| | | |
|---|---|---|
| CN | 109529164 | 3/2019 |
| EP | 0 634 186 B1 | 8/2000 |
| WO | WO 98/004310 A1 | 2/1998 |
| WO | WO 98/034665 A1 | 8/1998 |
| WO | WO 00/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/111749 A1 | 10/2010 |
| WO | WO 2010/135785 A1 | 12/2010 |
| WO | WO 2012/171072 A1 | 12/2012 |
| WO | WO 2013/020167 A1 | 2/2013 |
| WO | WO 2019/119058 | 6/2019 |
| WO | WO 2021/035306 | 3/2021 |
| WO | WO 2021/046599 | 3/2021 |

OTHER PUBLICATIONS

International Search Report mailed Nov. 25, 2020 in corresponding PCT application PCT/AU2020/050903 (5 pages).

Written Opinion mailed Nov. 25, 2020 in corresponding PCT application PCT/AU2020/050903 (9 pages).

Second Written Opinion mailed Jul. 27, 2021 in corresponding PCT application PCT/AU2020/050903 (7 pages).

International Preliminary Report on Patentability mailed Dec. 17, 2021 in corresponding PCT application PCT/AU2020/050903 (30 pages).

Andrade et al., "Nasal versus oronasal CPAP for obstructive sleep apnea treatment: a meta-analysis", *Chest* (2018), doi: 10.1016/j.chest.2017.10.044 (34 pages).

Ng et al., "Choosing an Oronasal Mask to Deliver Continuous Positive Airway Pressure May Cause More Upper Airway Obstruction or Lead to Higher Continuous Positive Airway Pressure Requirements than a Nasal Mask in Some Patients" A Case Series, Journal Of Clinical Sleep Medicine, vol. 12, No. 9, 2016 pp. 1227-1232 (6 pages).

Extended European Search Report issued Feb. 16, 2023 in related EP Appl. No. 22197470.2 (6 pages).

Notice of Allowance issued in related U.S. Appl. No. 17/929,783, dated Jul. 24, 2025 (14 pages).

European Extended Search Report (EESR) issued in corresponding European Patent Application No. 25184423.9, dated Oct. 11, 2025 (9 pages).

* cited by examiner

Nasal cavity

Oral cavity

Larynx

Vocal folds

Oesophagus

Trachea

Bronchus

Lung

Heart

Diaphragm

Alveolar sacs

Nasal cavity

Nasal bone

Lateral nasal
cartilage

Greater alar
cartilage

Nostril

Lip superior

Lip inferior

Larynx

Hard palate

Soft palate

Oropharynx

Tongue

Epiglottis

Vocal folds

Esophagus

Trachea

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

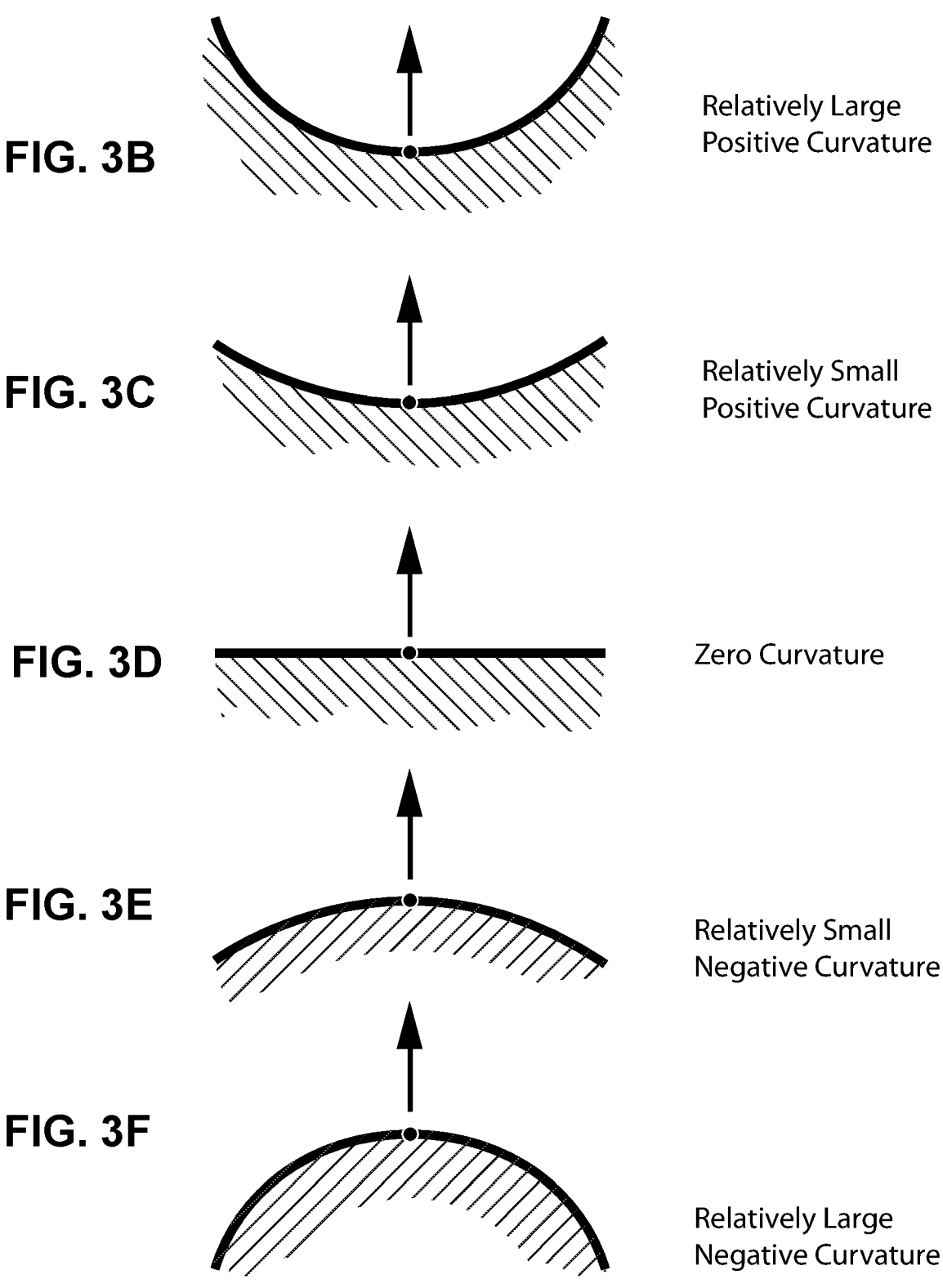
FIG. 3B     Relatively Large Positive Curvature
FIG. 3C     Relatively Small Positive Curvature
FIG. 3D     Zero Curvature
FIG. 3E     Relatively Small Negative Curvature
FIG. 3F     Relatively Large Negative Curvature

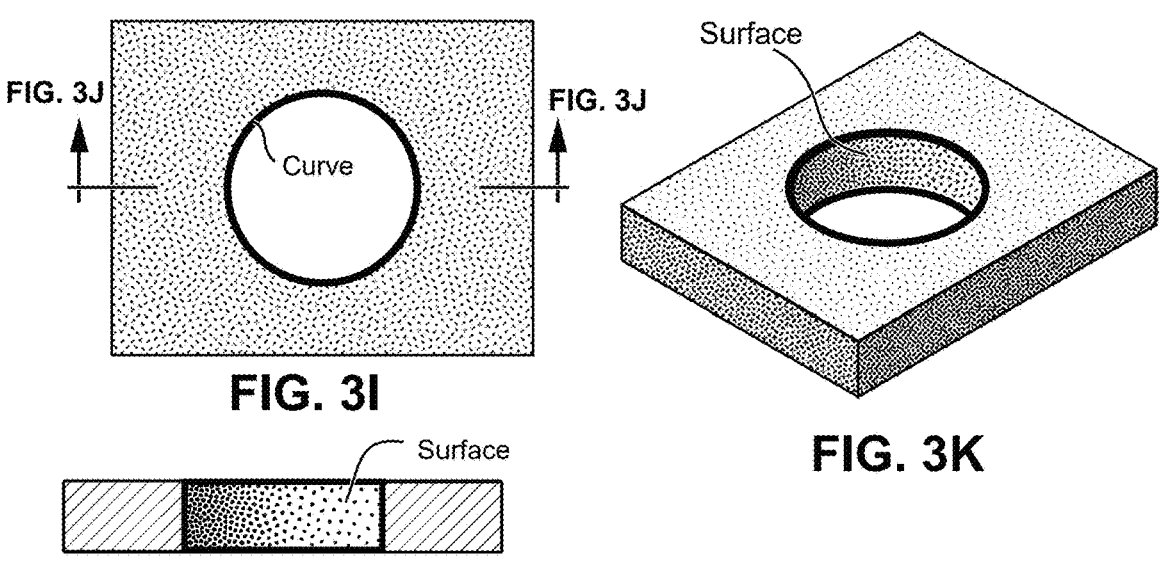
FIG. 3I
FIG. 3K
FIG. 3J
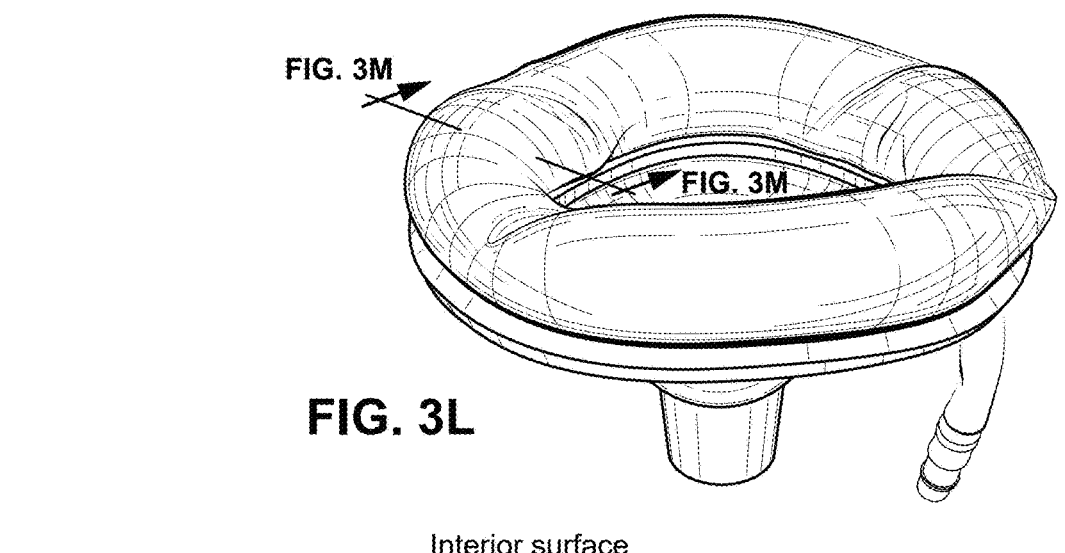
FIG. 3L
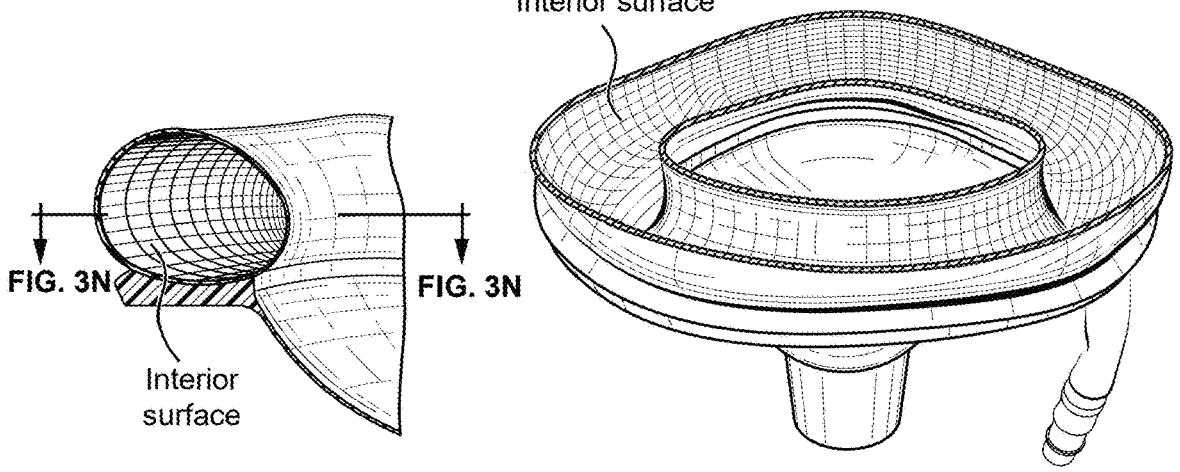
FIG. 3M
FIG. 3N

Left-hand rule
Right-hand rule
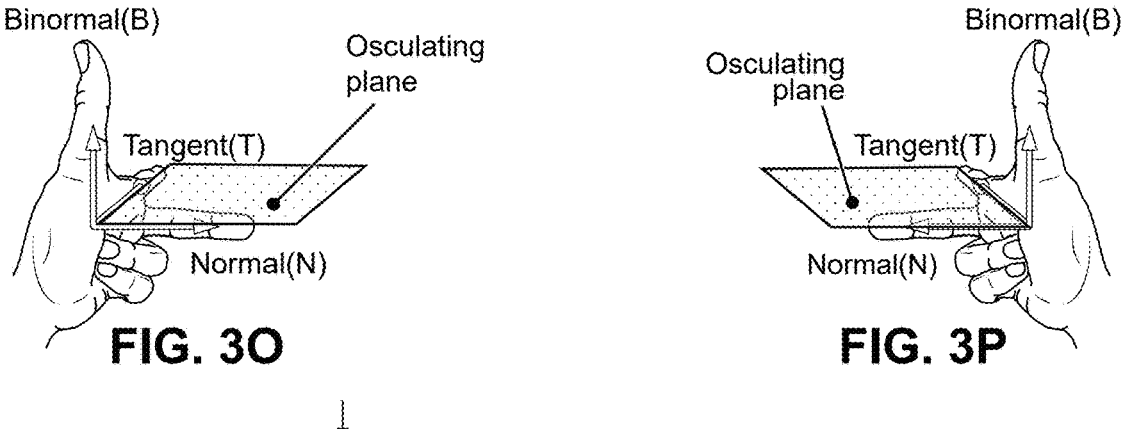
FIG. 3O
FIG. 3P
Left ear helix
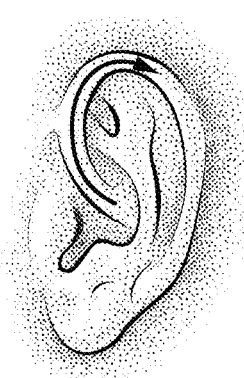
FIG. 3Q
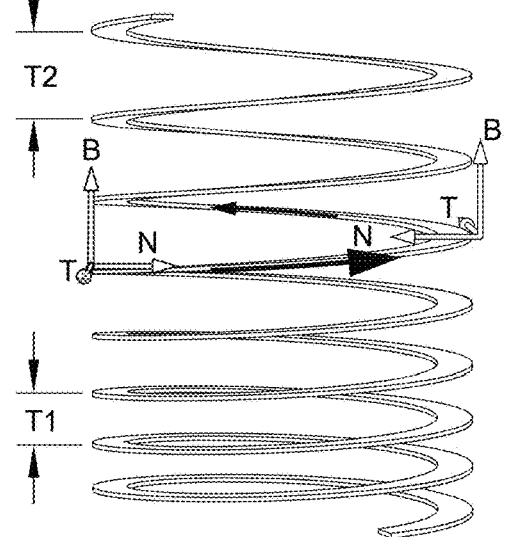
Right-hand helix
Right-hand positive
FIG. 3S
Right ear helix
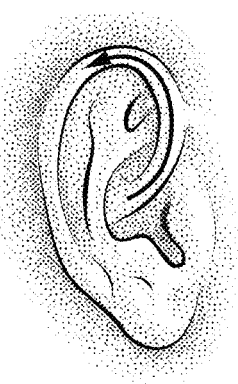
FIG. 3R
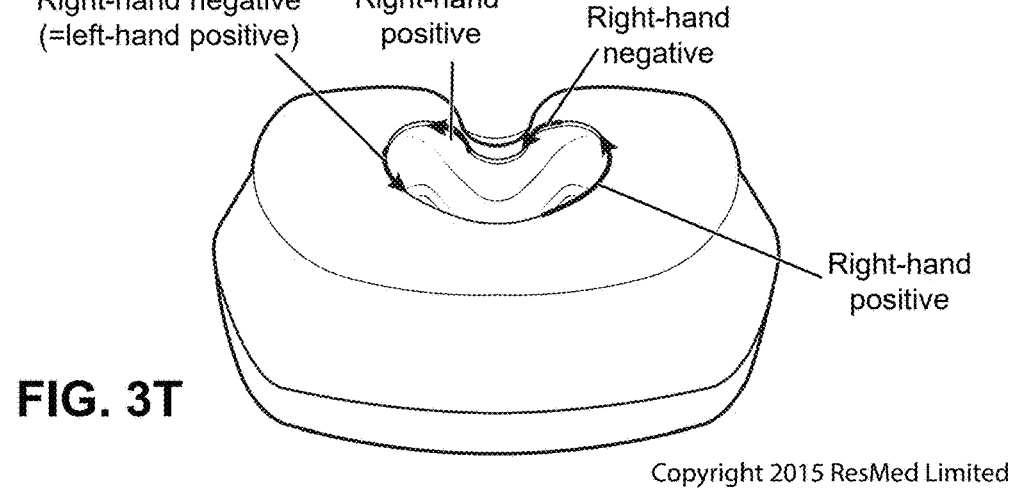
FIG. 3T Nasal cavity Nasal bone Lateral nasal cartilage Greater alar cartilage Nostril Lip superior Lip inferior Hard palate Soft palate (12)

Oropharynx

Tongue

Epiglottis

Vocal folds

Esophagus

Trachea

Larynx 3200
3100
See FIG. 15-2A
3202
3240
3210          3204
3234
3280          3282
3264
FIG. 15-2
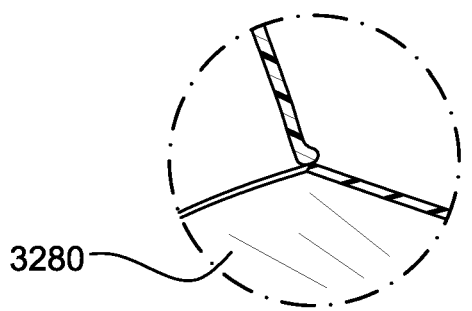
3280
FIG. 15-2A
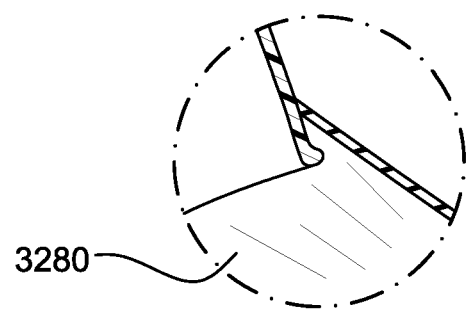
3280
FIG. 15-2B

FIG. 27

DUAL CHAMBER PATIENT INTERFACE WITH AIRFLOW REGULATION

1 CROSS-REFERENCE TO RELATED APPLICATIONS

This application is the U.S. national phase of International Application No. PCT/AU2020/050903 filed Aug. 28, 2020 which designated the U.S. and claims priority to Australian Provisional Application No. 2019903204 filed Aug. 31, 2019, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired CO2 from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH2O).

| RPT Device name | A-weighted sound pressure level dB(A) | Year (approx.) |
|---|---|---|
| C-Series Tango™ | 31.9 | 2007 |
| C-Series Tango™ with Humidifier | 33.1 | 2007 |
| S8 Escape™ II | 30.5 | 2005 |
| S8 Escape™ II with H4i™ Humidifier | 31.1 | 2005 |
| S9 AutoSet™ | 26.5 | 2010 |
| S9 AutoSet™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.5 Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical.

Recently, companies that manufacture large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses or "boli", each bolus timed to coincide with the onset of inhalation. This therapy mode is known as pulsed oxygen delivery (POD) or demand mode, in contrast with traditional continuous flow delivery more suited to stationary oxygen concentrators.

2.2.3.6 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.7 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.8 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed MirageTM (*) | nasal | 29.5 | 21.5 | 1998 |
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |
| ResMed Mirage SwiftTM LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1m distance |
| Conversational speech | 60 | 1m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology is directed to a patient interface comprising: at least one plenum chamber for a patient interface, the plenum chamber being pressurisable to a therapeutic pressure of at least 6 cmH2O above ambient air pressure throughout a patient's respiratory cycle in use.

Another aspect of the present technology is directed to a patient interface comprising a dual chamber cushion assembly.

Another aspect of the present technology is directed to a patient interface comprising a cushion assembly having a nasal chamber and an oral chamber that is pressurizable to a different level than the nasal chamber.

Another aspect of the present technology is directed to a patient interface for sealed delivery of a flow of air at a continuously positive pressure with respect to ambient air pressure to an entrance to a patient's airways including at least an entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing, the patient interface comprising a cushion assembly configured to deliver a flow of air to the patient's airways.

In examples: (a) the cushion assembly includes a nasal chamber pressurisable to a therapeutic pressure of at least 6 cmH$_2$O above ambient air pressure, the nasal chamber configured to, in use, deliver the flow of air to the patient's nasal passageways; (b) the cushion assembly includes an oral chamber pressurisable to a different level than the nasal chamber, the oral chamber configured to, in use, deliver the flow of air to the patient's mouth; (c) the cushion assembly includes at least one inlet port sized and structured to receive the flow of air into at least the nasal chamber; (d) the cushion assembly includes a seal-forming structure constructed and arranged to form a seal with a region of the patient's face surrounding an entrance to the patient's airways, said seal-forming structure having at least one hole formed therein such that the flow of air is delivered to at least an entrance to the patient's nares; (e) the cushion assembly includes a partition forming a wall extending between and separating the nasal chamber and the oral chamber.

In further examples: (a) a first surface of the wall is disposed in the nasal chamber and a second surface of the wall that is opposite the first surface is disposed in the oral chamber; (b) a plurality of holes is formed in the wall extending through the first surface and the second surface to, in use, allow the flow of air to flow from the nasal chamber to the oral chamber in a manner that maintains a pressure in the oral chamber at a level lower than a pressure in the nasal chamber to promote nasal breathing; (c) the plurality of holes comprises at least three holes; (d) the pressure in the nasal chamber is at least 2 cmH$_2$O above the pressure in the oral chamber; (e) the pressure in the nasal chamber is at least 5 cmH$_2$O above the pressure in the oral chamber.

In further examples: (a) the cushion assembly further comprises a flow regulator including a passageway fluidly connecting the nasal chamber and the oral chamber to allow the flow of air to flow from the nasal chamber to the oral chamber; (b) the flow regulator is configured to adjust a size of the passageway to control a volume of the flow of air that flows from the nasal chamber to the oral chamber; (c) the flow regulator is an adjustable valve; (d) the size of the passageway is manually adjustable; (e) the flow regulator further comprises a rotatable dial to manually adjust the size of the passageway; (f) the size of the passageway is automatically adjustable; (g) the patient interface further comprising a sensor to determine a level of resistance in the patient's nasal passageways, wherein, in use, when the level of resistance in the patient's nasal passageways exceeds a first threshold, the flow regulator is configured to automatically adjust the flow of air to increase pressure in the oral chamber.

In further examples: (a) the partition comprises silicone; (b) the seal-forming structure includes a nasal seal comprising the at least one hole such that the flow of air is delivered to at least an entrance to the patient's nares; (c) the seal-forming structure includes an oral seal having a hole formed therein to deliver the flow of air to the patient's mouth; (d) the cushion assembly is an oro-nasal cushion assembly and the seal-forming structure is configured to, in use, form a seal below the patient's pronasale; (e) the patient interface further comprising a pair of headgear tubes configured to deliver the flow of air to the cushion assembly, the pair of headgear tubes being configured to, in use, extend along respective sides of the patient's face between the patient's eye and ear.

In further examples: (a) the cushion assembly is a full-face cushion assembly and the seal-forming structure is configured to, in use, form a seal above the patient's pronasale; (b) the seal-forming structure is configured to, in use, form a seal along the patient's nasal bridge; (c) the wall extends from a patient-contacting side of the cushion assembly to a non-patient contacting side of the cushion assembly; (d) the wall forms an upper surface of the mouth chamber and a lower surface of the nasal chamber; (e) the patient interface further comprising a joint forming a hollow interior to fluidly connect the nasal chamber and the oral chamber, the wall being disposed in the hollow interior of the joint.

In further examples: (a) the cushion assembly further comprises a nasal cushion and a separate oral cushion, wherein the seal-forming structure includes a nasal seal comprising the at least one hole such that the flow of air is delivered to at least an entrance to the patient's nares, the nasal cushion comprising the nasal seal, wherein the seal-forming structure includes an oral seal having a hole formed therein to deliver the flow of air to the patient's mouth, the oral cushion comprising the oral seal; (b) the wall is disposed in the nasal cushion, in the oral cushion, or in a fluidly connecting structure therebetween.

In further examples: (a) the cushion assembly is configured such that, in use, the nasal chamber is pressurized in a range of 8 to 14 cmH$_2$O above ambient air pressure while the oral chamber is pressurized in a range of 4 to 7.5 cmH$_2$O above ambient air pressure; (b) the cushion assembly is configured such that, in use, the nasal chamber is pressurized in a range of 14 to 20 cmH$_2$O above ambient air pressure while the oral chamber is pressurized in a range of 7.5 to 10.5 cmH$_2$O above ambient air pressure; (c) the patient interface further comprises a positioning and stabilizing structure to provide a force to hold the seal-forming structure in a therapeutically effective position on the patient's head, the positioning and stabilising structure being constructed and arranged so that at least a portion overlies a region of the patient's head superior to an otobasion superior of the patient's head in use.

Another aspect of the present technology is directed to a patient interface for sealed delivery of a flow of air at a continuously positive pressure with respect to ambient air pressure to an entrance to a patient's airways including at least an entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing, the patient interface comprising a cushion assembly configured to deliver a flow of air to the patient's airways.

In examples: (a) the cushion assembly includes a nasal chamber pressurisable to a therapeutic pressure of at least 6 cmH$_2$O above ambient air pressure, the nasal chamber configured to, in use, deliver the flow of air to the patient's nasal passageways; (b) the cushion assembly includes an oral chamber pressurisable to a different level than the nasal chamber, the oral chamber configured to, in use, deliver the flow of air to the patient's mouth; (c) the cushion assembly includes at least one inlet port sized and structured to receive the flow of air into at least the nasal chamber; (d) the cushion assembly includes a seal-forming structure constructed and arranged to form a seal with a region of the patient's face surrounding an entrance to the patient's airways, said seal-forming structure having at least one hole formed therein such that the flow of air is delivered to at least an entrance to the patient's nares; (e) the cushion assembly includes a partition forming a wall extending between and separating the nasal chamber and the oral chamber, the wall extending across an interior of the cushion assembly from a patient-contacting side of the cushion assembly to a non-patient contacting side of the cushion assembly such that a first surface of the wall is disposed in the nasal chamber and a second surface of the wall that is opposite the first surface is disposed in the oral chamber; (f) the cushion assembly includes a flow regulator interfacing with the partition and including a passageway fluidly connecting the nasal chamber and the oral chamber to allow the flow of air to flow from the nasal chamber to the oral chamber.

In examples: (a) the flow regulator is configured to adjust a size of the passageway to control a volume of the flow of air that flows from the nasal chamber to the oral chamber; (b) the flow regulator is configured to, in use, maintain the therapeutic pressure in the nasal chamber at a level that is at least 2 cmH$_2$O above a pressure in the oral chamber to promote nasal breathing; (c) the flow regulator is an adjustable valve; (d) the size of the passageway is manually adjustable; (e) the flow regulator further comprises a rotatable dial to manually adjust the size of the passageway.

In further examples: (a) the size of the passageway is automatically adjustable; (b) the patient interface further comprises a sensor to determine a level of resistance in the patient's nasal passageways, wherein, in use, when the level of resistance in the patient's nasal passageways exceeds a first threshold, the flow regulator is configured to automatically adjust the flow of air to increase pressure in the oral chamber.

In further examples: (a) the partition comprises silicone; (b) the cushion assembly is an oro-nasal cushion assembly and the seal-forming structure is configured to, in use, form a seal below the patient's pronasale; (c) the patient interface further comprises a pair of headgear tubes configured to deliver the flow of air to the cushion assembly, the pair of headgear tubes being configured to, in use, extend along respective sides of the patient's face between the patient's eye and ear.

Another aspect of the present technology is directed to a method of training a patient to breathe primarily through the nasal passageways.

Another aspect of the present technology is directed to a method of training a patient to increase nasal breathing.

Another aspect of the present technology is directed to a method of training a patient to increase nasal breathing by creating a pressure differential in nasal and oral chambers of a cushion assembly thereby causing the patient's soft palate to move anteriorly thereby decreasing impedance in the nasal passageway while increasing impedance in the oral passageway to promote nasal breathing.

Another aspect of the present technology is directed to a method of training a patient to increase nasal breathing by gradually decreasing a therapeutic pressure in an oral chamber over the course of multiple treatments.

Another aspect of the present technology is directed to a method for training a patient to increase nasal breathing from a flow of air provided, at a continuously positive pressure with respect to ambient air pressure, to an entrance to the patient's airways including at least an entrance of the patient's nares, wherein a patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing, the method comprising providing a cushion assembly of the patient interface configured to convey a flow of air to the patient's airways.

In examples: (a) the cushion assembly includes a nasal chamber configured to convey the flow of air to the patient's nasal passageways; (b) the cushion assembly includes an oral chamber configured to convey the flow of air to the patient's mouth, the oral chamber being pressurizable to a different level than the nasal chamber; (c) during a first treatment, providing a therapeutic pressure in the oral chamber that enables the patient to breathe through the patient's mouth; (d) during subsequent treatments, gradually decreasing the therapeutic pressure in the oral chamber to train the patient to breathe primarily through the patient's nasal passageways.

In further examples: (a) during the first treatment, the therapeutic pressure in the oral chamber is greater than or the same as the therapeutic pressure in the nasal chamber; (b) during the first treatment, the therapeutic pressure in the oral chamber is in a range of 6 to 30 cmH$_2$O above ambient air pressure; (c) during the first treatment, the therapeutic pressure in the nasal chamber is in a range of 6 to 30 cmH$_2$O above ambient air pressure; (d) during the subsequent treatments, the therapeutic pressure in the oral chamber gradually decreases to a level below 15 cmH$_2$O above ambient air pressure; (e) during the subsequent treatments, the therapeutic pressure in the oral chamber gradually decreases to a level below 10 cmH$_2$O above ambient air pressure.

In further examples: (a) the cushion assembly further comprises a partition forming a wall extending between and separating the nasal chamber and the oral chamber; (b) the cushion assembly further comprises at least one passageway fluidly connecting the nasal chamber and the oral chamber to convey the flow of air from the nasal chamber to the oral chamber; (c) the cushion assembly further comprises an adjustable flow regulator to control the therapeutic pressure in the oral chamber; (d) the therapeutic pressure in the oral chamber is controlled by adjusting a volume of the flow of air conveyed from the nasal chamber to the oral chamber.

Another aspect of the present technology relates to a patient interface for delivery of respiratory therapy to a patient to promote nasal breathing, comprising: a nares portion including a nasal chamber and a nares sealing portion adapted to form a seal with the patient's nares; the nasal chamber including an opening adapted to selectively receive pressurized, breathable gas; and an inlet conduit connected to the patient interface to deliver pressurized, breathable gas, wherein the patient interface may be adapted to deliver the pressurized, breathable gas to the nares portion so that the pressure in the nasal chamber may be greater than the natural impedance of the patient's nasal passageways.

Another aspect of the present technology relates to a method of promoting nasal breathing comprising: securing a patient interface to a patient comprising a nares portion including a nasal chamber and a nares sealing portion adapted to form a seal with the patient's nares; delivering pressurized, breathable gas to the nares portion so that the pressure in the nasal chamber may be greater than the natural impedance of the patient's nasal passageways.

Another aspect of the present technology relates to a patient interface for promoting nasal breathing as a nose breathing training aid. The patient interface for promoting nasal breathing may be used as part of respiratory therapy such as CPAP therapy.

Another aspect of the present technology relates to a patient interface comprising a nares portion including a nasal chamber and a nares sealing portion adapted to form a seal with the patient's nares; the nasal chamber including an opening adapted to selectively receive pressurized, breathable gas; and an inlet conduit connected to the patient interface to deliver pressurized, breathable gas, wherein the patient interface is adapted to deliver the pressurized, breathable gas to the nares portion so that the pressure in the nasal chamber is greater than the natural impedance of the patient's nasal passageways. This pressurized, breathable gas may be delivered through the nasal passageway such that this gas is able to escape through the patient's mouth creating undesirable and uncomfortable mouth leak, thereby encouraging the patient to close their mouth and breathe nasally, hence promoting nasal breathing.

Another aspect of the present technology relates to a patient interface further comprising an oral portion including an oral chamber and an oral sealing portion adapted to form a seal with the patient's mouth, both the nasal chamber and the oral chamber including an opening adapted to selectively receive the pressurized, breathable gas, the inlet conduit being connected to at least one of the nares portion and the an oral portion to deliver pressurized, breathable gas, and wherein the patient interface may be adapted to preferentially deliver the pressurized, breathable gas to the nares portion.

Another aspect of the present technology is a patient interface for delivery of respiratory therapy to a patient, comprising, a nares portion including a nasal chamber and a nares sealing portion adapted to form a seal with the patient's nares; an oral portion including an oral chamber and an oral sealing portion adapted to form a seal with the patient's mouth, both the nasal chamber and the oral chamber including an opening adapted to selectively receive pressurized, breathable gas; and an inlet conduit connected to at least one of the nares portion and the oral portion to deliver pressurized, breathable gas, wherein the patient interface may be adapted to preferentially deliver the pressurized, breathable gas to the nares portion wherein on preferential delivery of the pressurized breathable gas to the nares portion, the pressure in the nasal chamber may be greater than the natural impedance of the patient's nasal passageways, thereby delivering more air into the nasal passageway than the mouth to promote nasal breathing.

Another aspect of the present technology is a patient interface for delivery of respiratory therapy to a patient in which the pressure in the nasal chamber may be greater than the pressure in the oral chamber.

Another aspect of one form of the present technology is a patient interface that is moulded or otherwise constructed with a perimeter shape which is complementary to that of an intended wearer.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
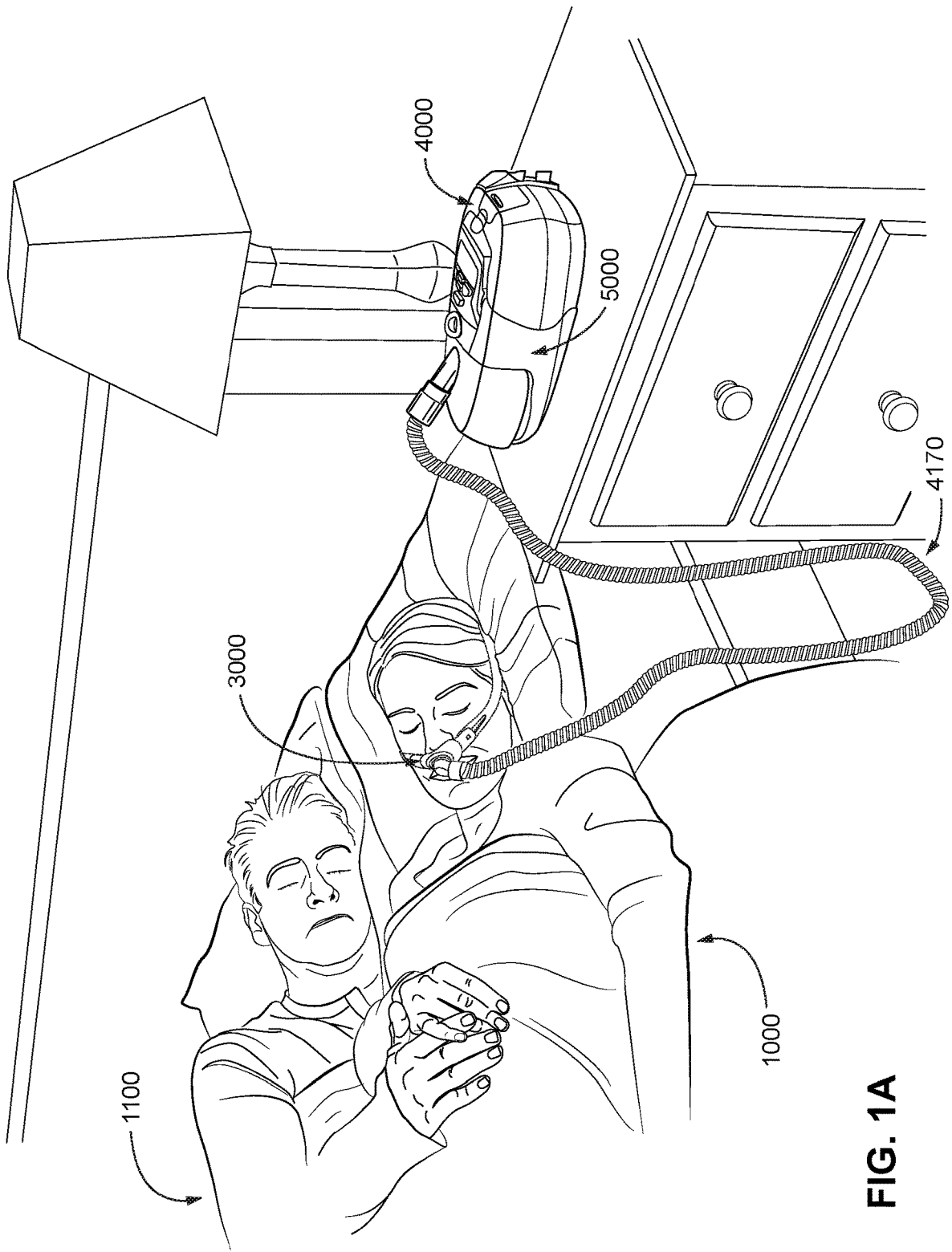
Figure 1B:
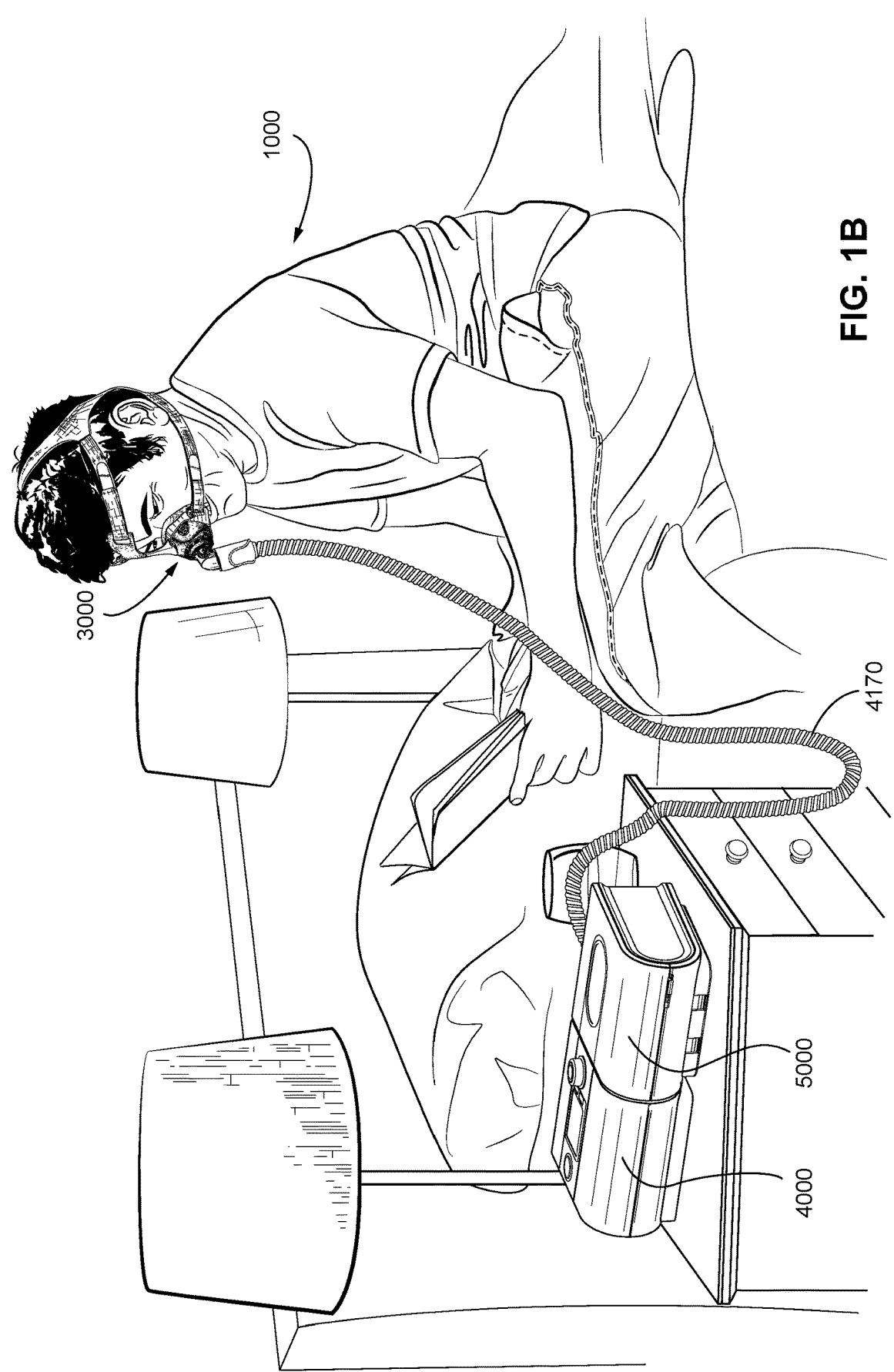
Figure 1C:
Figure 2A:
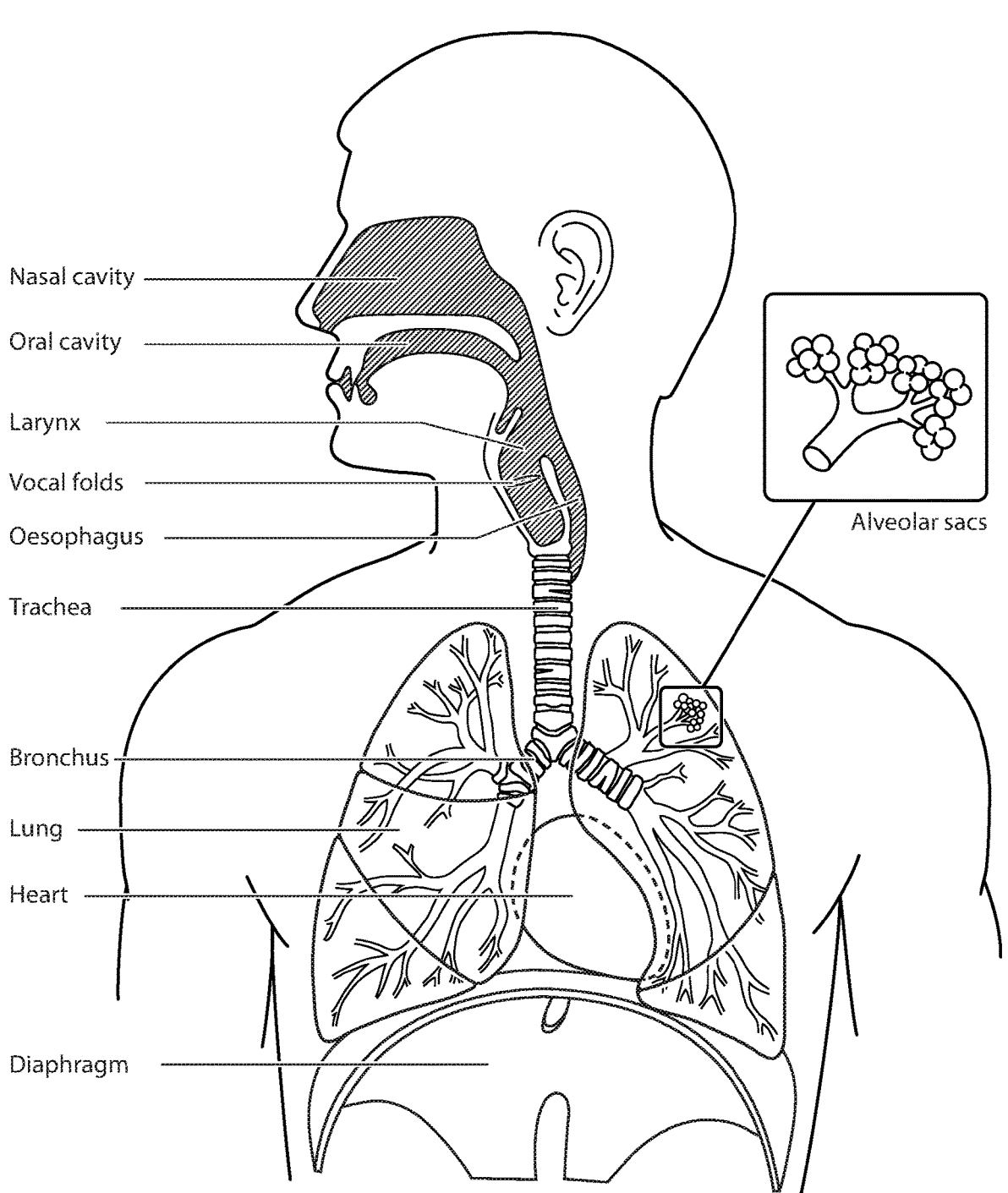
FIG. 2A shows an overview of a human respiratory system including the nasal and oral cavities, the larynx, vocal folds, oesophagus, trachea, bronchus, lung, alveolar sacs, heart and diaphragm.
Figure 2B:
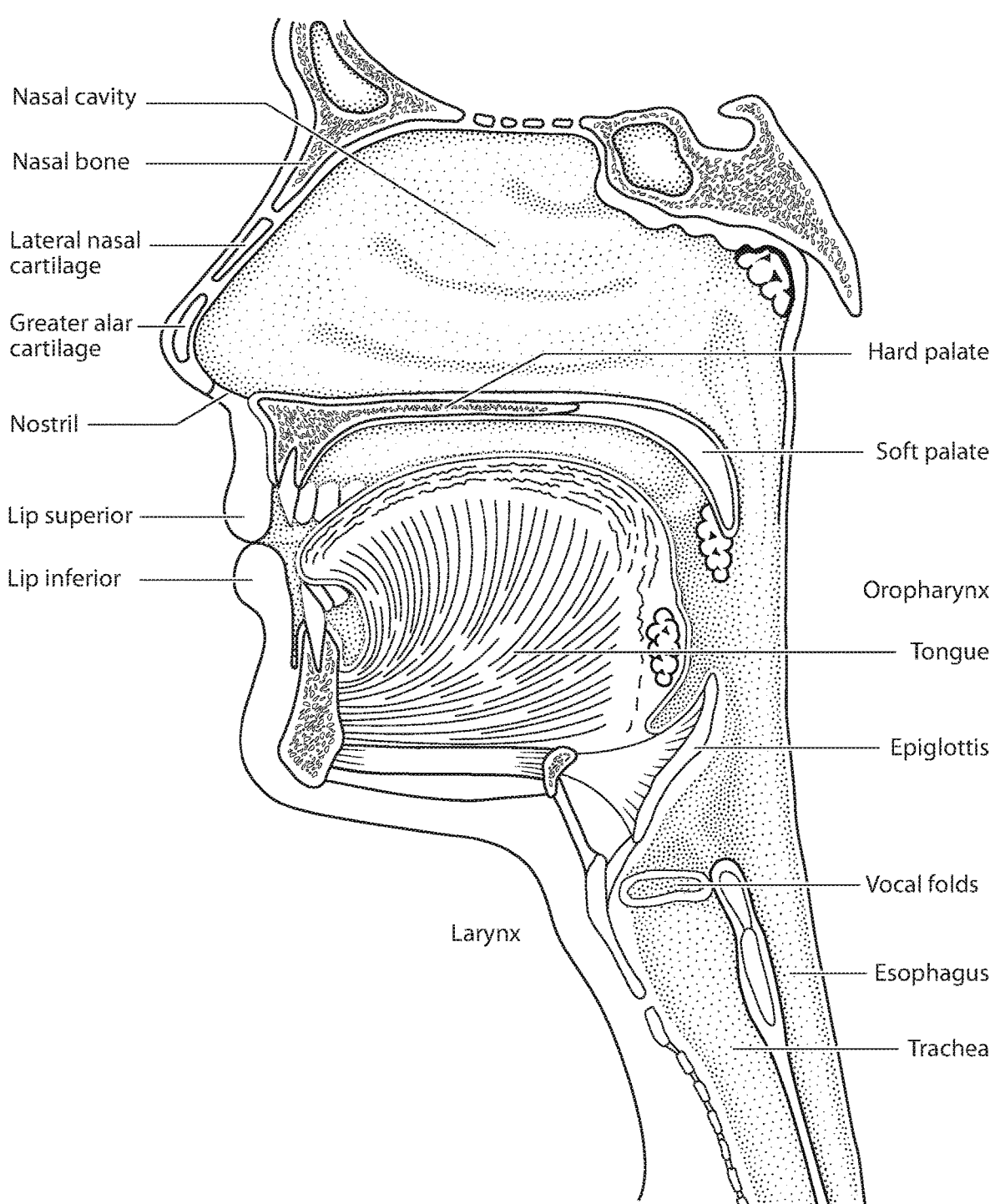
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
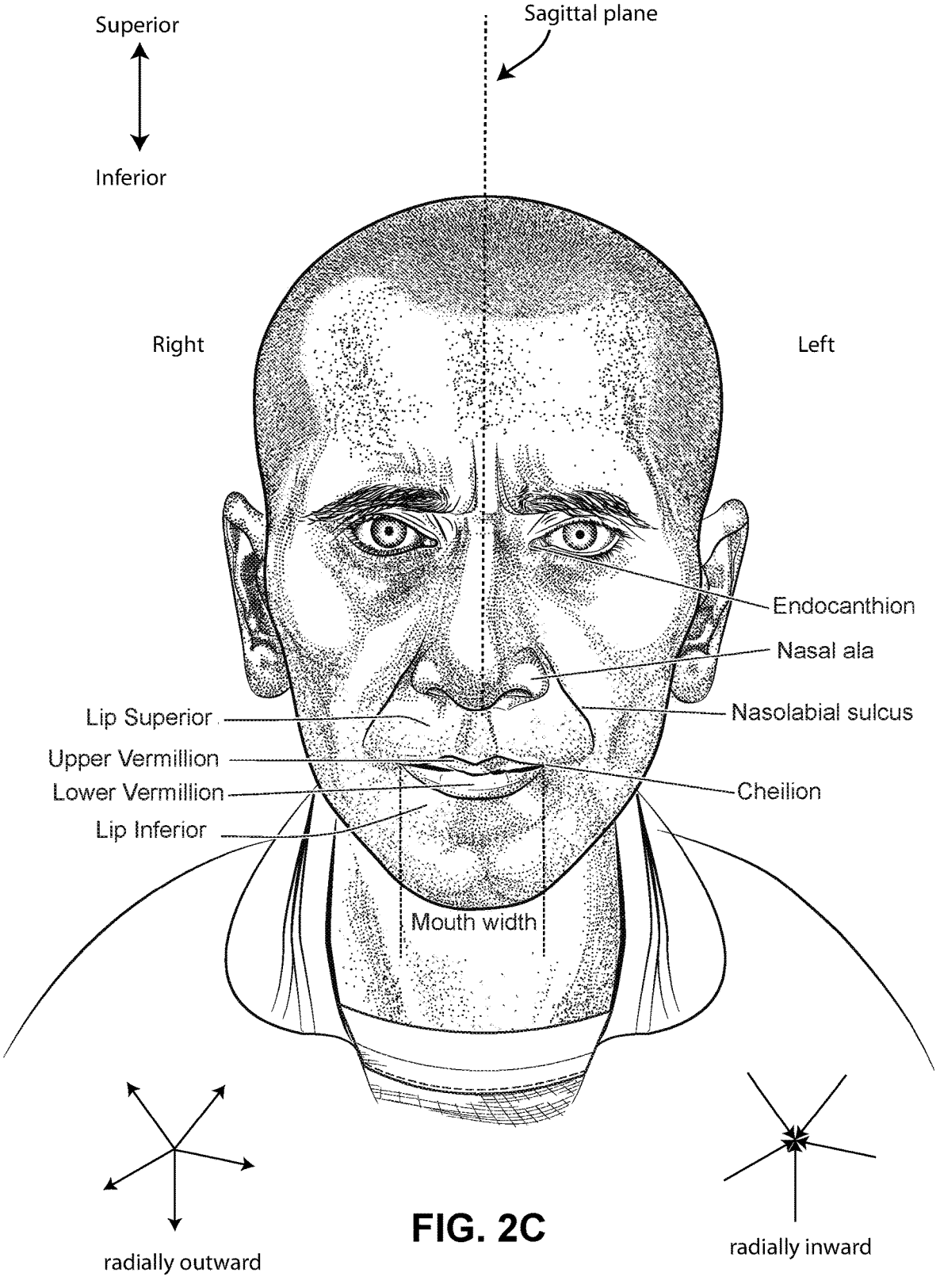
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
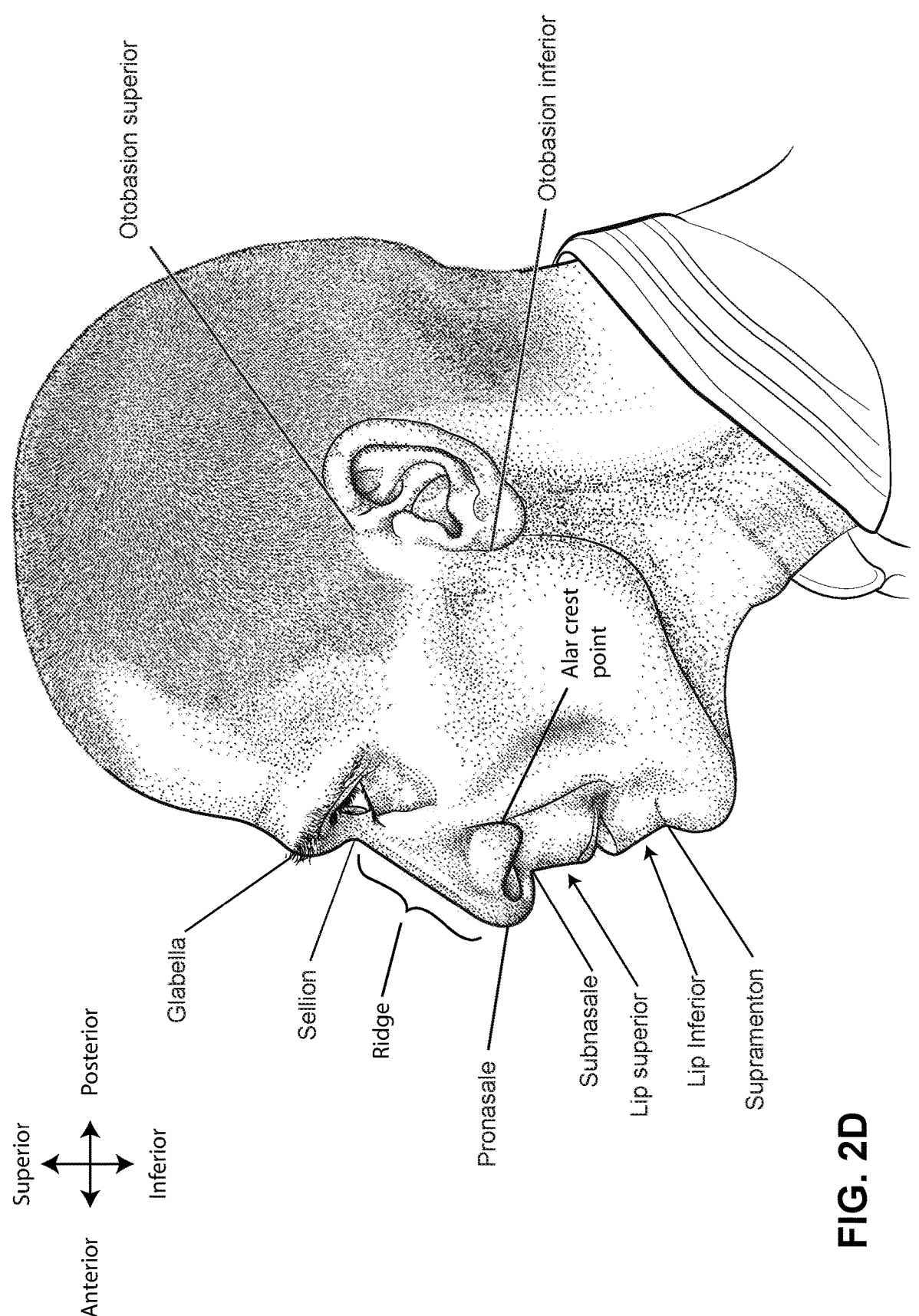
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
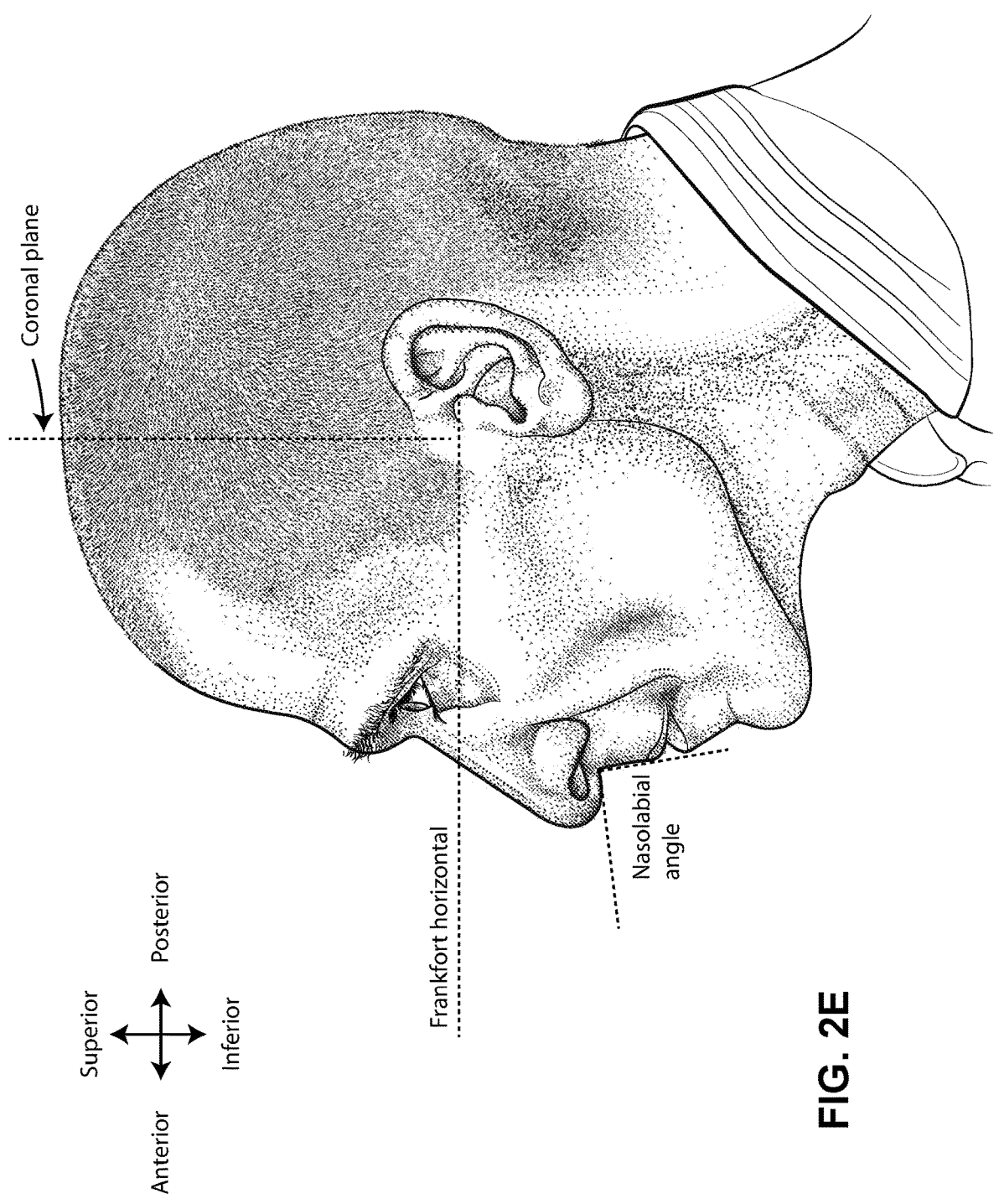

FIG. 2E is a further side view of a head. The approximate locations of the Frankfort horizontal and nasolabial angle are indicated. The coronal plane is also indicated.

Figure 2F:
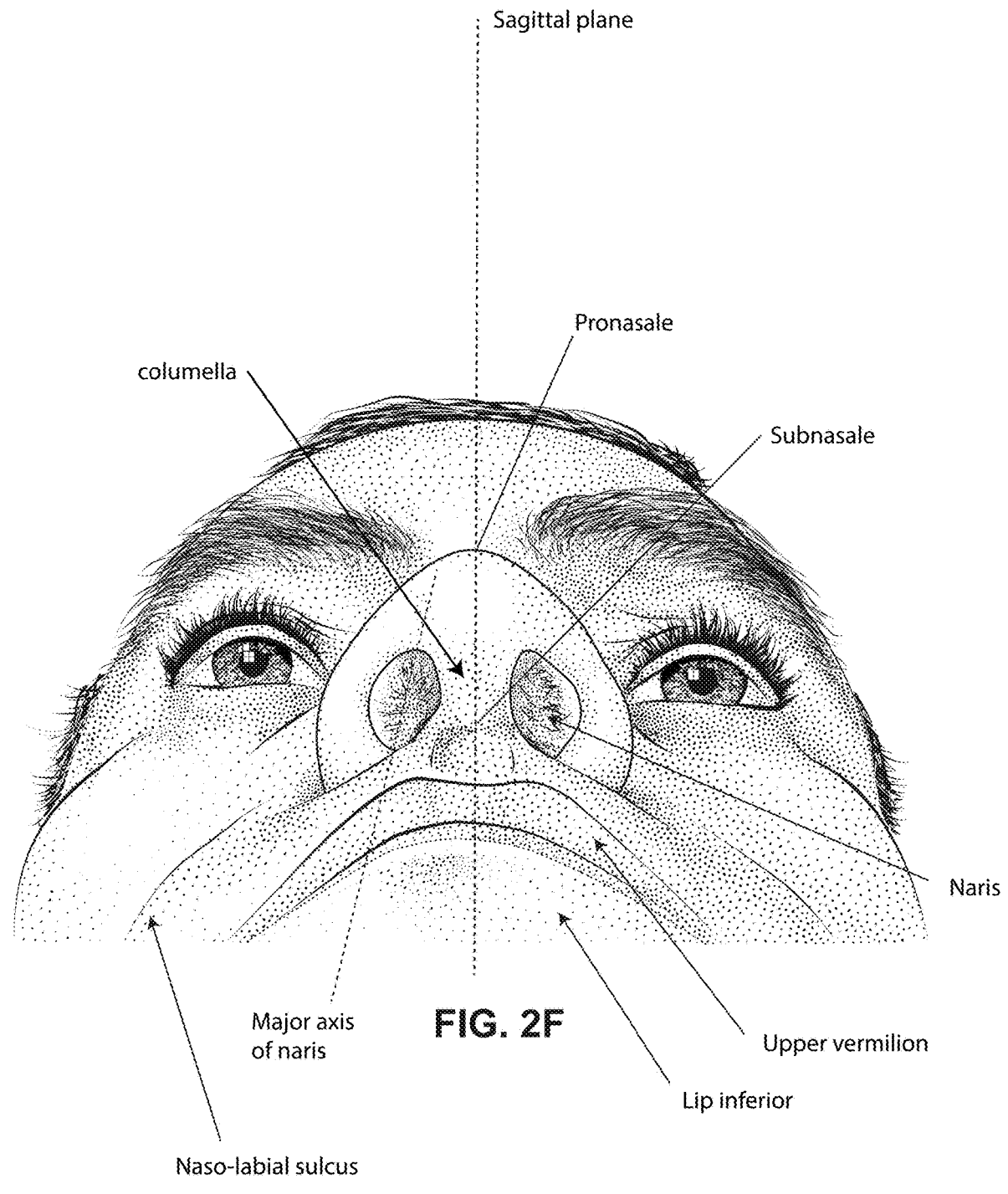

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
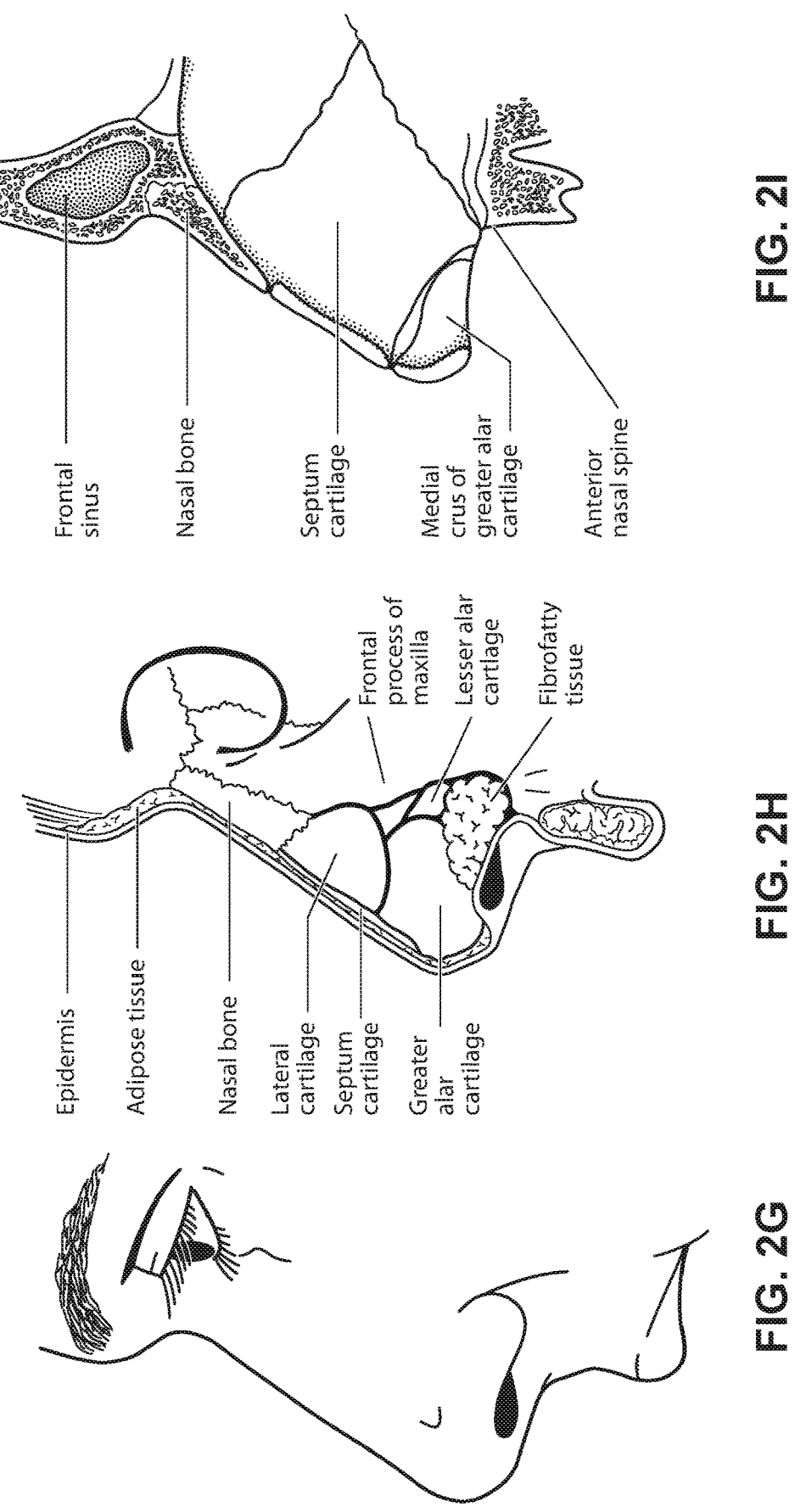

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
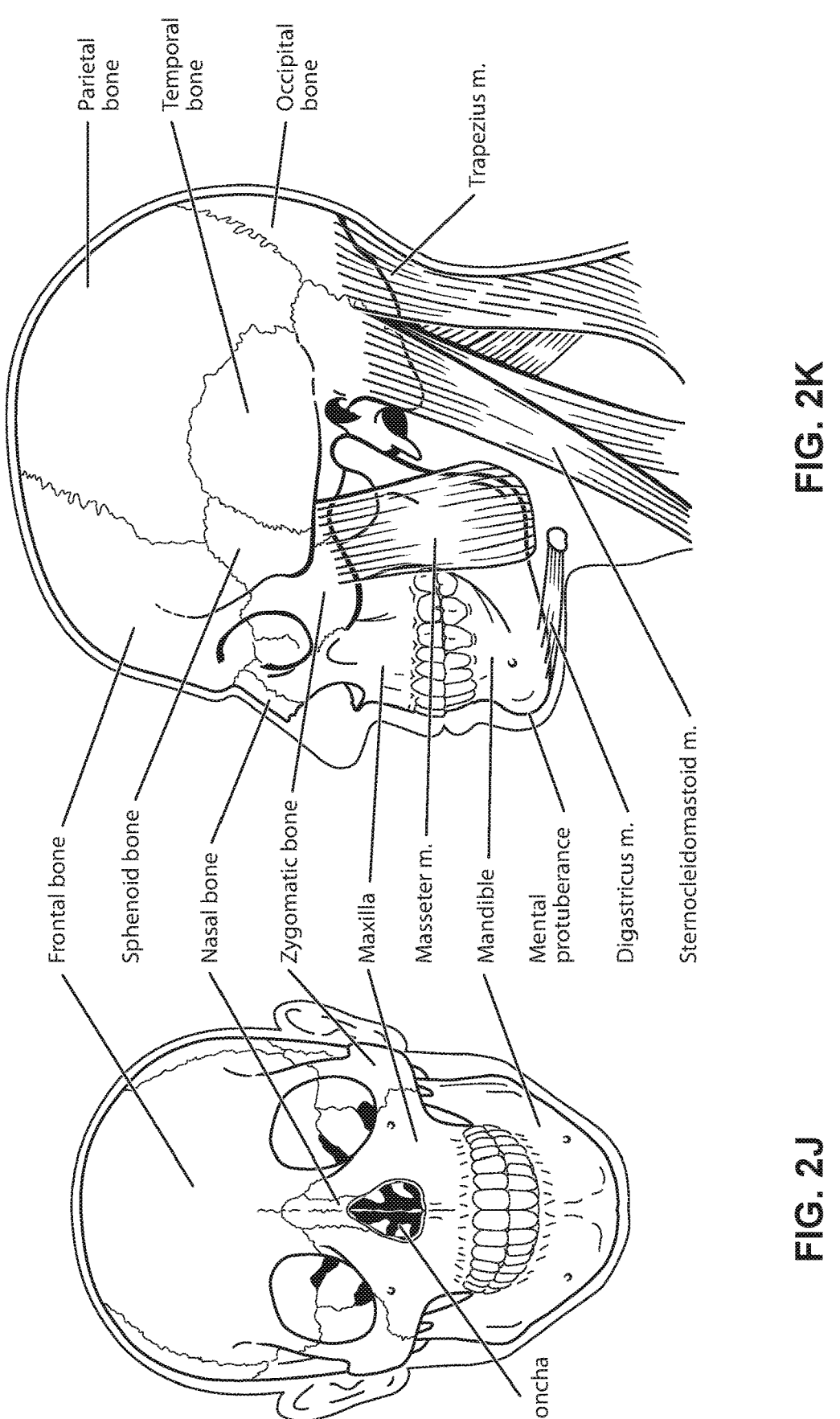

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
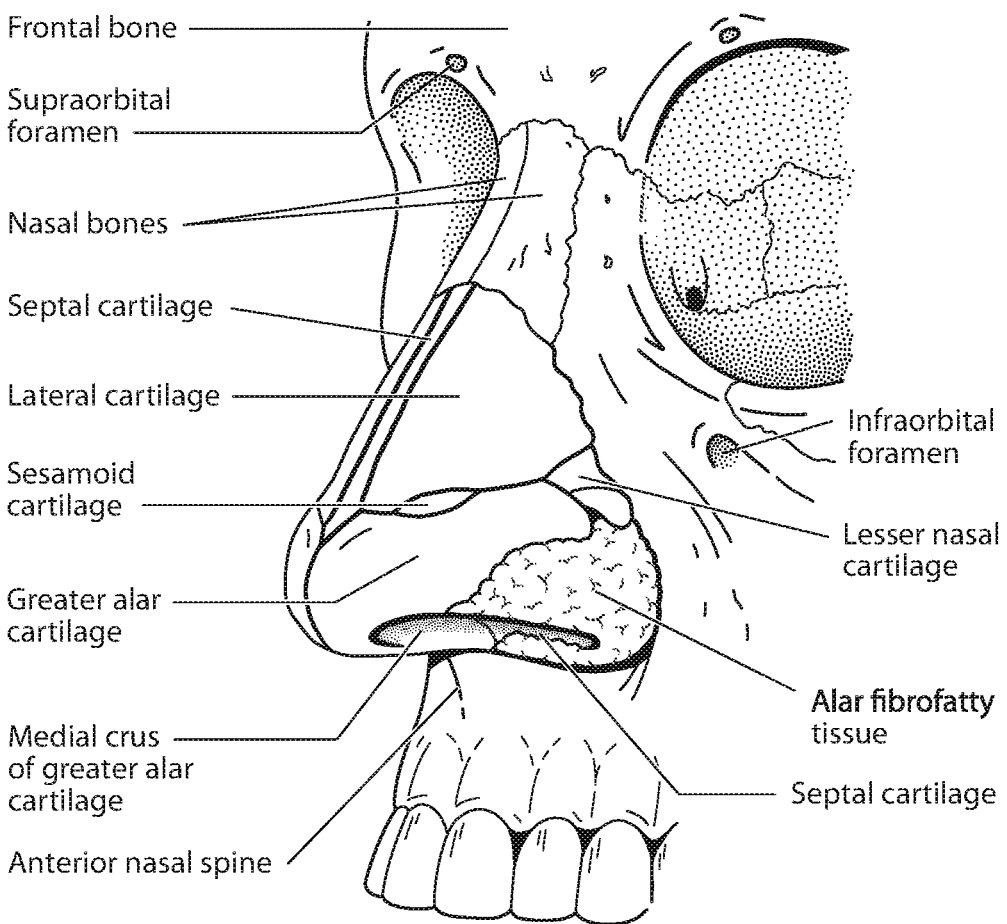

FIG. 2L shows an anterolateral view of a nose.

4.3 Patient Interface

Figure 3A:
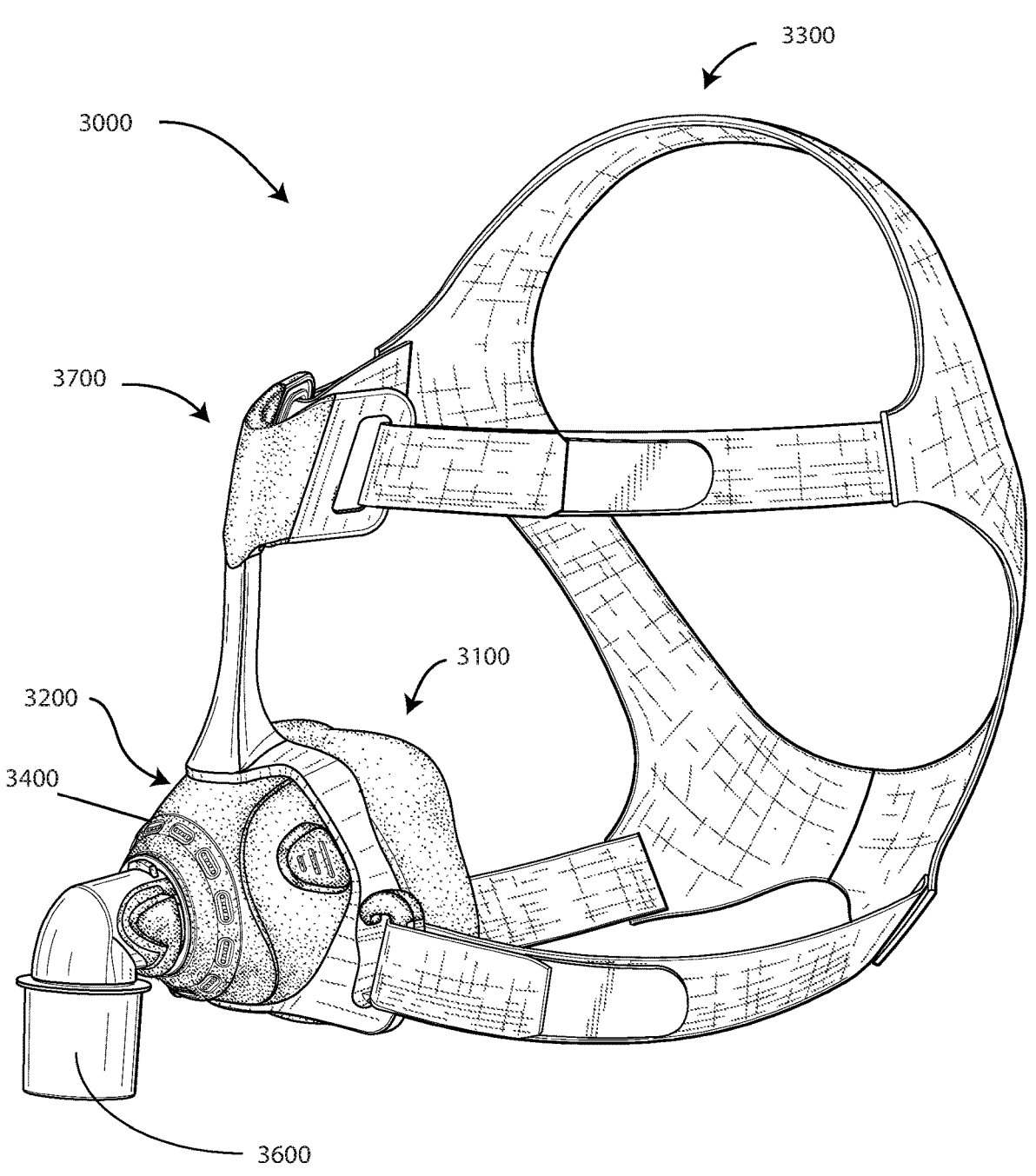

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
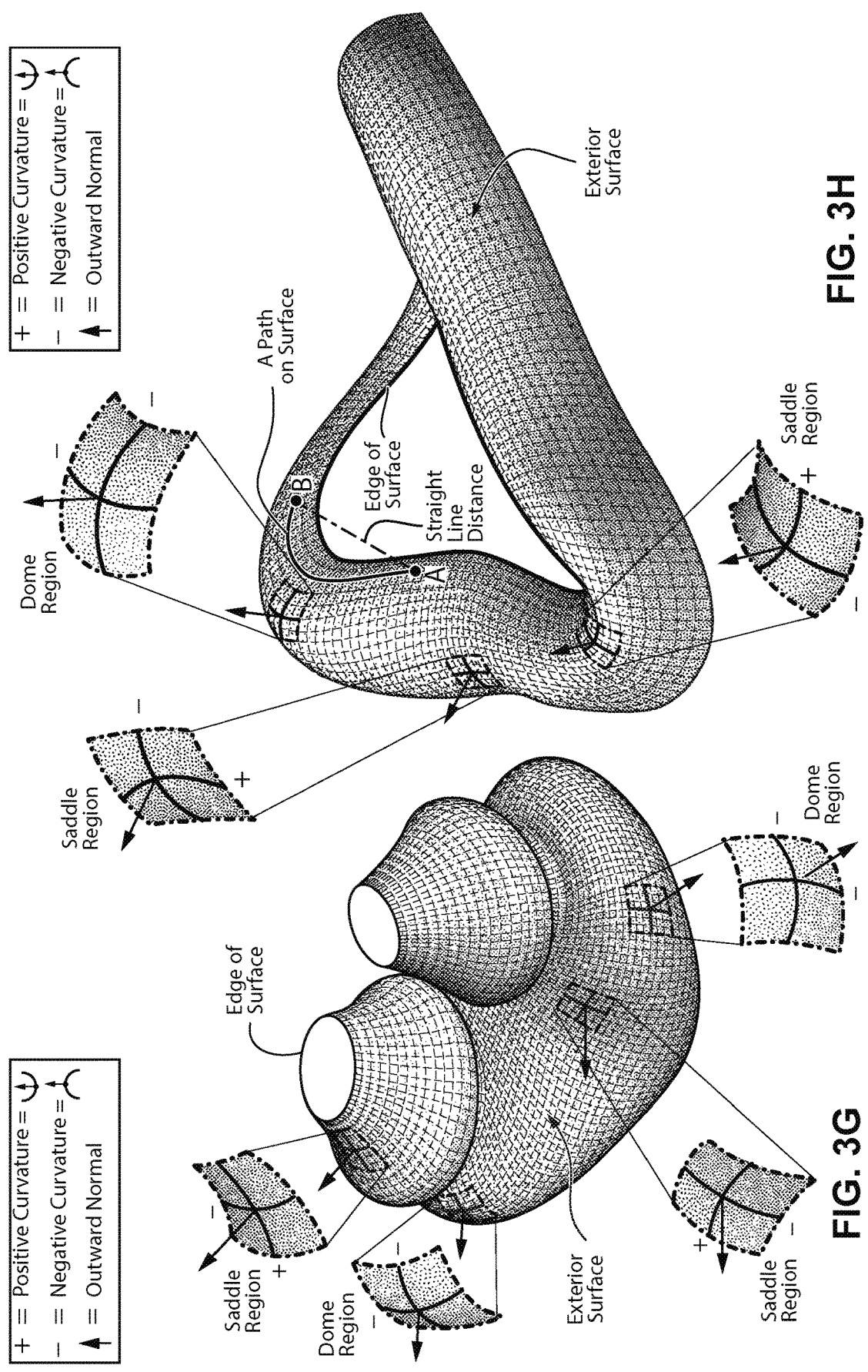

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
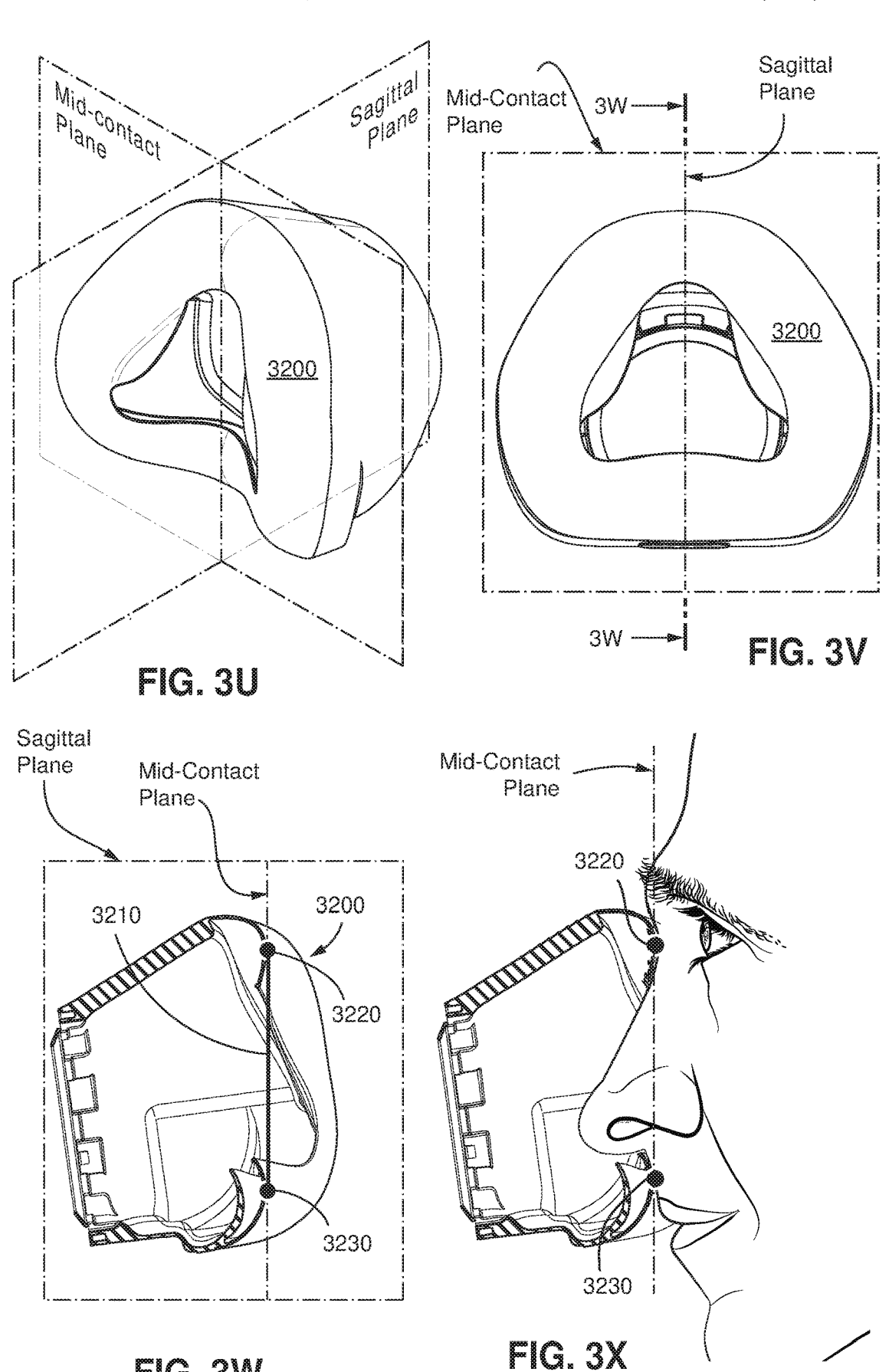

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 3Y:
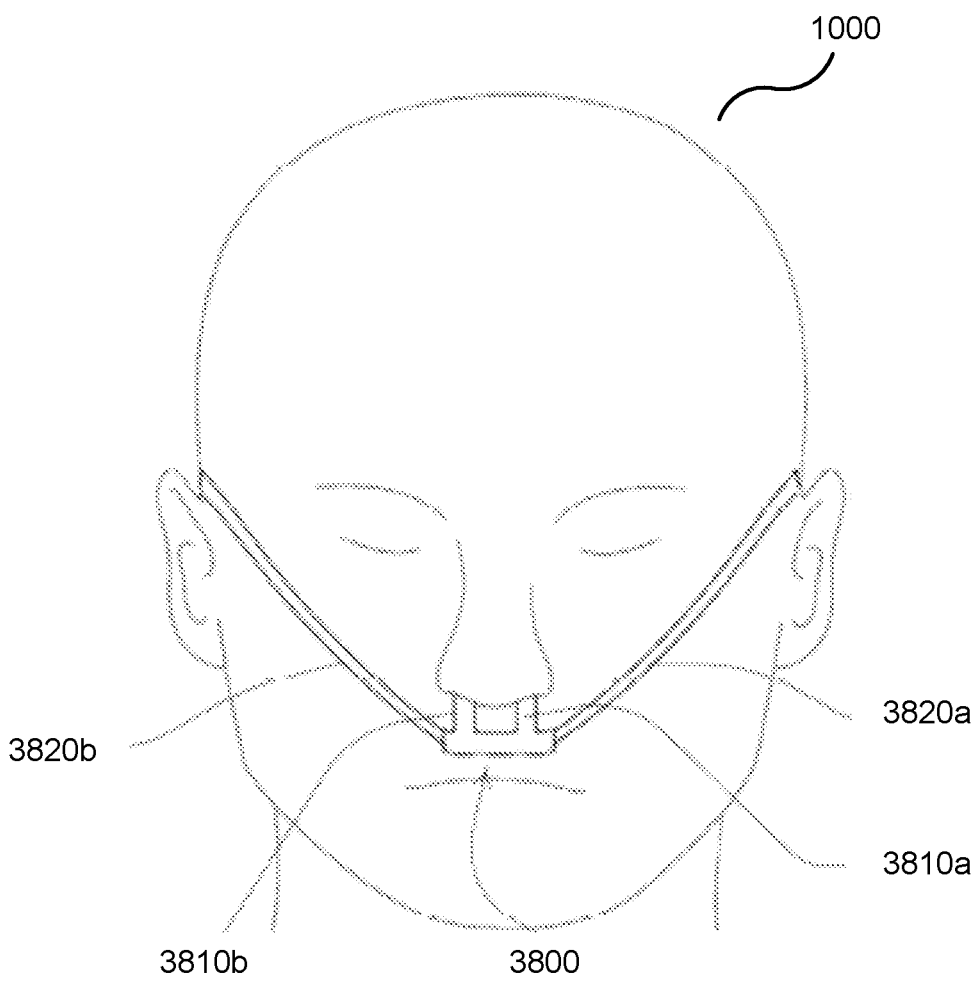

FIG. 3Y shows a patient interface in the form of a nasal cannula in accordance with one form of the present technology.

4.4 RPT Device

Figure 4A:
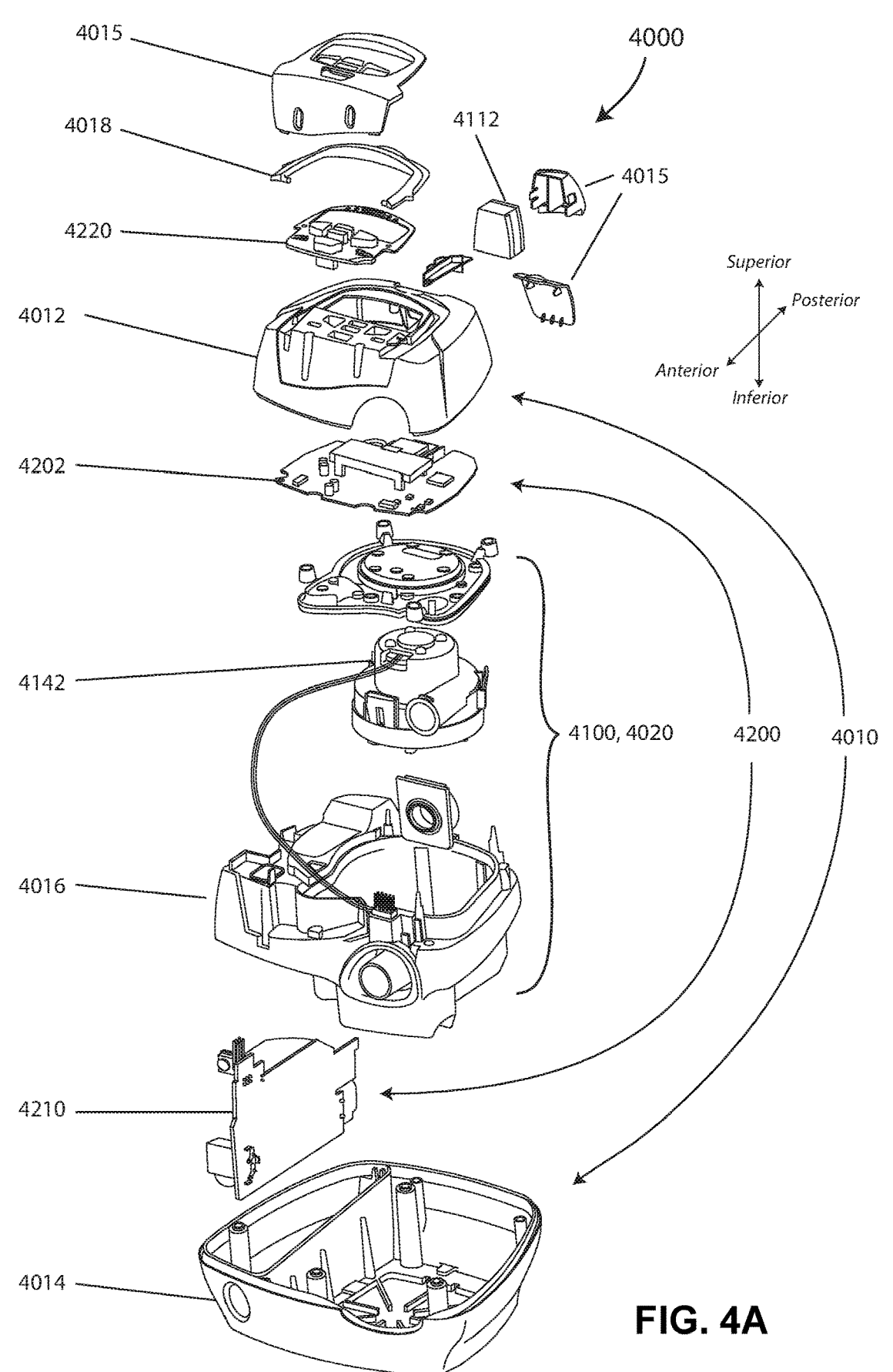

FIG. 4A shows an RPT device in accordance with one form of the present technology.

Figure 4B:
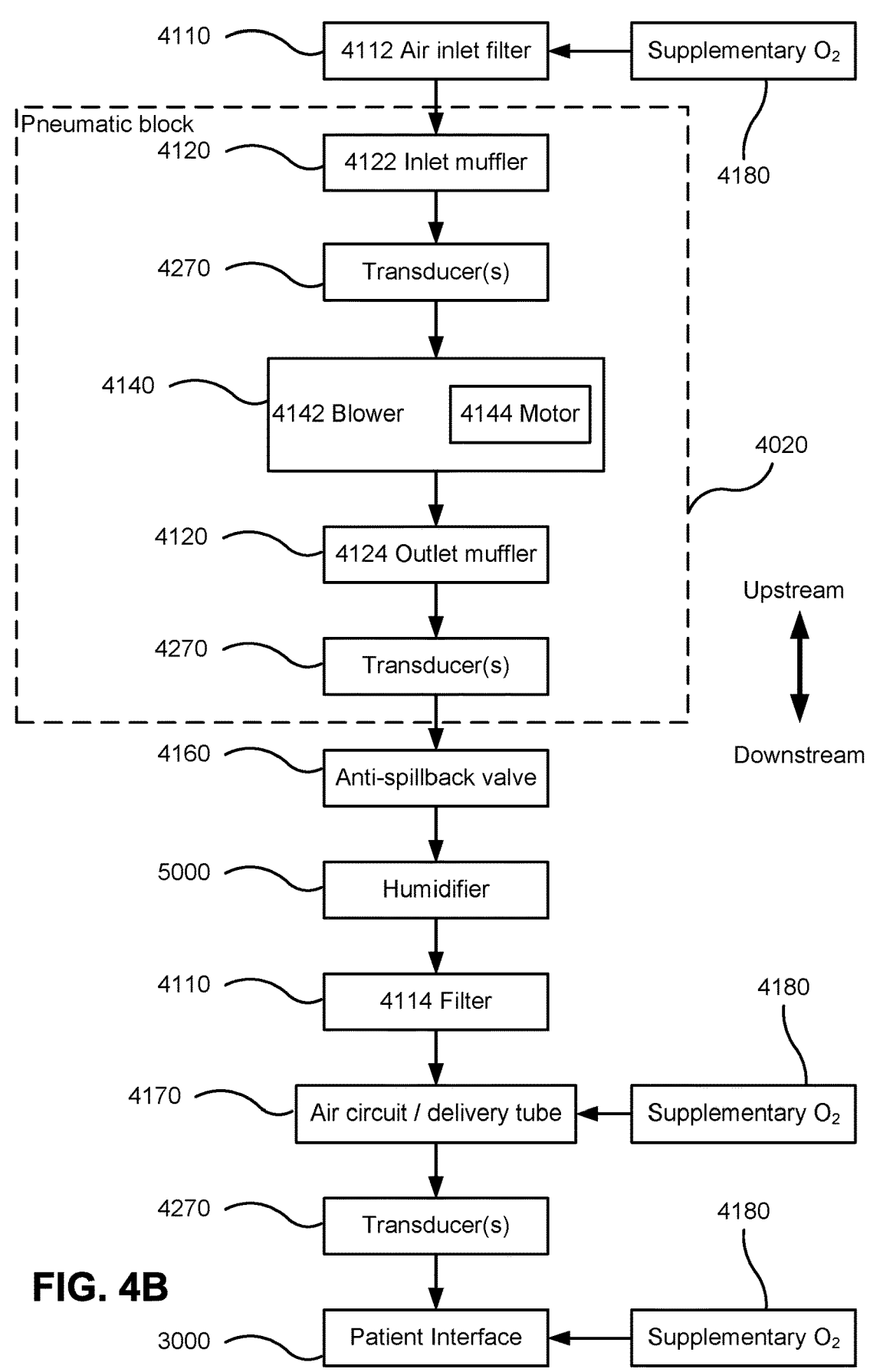

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
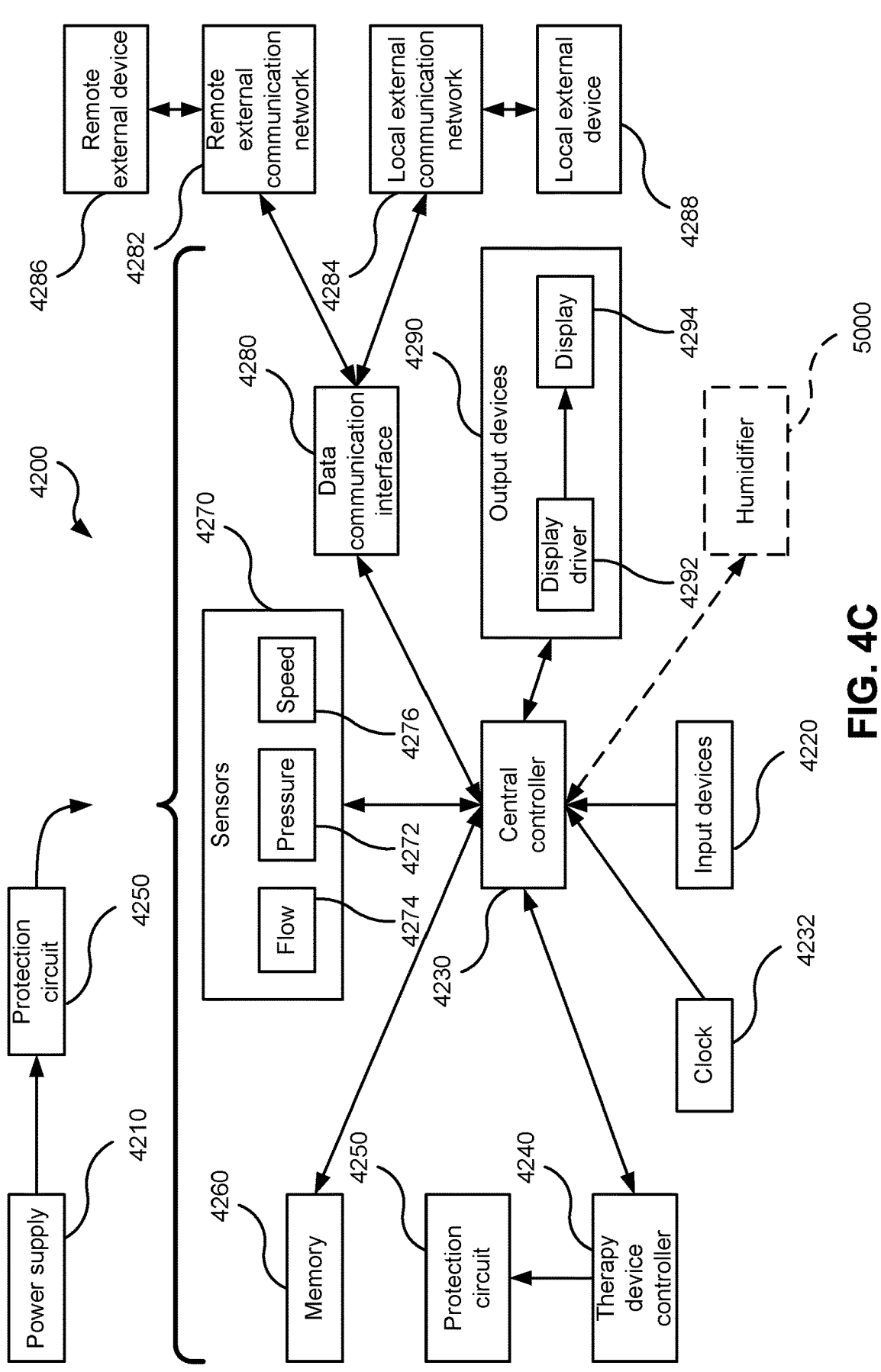

FIG. 4C is a schematic diagram of the electrical components of an RPT device in accordance with one form of the present technology.

Figure 4D:
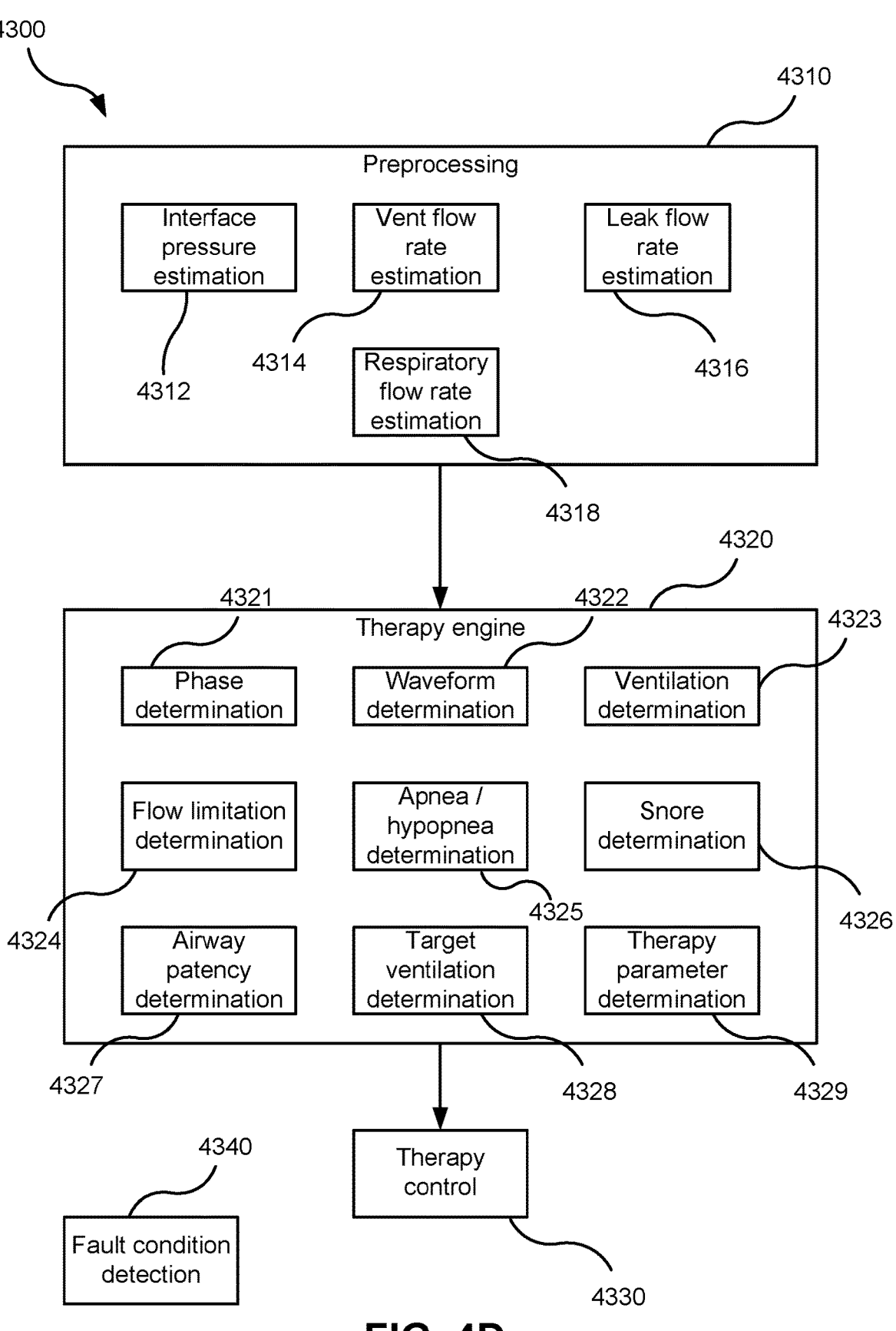

FIG. 4D is a schematic diagram of the algorithms implemented in an RPT device in accordance with one form of the present technology.

Figure 4E:
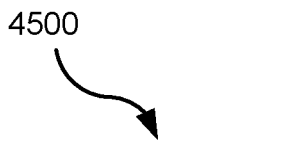
Figure 4E:
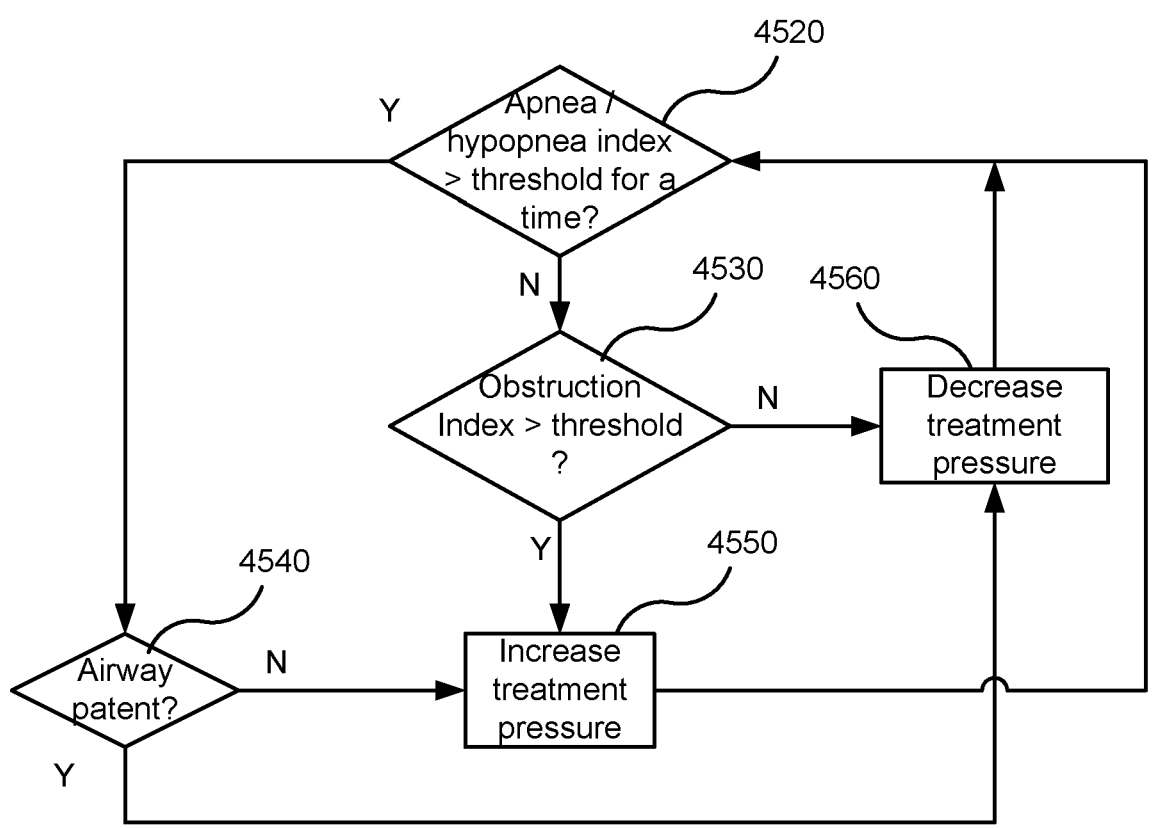

FIG. 4E is a flow chart illustrating a method carried out by the therapy engine module of FIG. 4D in accordance with one form of the present technology.

4.5 Humidifier

Figure 5A:
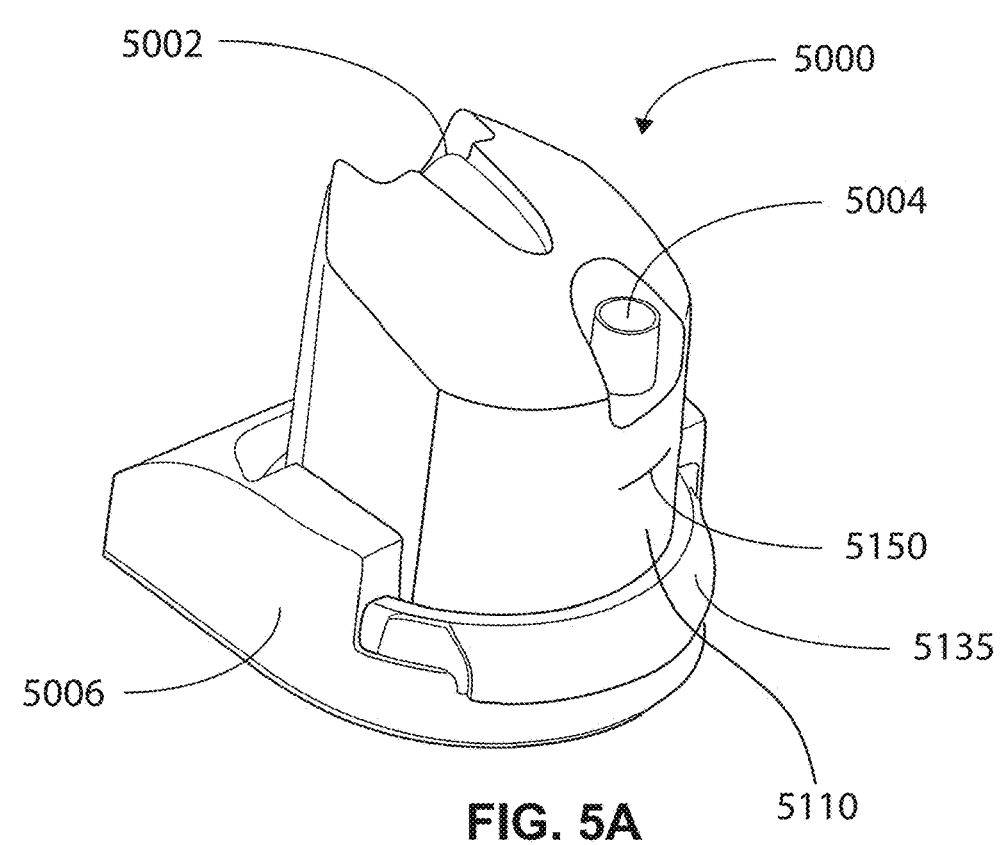

FIG. 5A shows an isometric view of a humidifier in accordance with one form of the present technology.

Figure 5B:
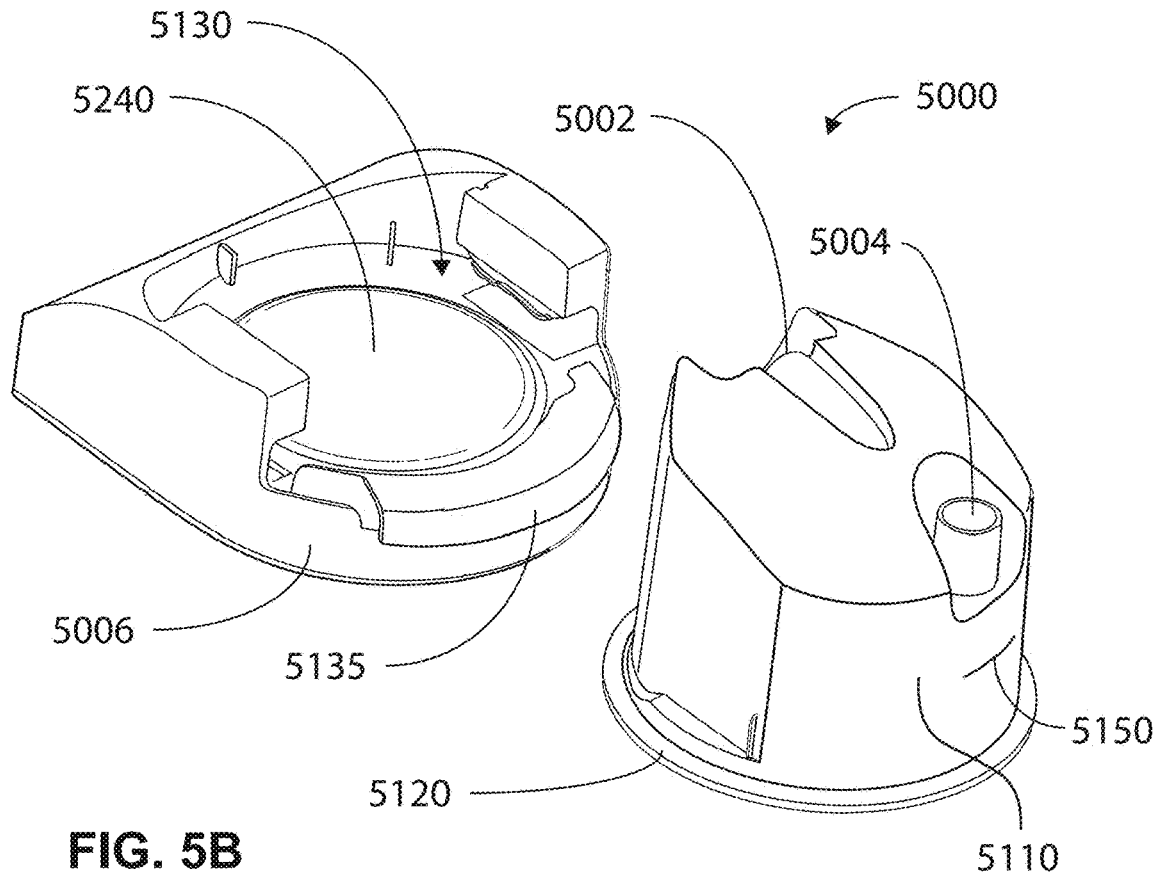

FIG. 5B shows an isometric view of a humidifier in accordance with one form of the present technology, showing a humidifier reservoir 5110 removed from the humidifier reservoir dock 5130.

Figure 5C:
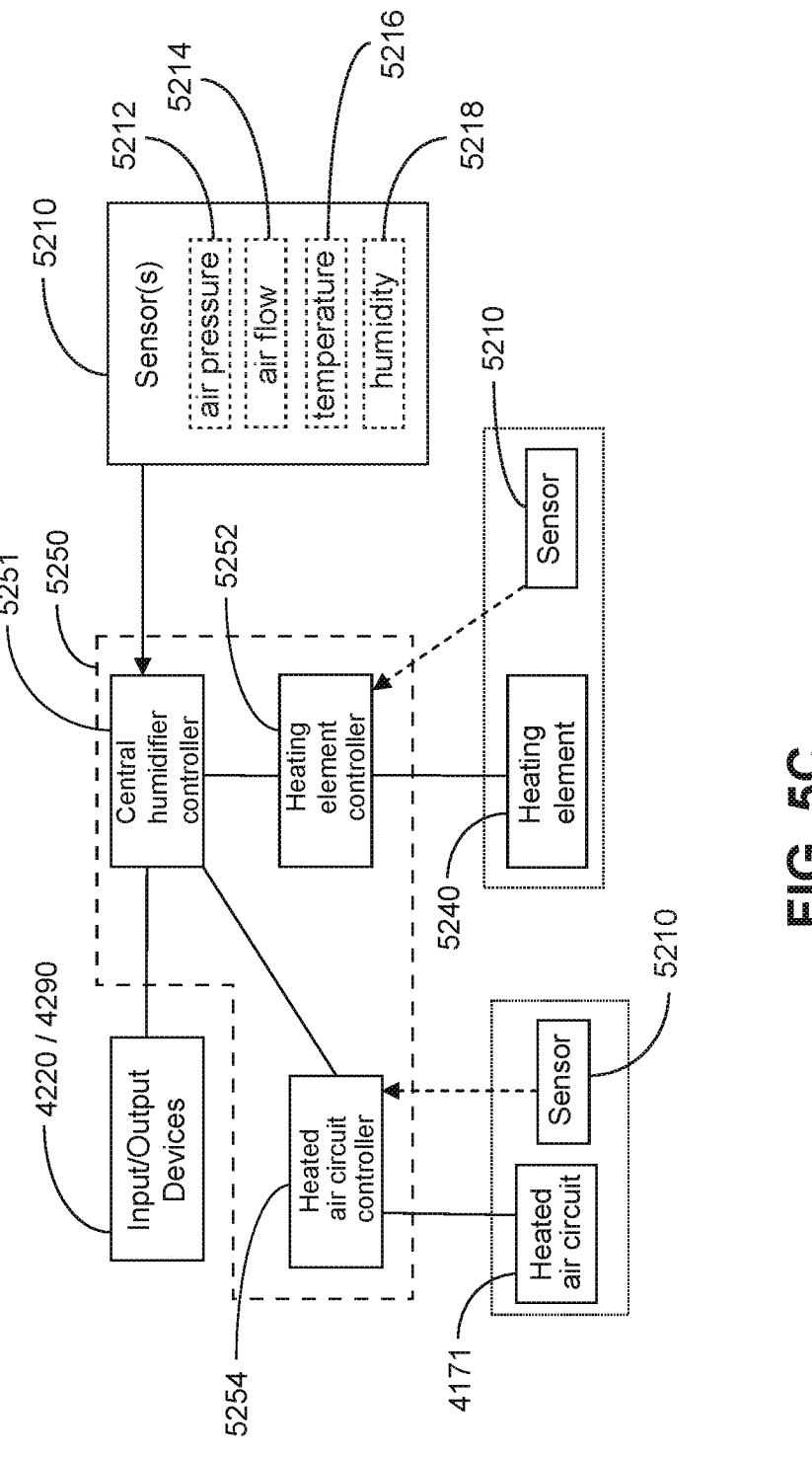

FIG. 5C shows a schematic of a humidifier in accordance with one form of the present technology.

4.6 Breathing Waveforms

Figure 6A:
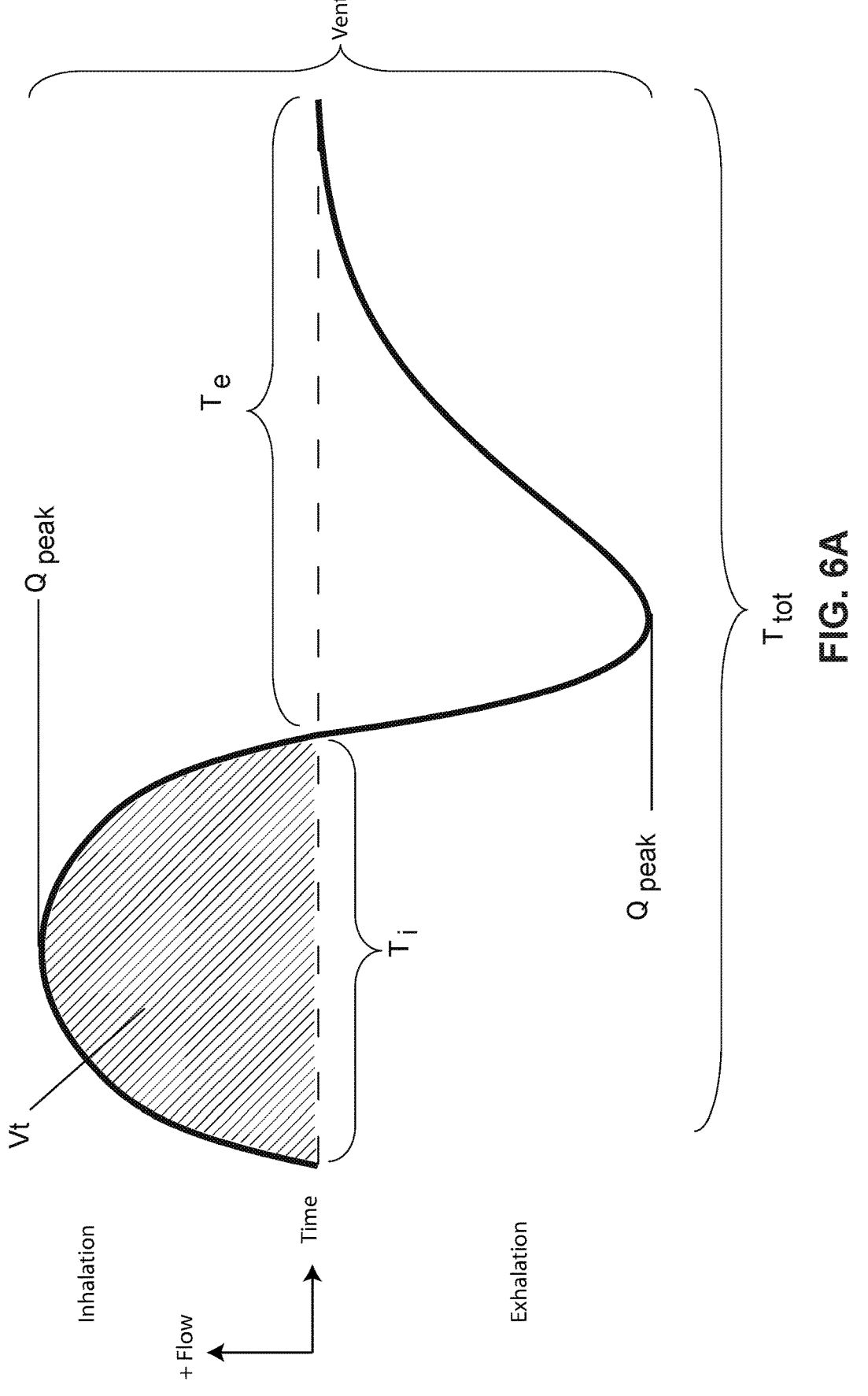

FIG. 6A shows a model typical breath waveform of a person while sleeping.

4.7 Patient Interface Examples of the Present Technology

Figures 1, 7:
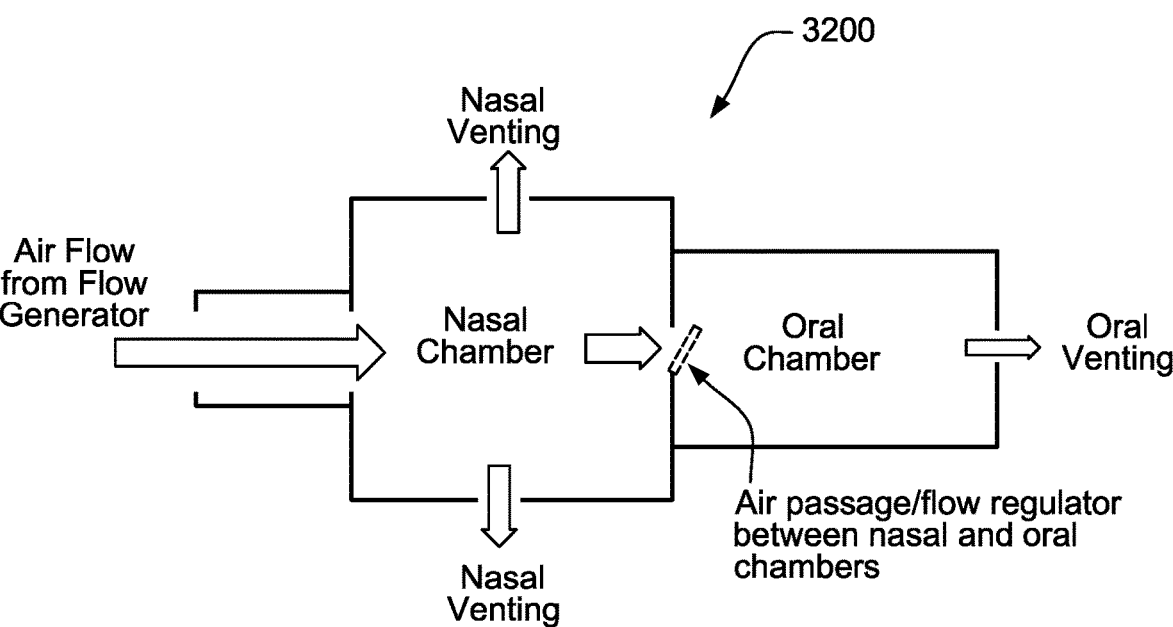

FIG. 7-1 is a schematic representation of a dual chamber cushion assembly according to an examples of the present technology.

Figures 2, 7:
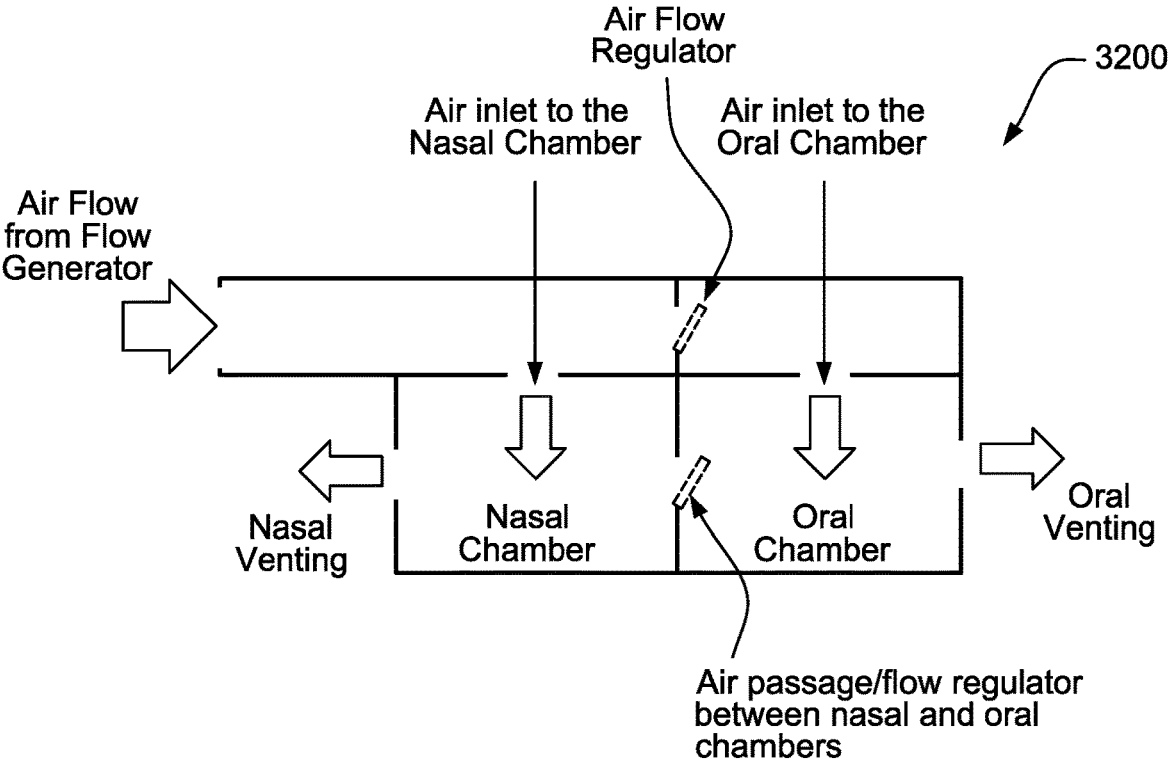

FIG. 7-2 is a schematic representation of a dual chamber cushion assembly according to another example of the disclosed technology.

Figure 8:
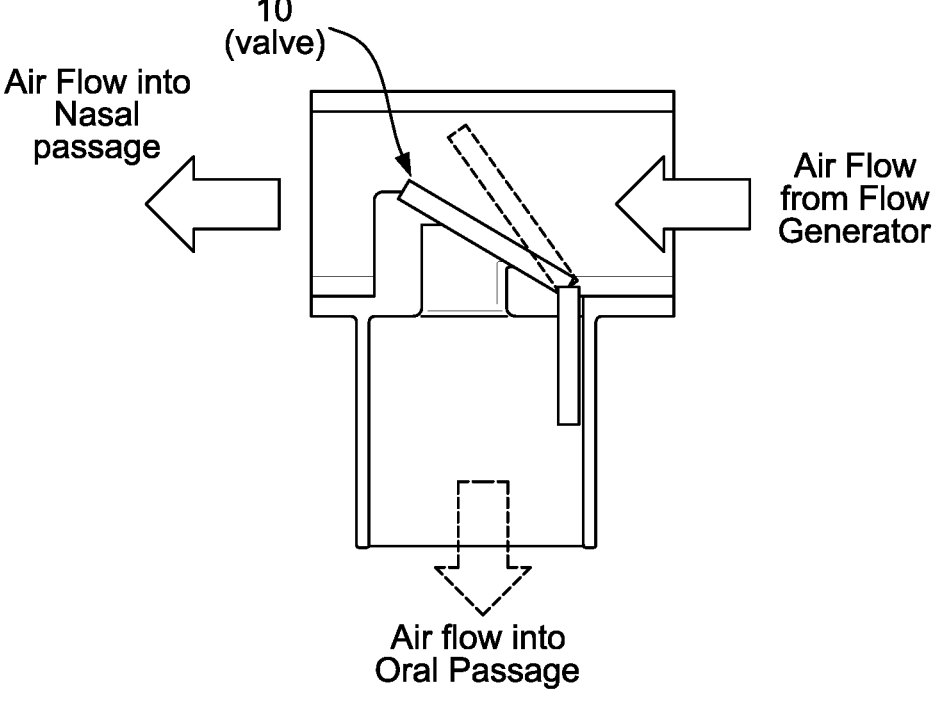

FIG. 8 shows a valve in an air path between a flow generator and the patient's airways according to an example of the present technology.

Figure 9:
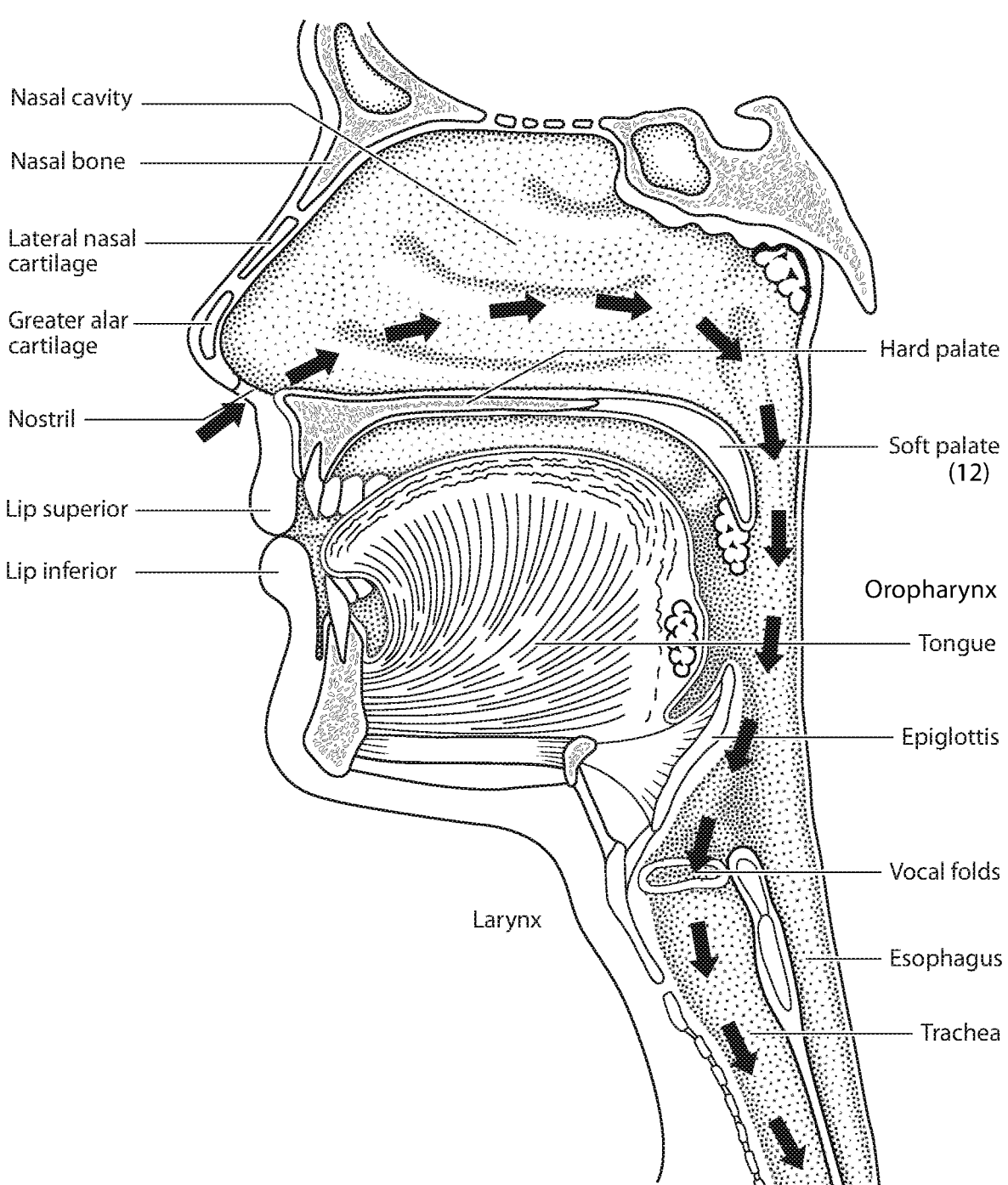

FIG. 9 shows a view of the human upper airway illustrating how the soft palate may be displaced to encourage nasal breathing according to an example of the present technology.

Figure 10:
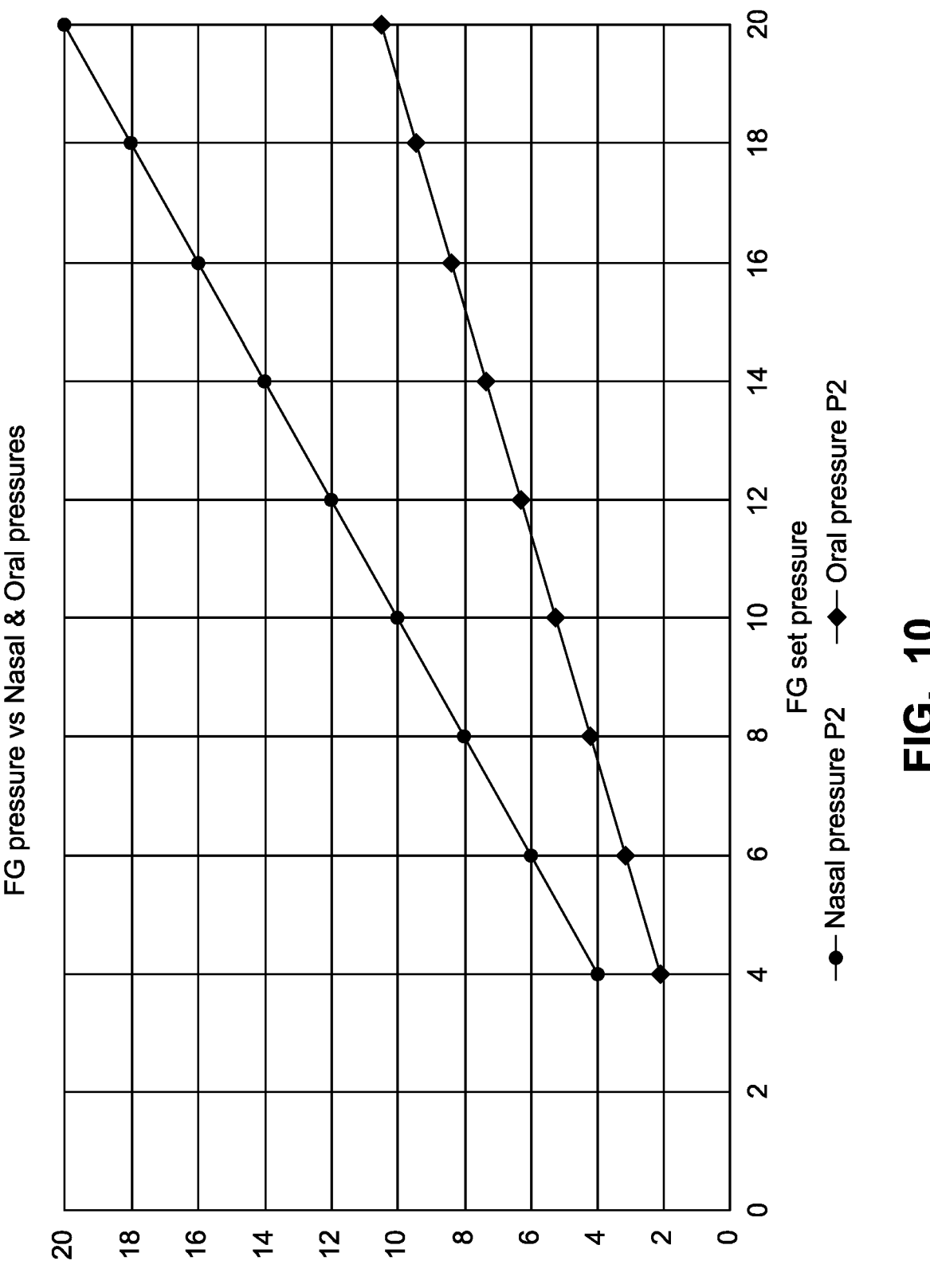

FIG. 10 is a graph showing an example of flow generator set pressures in comparison to the pressures provided in the nasal and oral chambers of the patient interface according to an example of the present technology.

Figure 11:
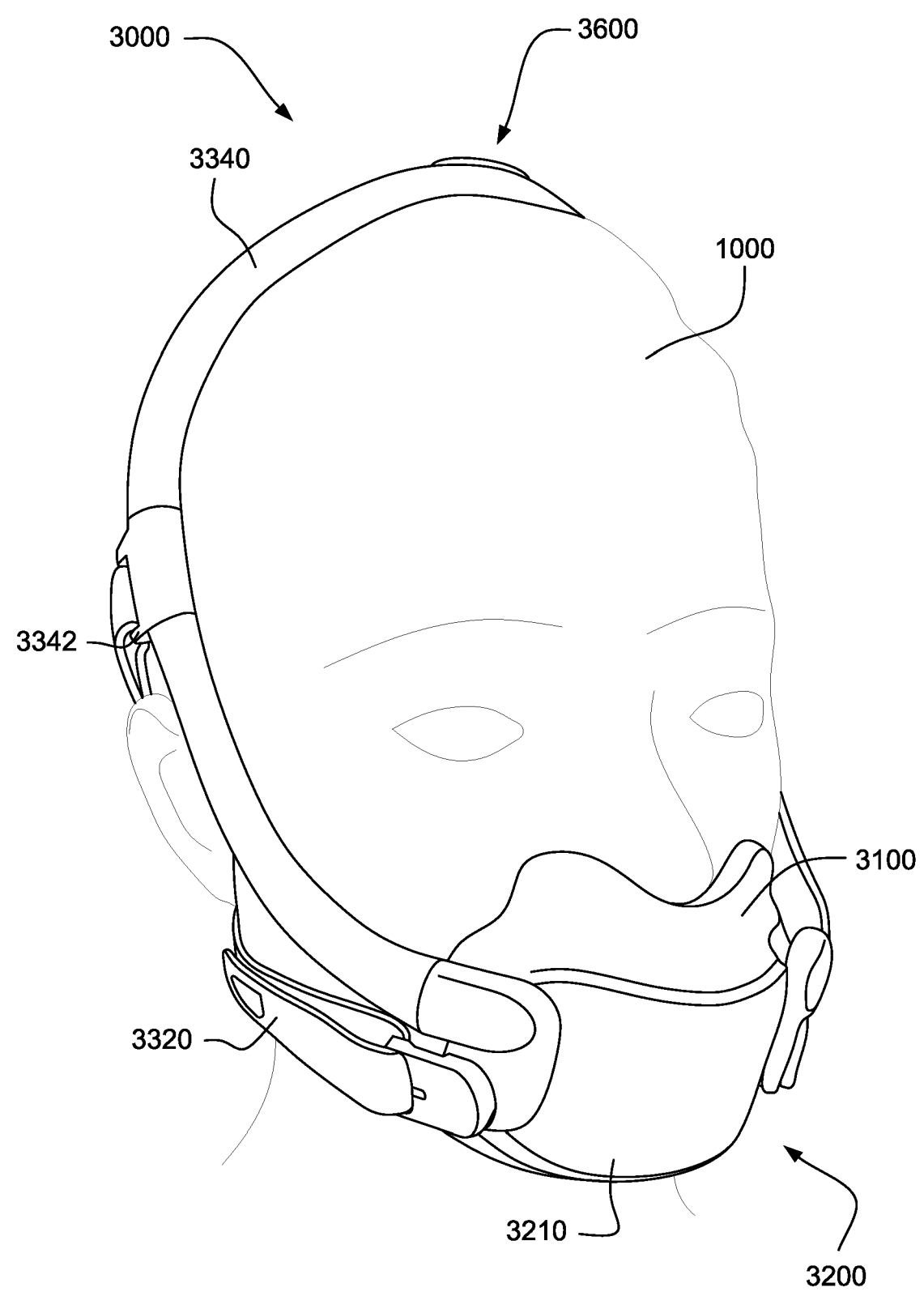

FIG. 11 shows a patient interface being worn by a patient in accordance with an example of the present technology.

Figure 12:
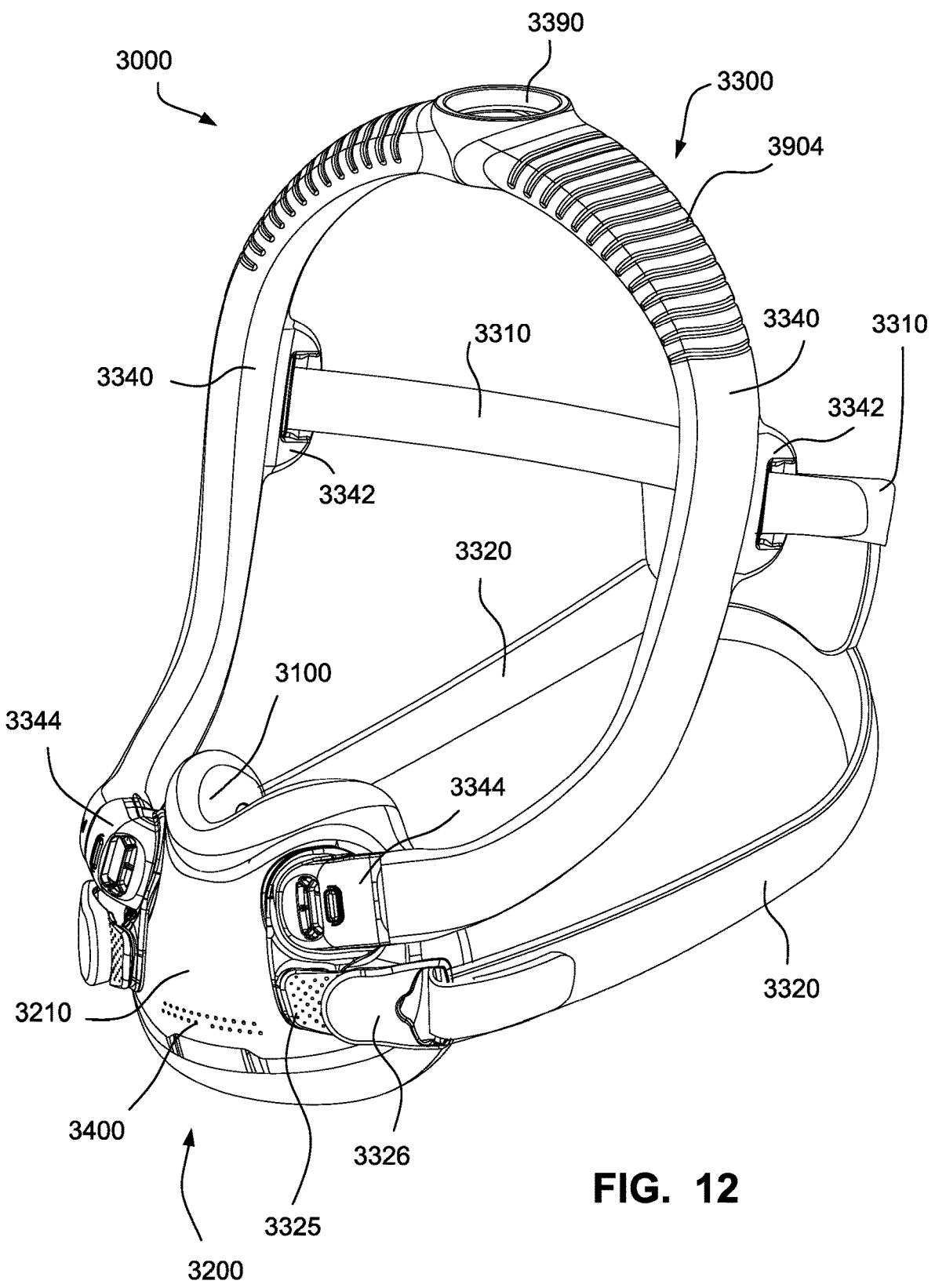

FIG. 12 is a perspective view of a patient interface according to another example of the present technology.

Figures 13, 14:
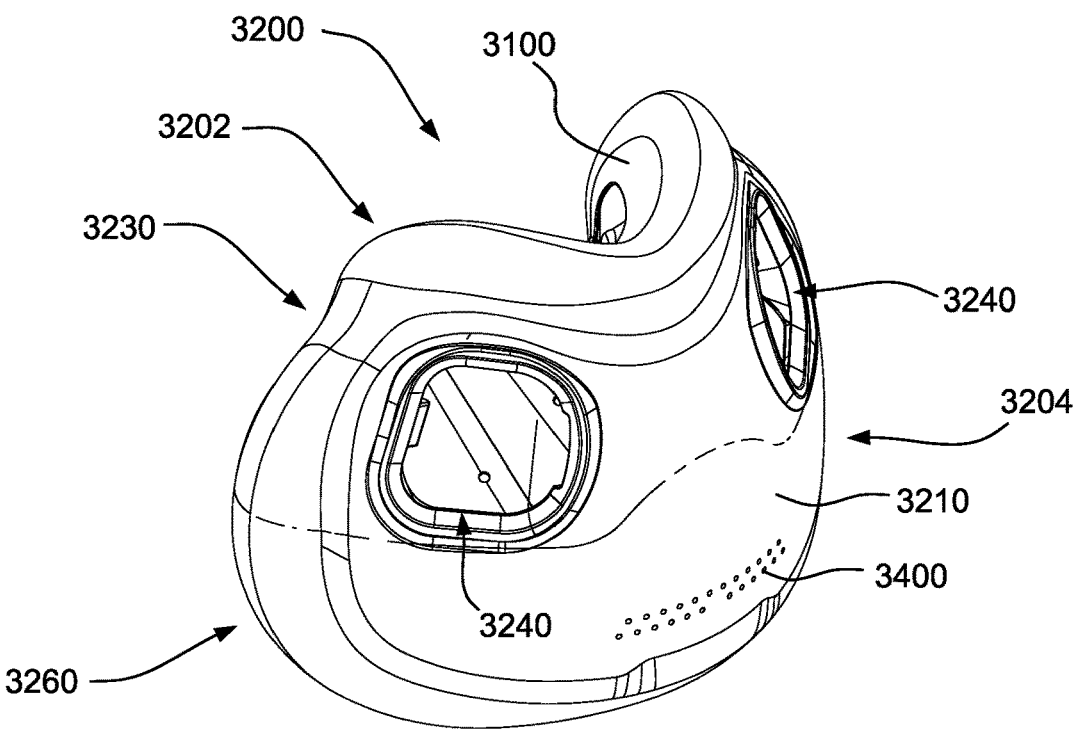

FIG. 13 is a perspective view of the plenum chamber of the patient interface in FIG. 12.

FIG. 14 is a rear view of the plenum chamber of FIG. 13.

Figures 1, 15:
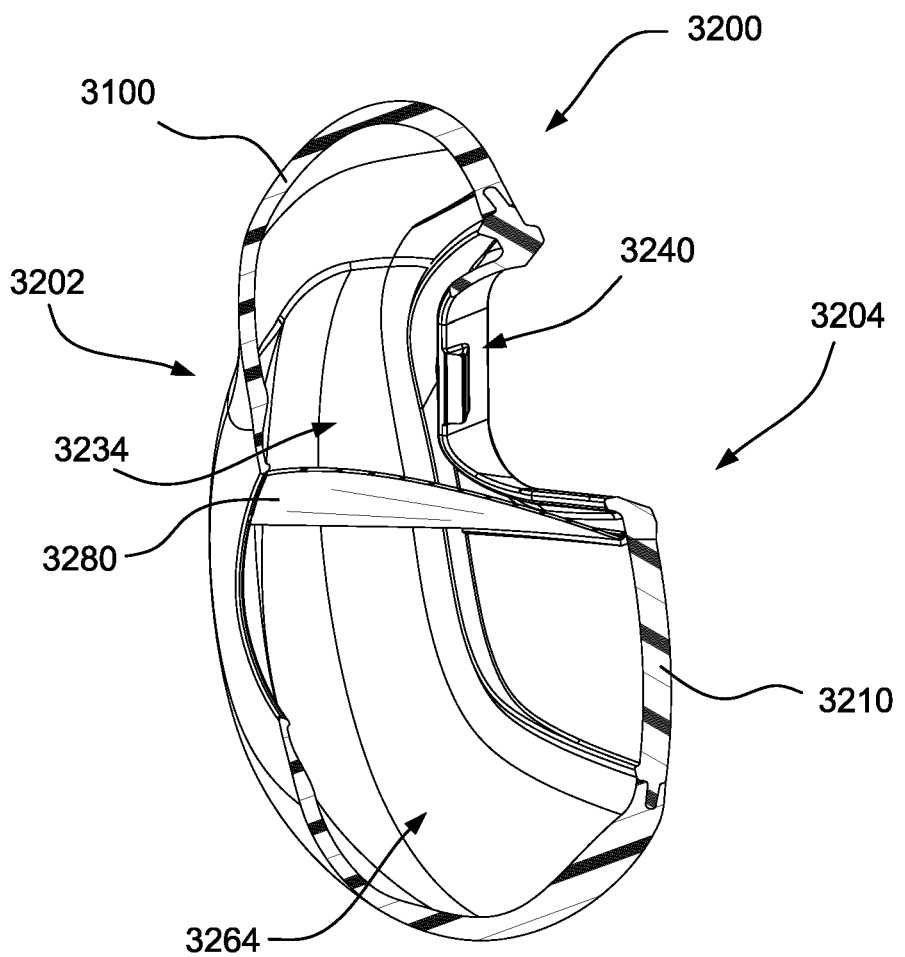

FIG. 15-1 is a cross-sectional view along the line 15-1-15-1 in FIG. 14.

FIG. 15-2 is a cross-sectional view along the line 15-2-15-2 in FIG. 14.

FIG. 15-2A is an enlarged view of a portion of the plenum chamber from FIG. 15-2.

FIG. 15-2B is an enlarged view of a portion of a plenum chamber according to another example of the present technology.

Figures 3, 15:
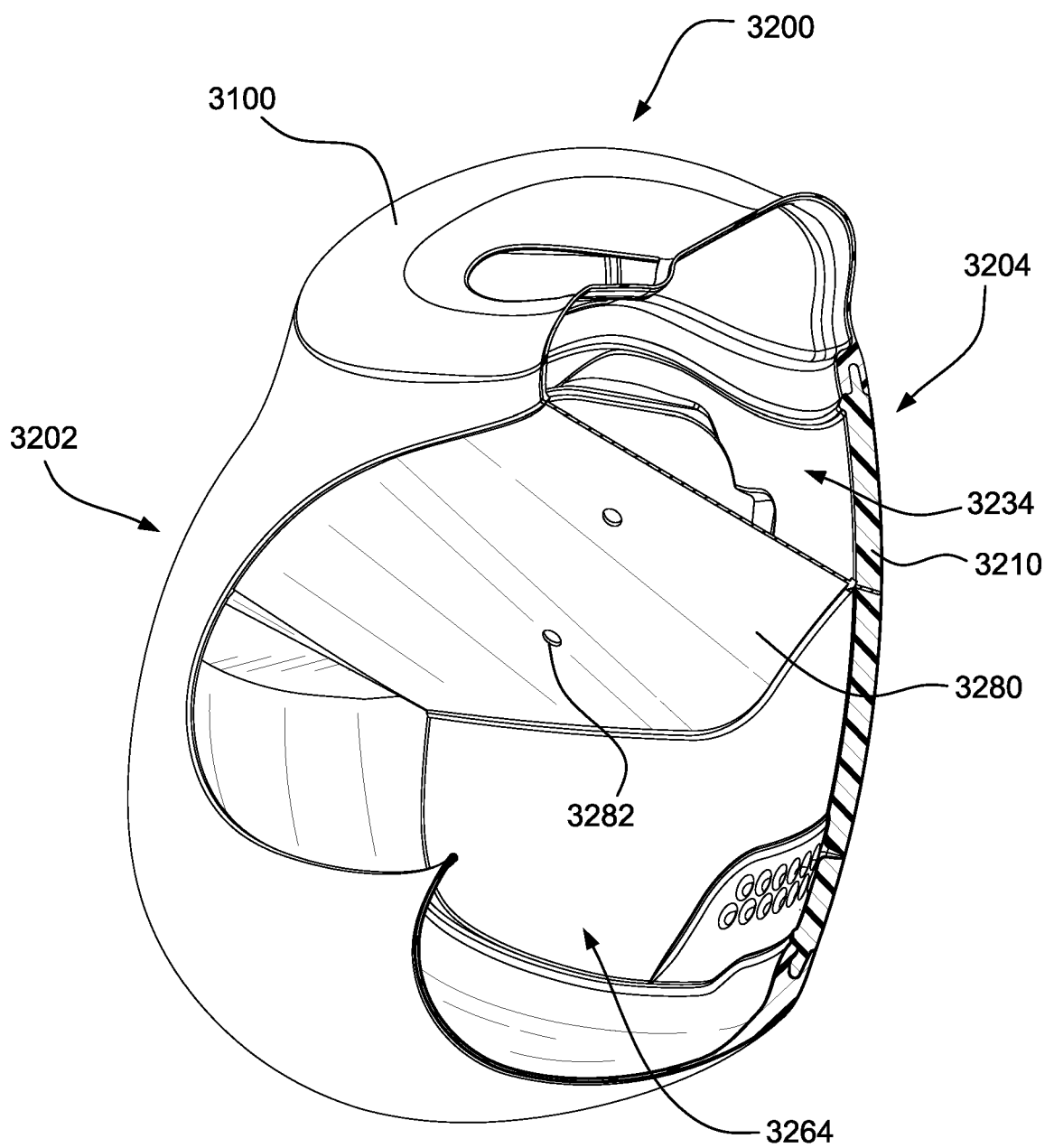

FIG. 15-3 is a cross-sectional view along the line 15-3-15-3 in FIG. 14.

Figures 4, 15:
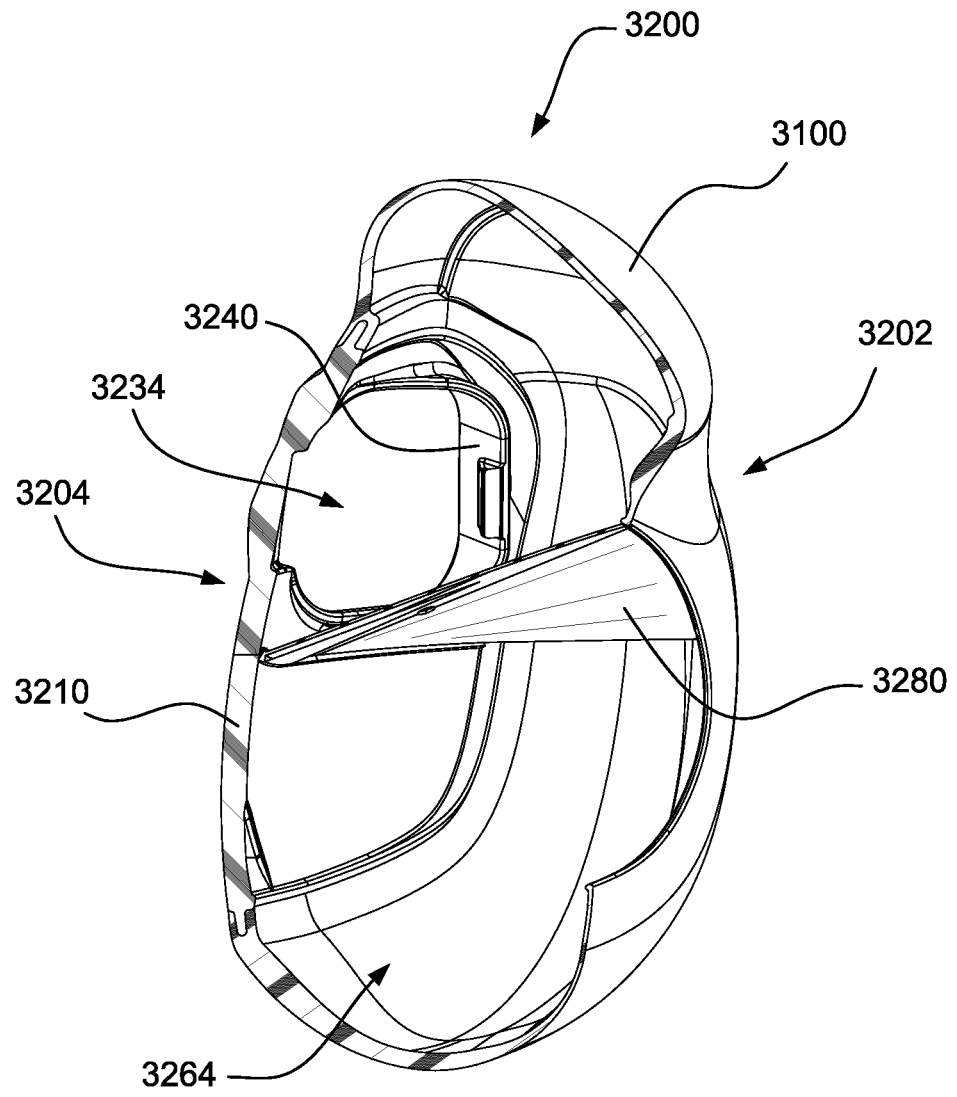

FIG. 15-4 is a cross-sectional view along the line 15-4-15-4 in FIG. 14.

Figure 16:
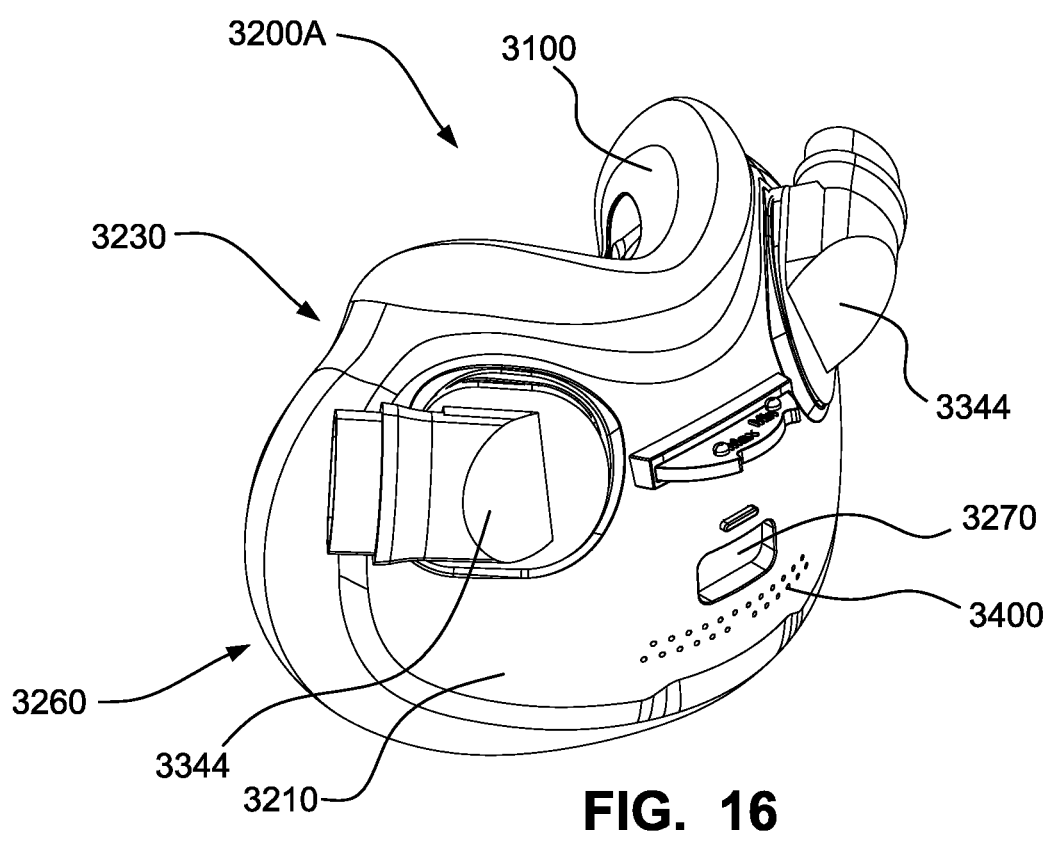

FIG. 16 is a perspective view of a plenum chamber according to another example of the present technology.

Figures 1, 17:
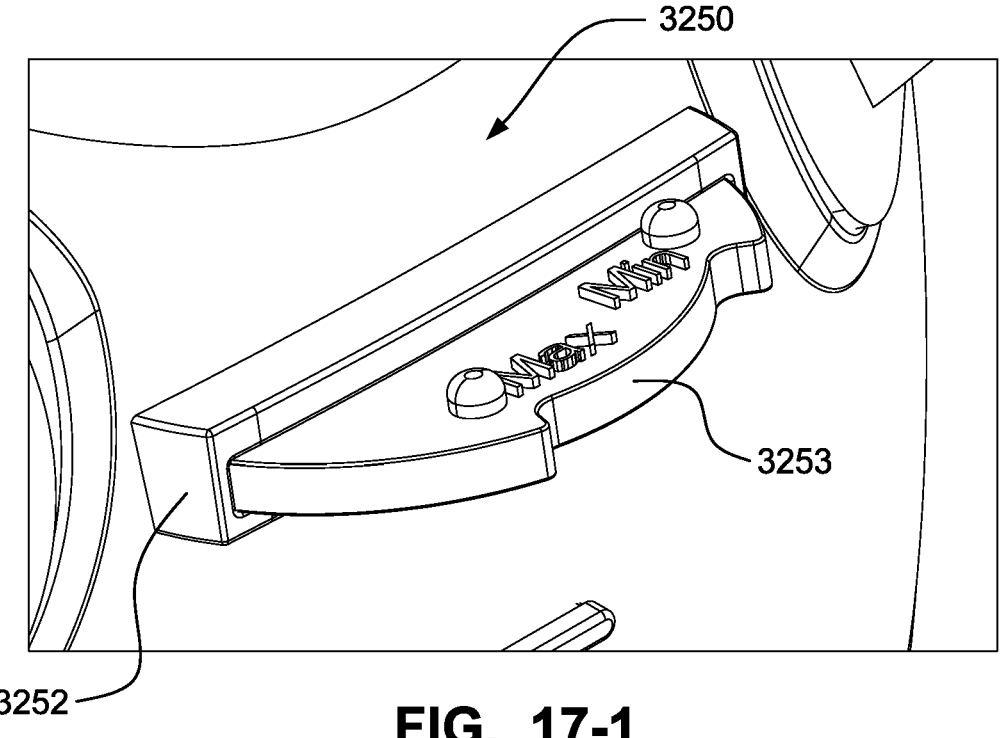
Figures 2, 17:
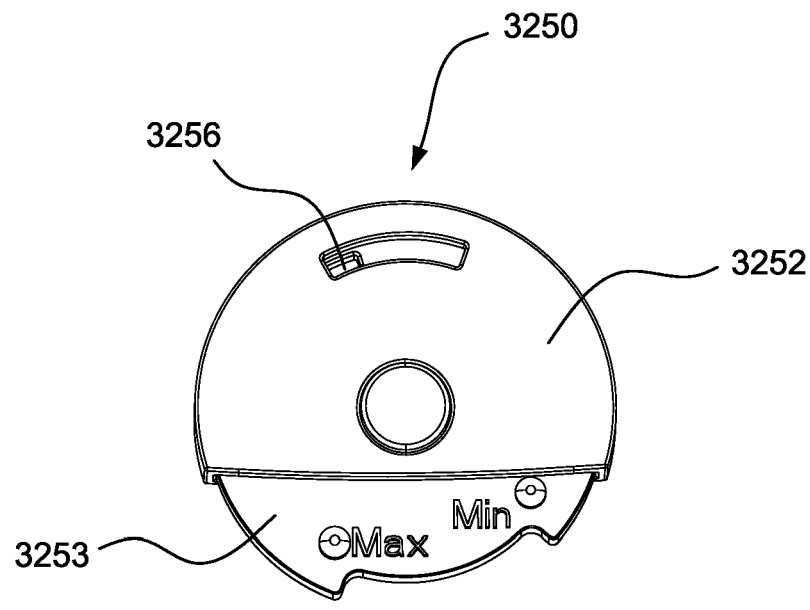
Figures 3, 17:
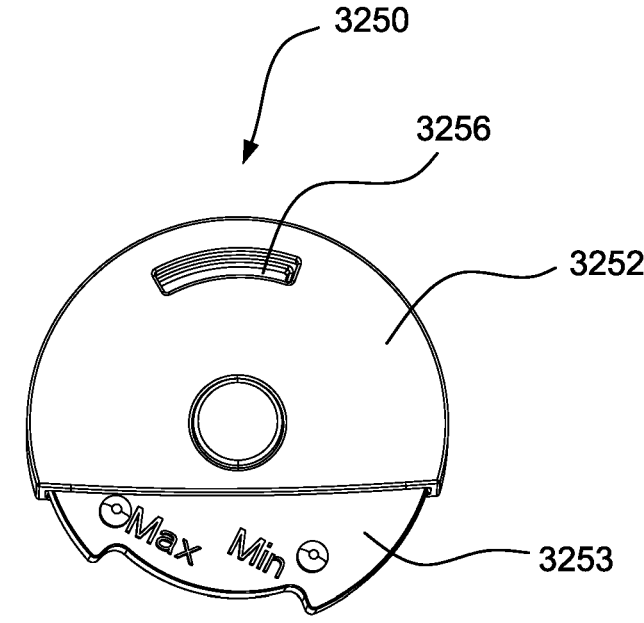

FIG. 17-1 is an enlarged view of a portion of the plenum chamber from FIG. 16 showing a regulator valve according to an example of the present technology.

FIGS. 17-2 and 17-3 are top view of a regulator valve according to examples of the present technology.

Figure 18:
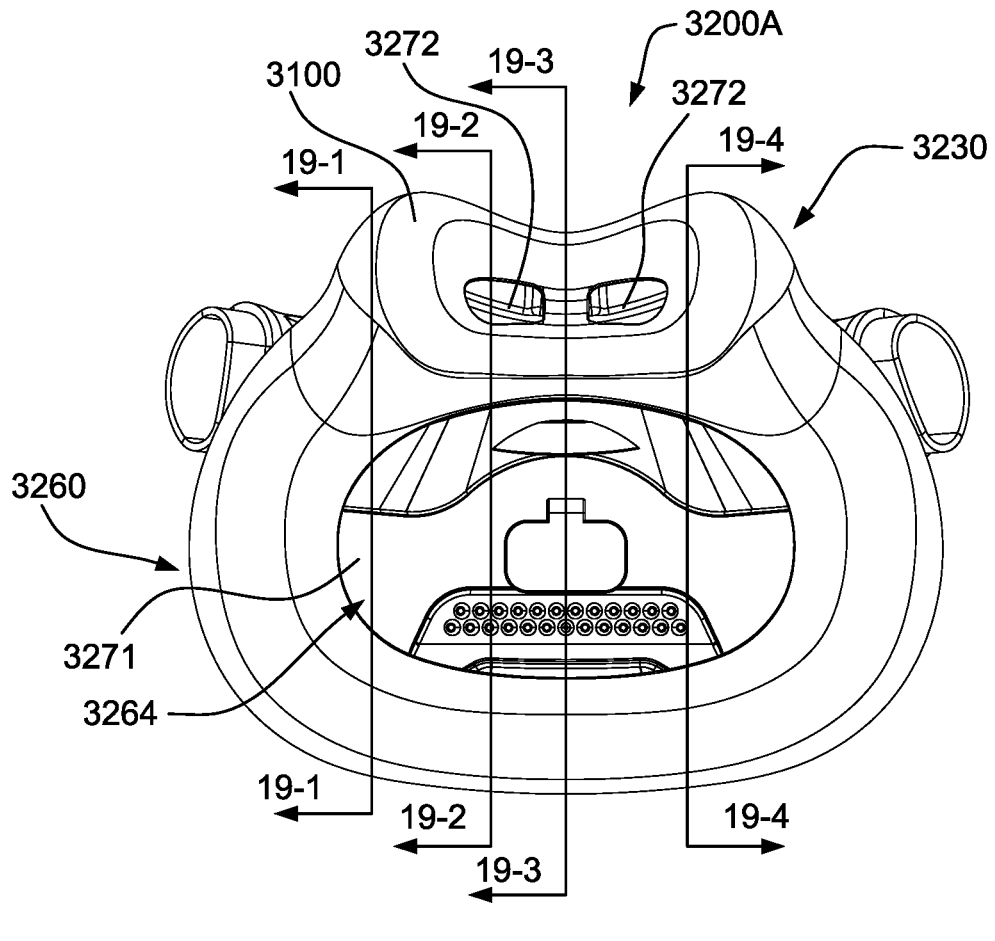

FIG. 18 is a rear view of the plenum chamber of FIG. 16.

Figures 1, 19:
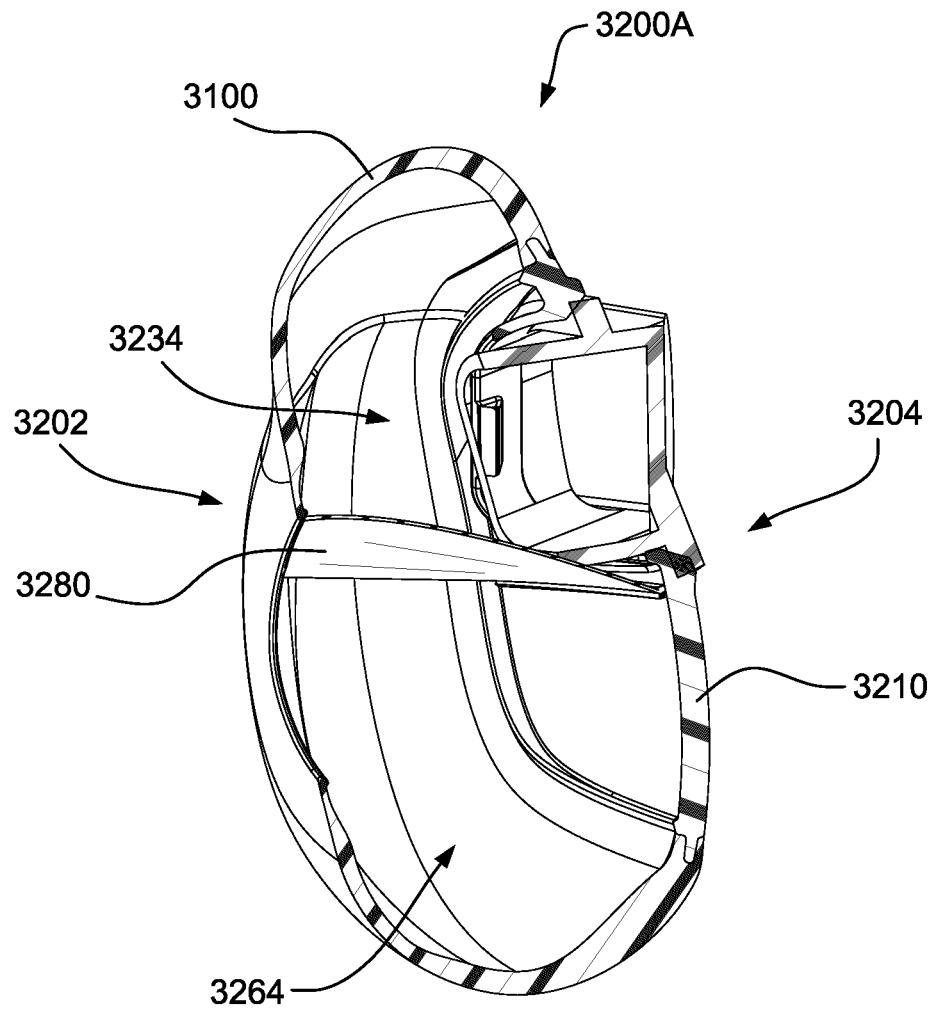
Figures 2, 19:
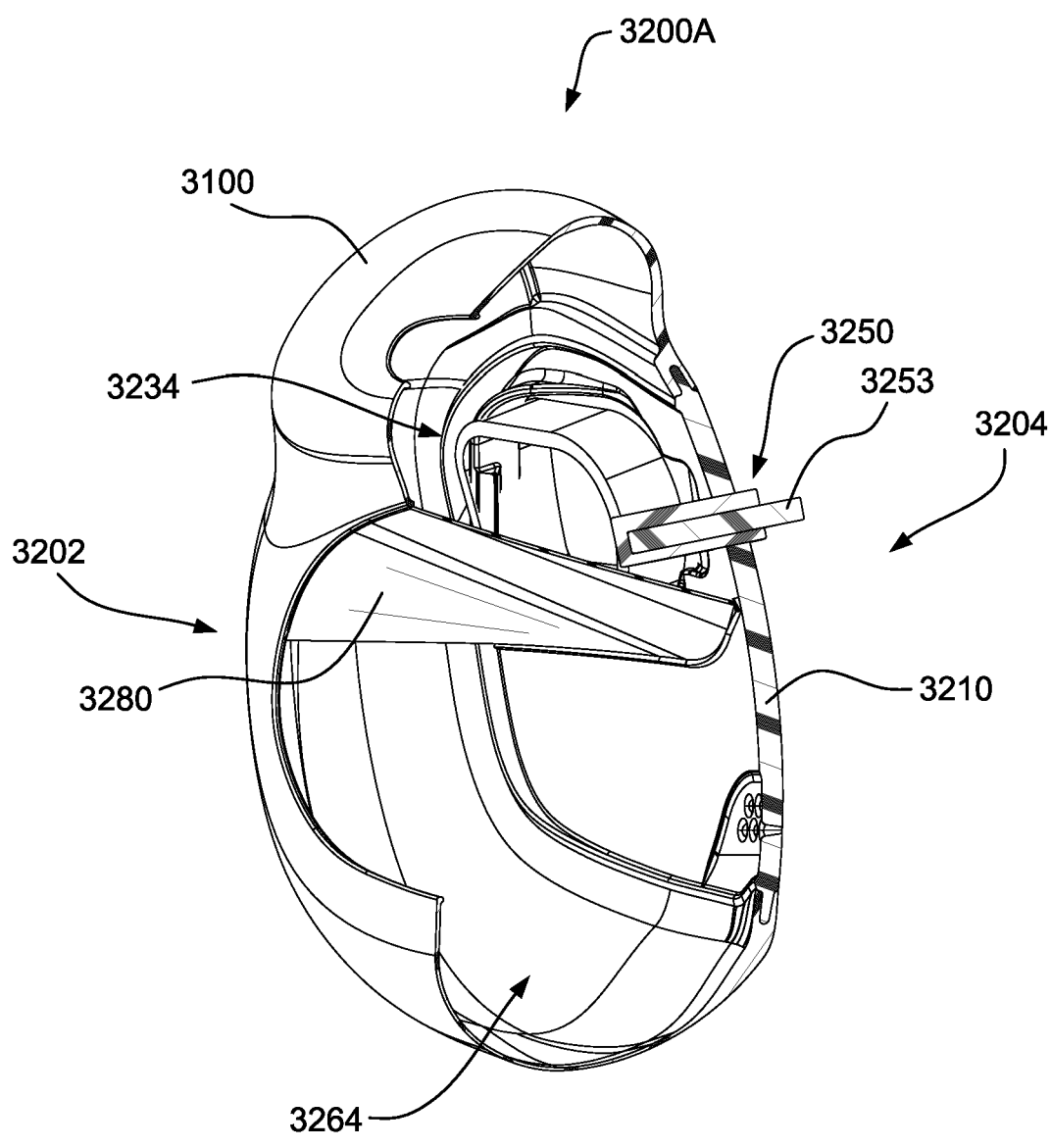
Figures 3, 19:
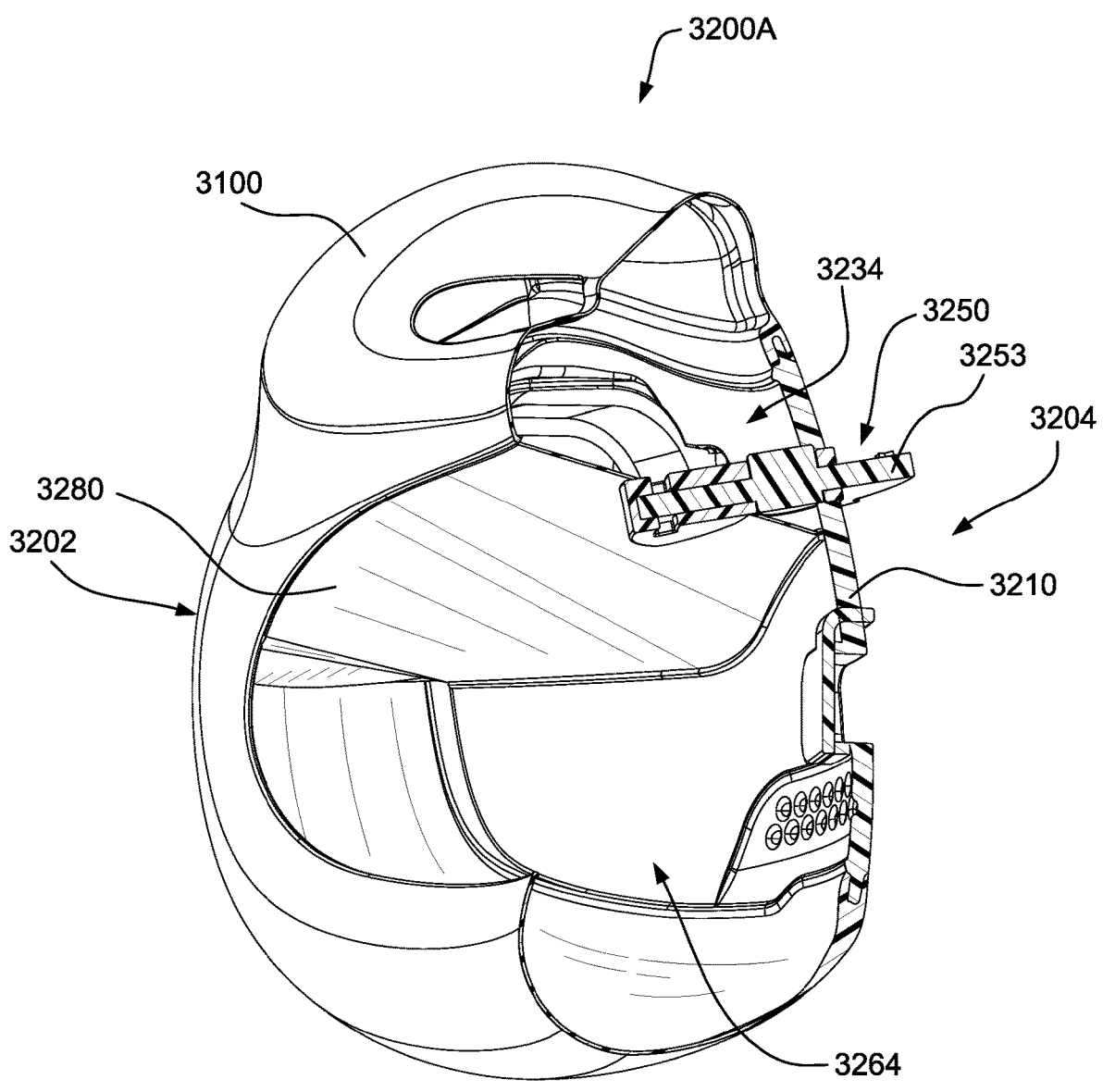
Figures 4, 19:
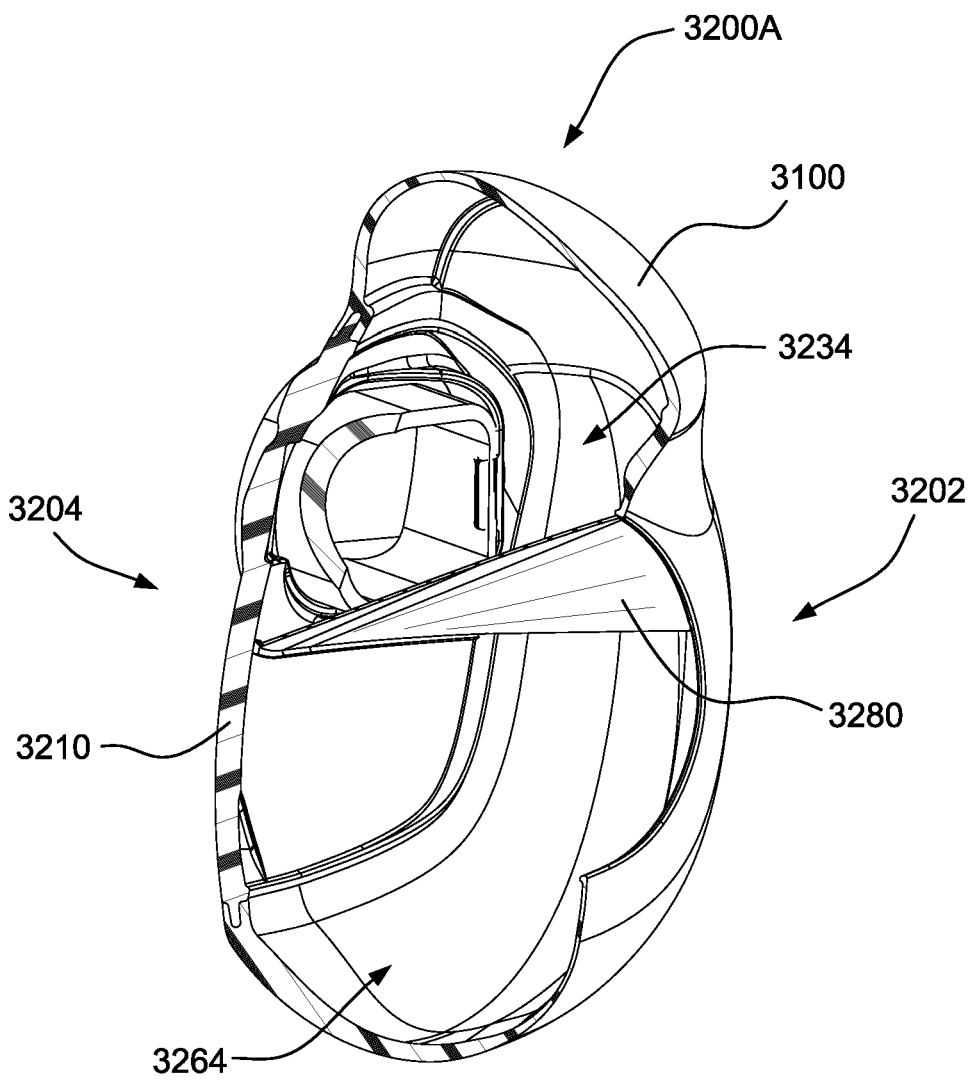

FIG. 19-1 is a cross-sectional view along the line 19-1-19-1 in FIG. 18.

FIG. 19-2 is a cross-sectional view along the line 19-2-19-2 in FIG. 18.

FIG. 19-3 is a cross-sectional view along the line 19-3-19-3 in FIG. 18.

FIG. 19-4 is a cross-sectional view along the line 19-4-19-4 in FIG. 18.

Figure 20:
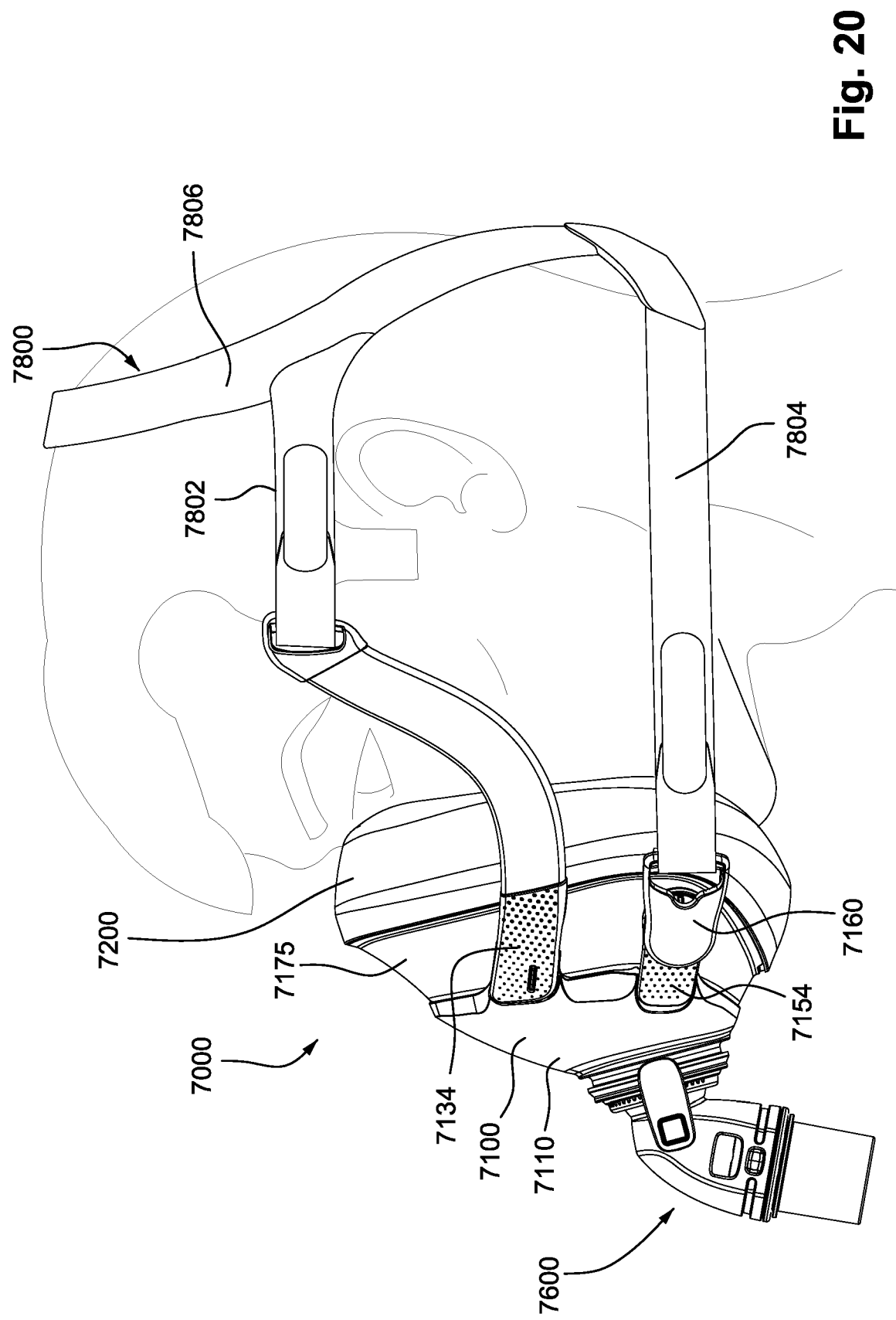

FIG. 20 shows a patient interface being worn by a patient in accordance with another example of the present technology.

Figure 21:
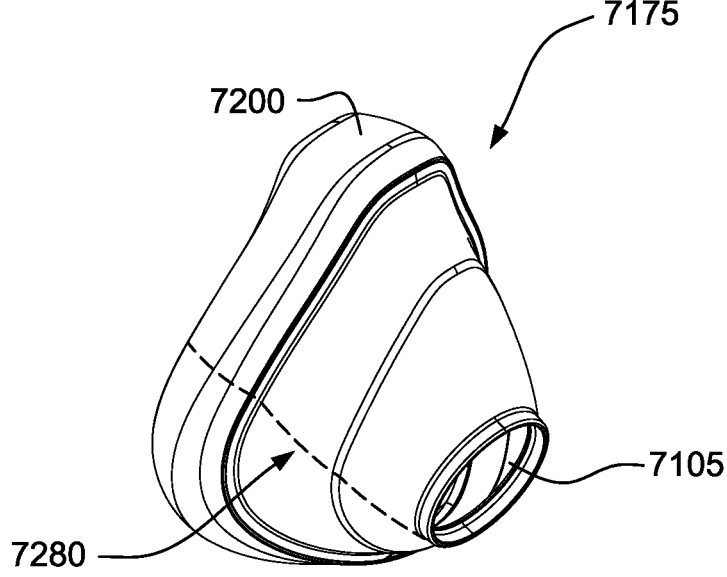

FIG. 21 is a perspective view of the cushion assembly of the patient interface in FIG. 20.

Figure 22:
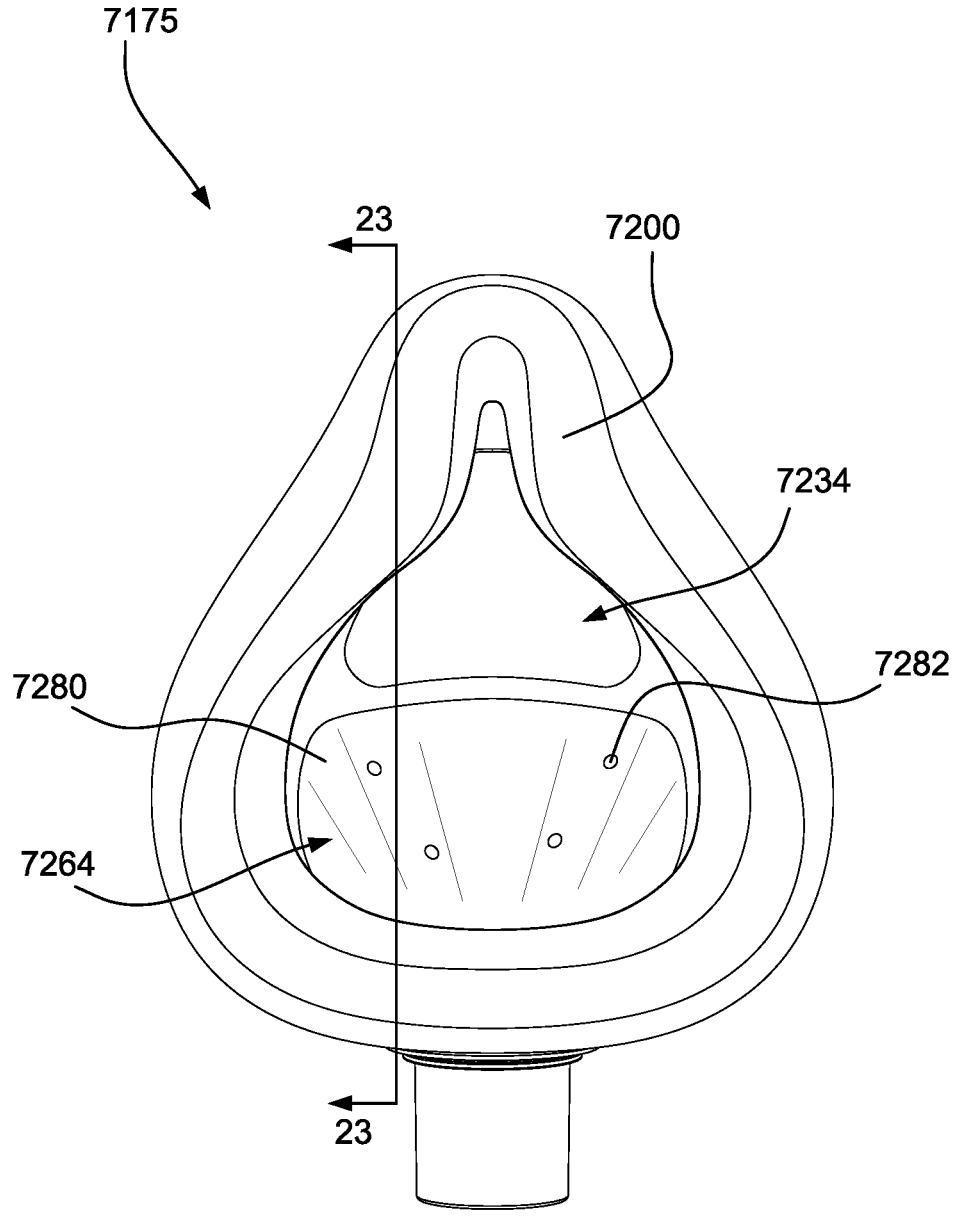

FIG. 22 is a rear view of the cushion assembly of FIG. 21.

Figure 23:
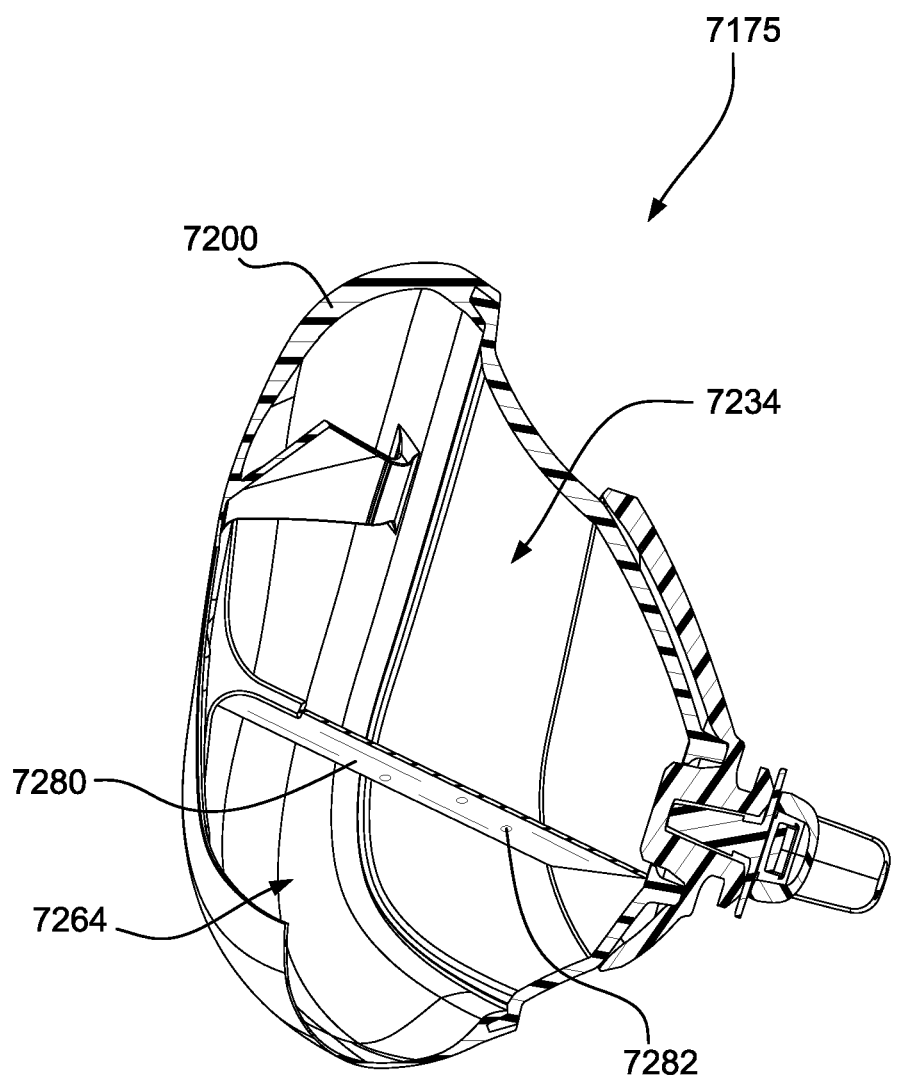

FIG. 23 is a cross-sectional view along the line 23-1-23-1 in FIG. 22.

Figure 24:
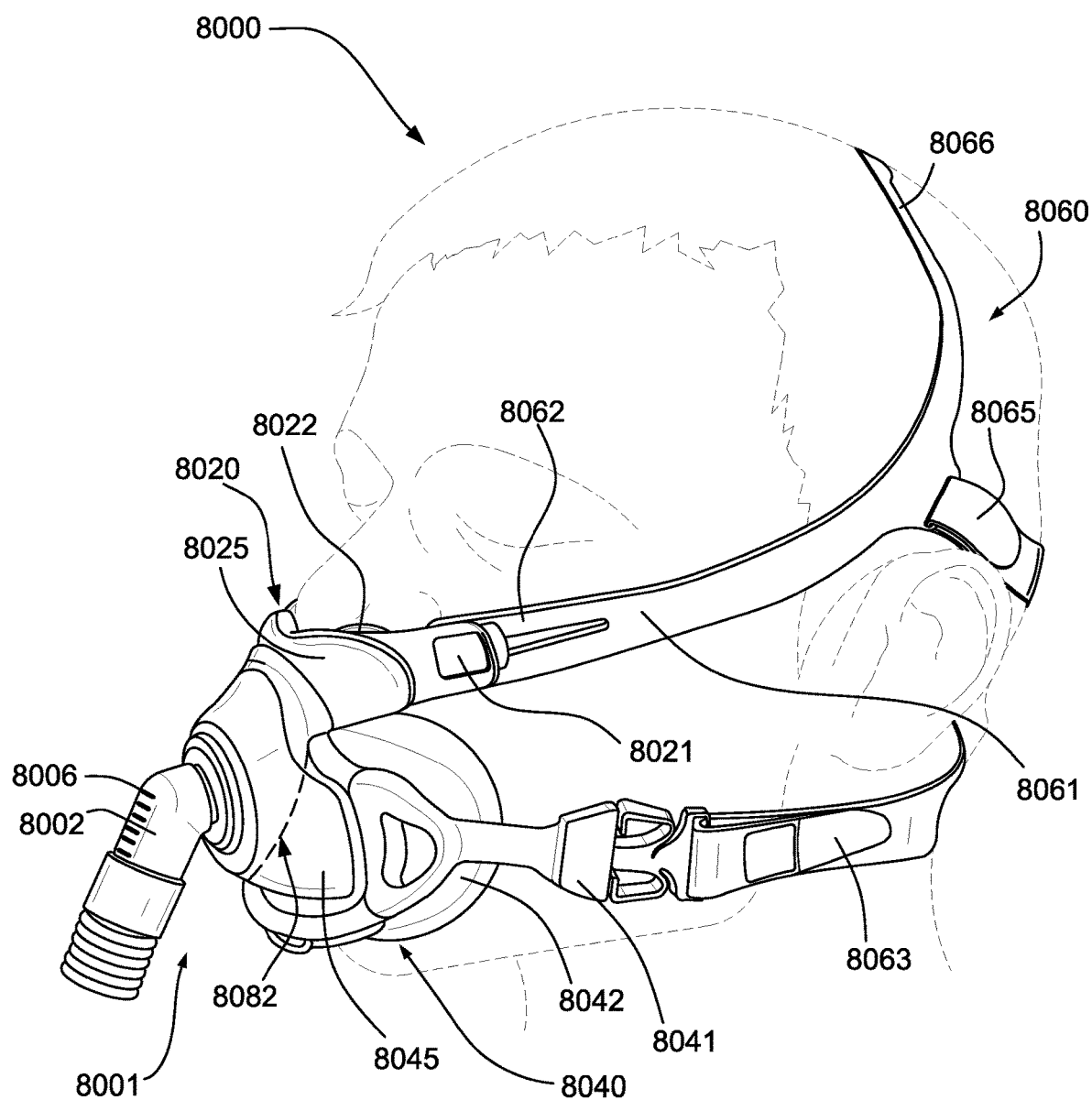

FIG. 24 shows a patient interface being worn by a patient in accordance with another example of the present technology.

Figure 25:
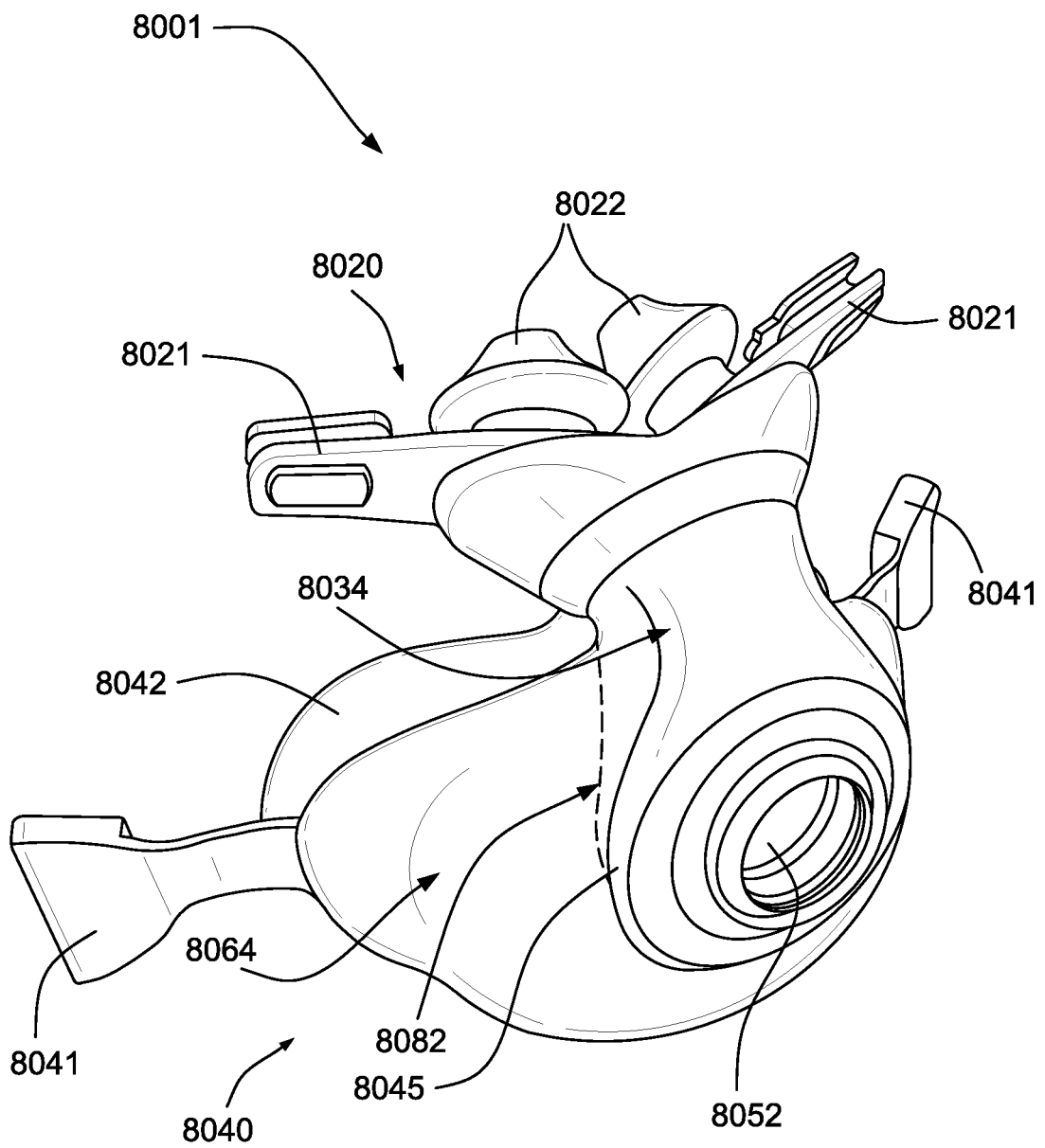

FIG. 25 is a perspective view of the cushion assembly of the patient interface in FIG. 24.

Figure 26:
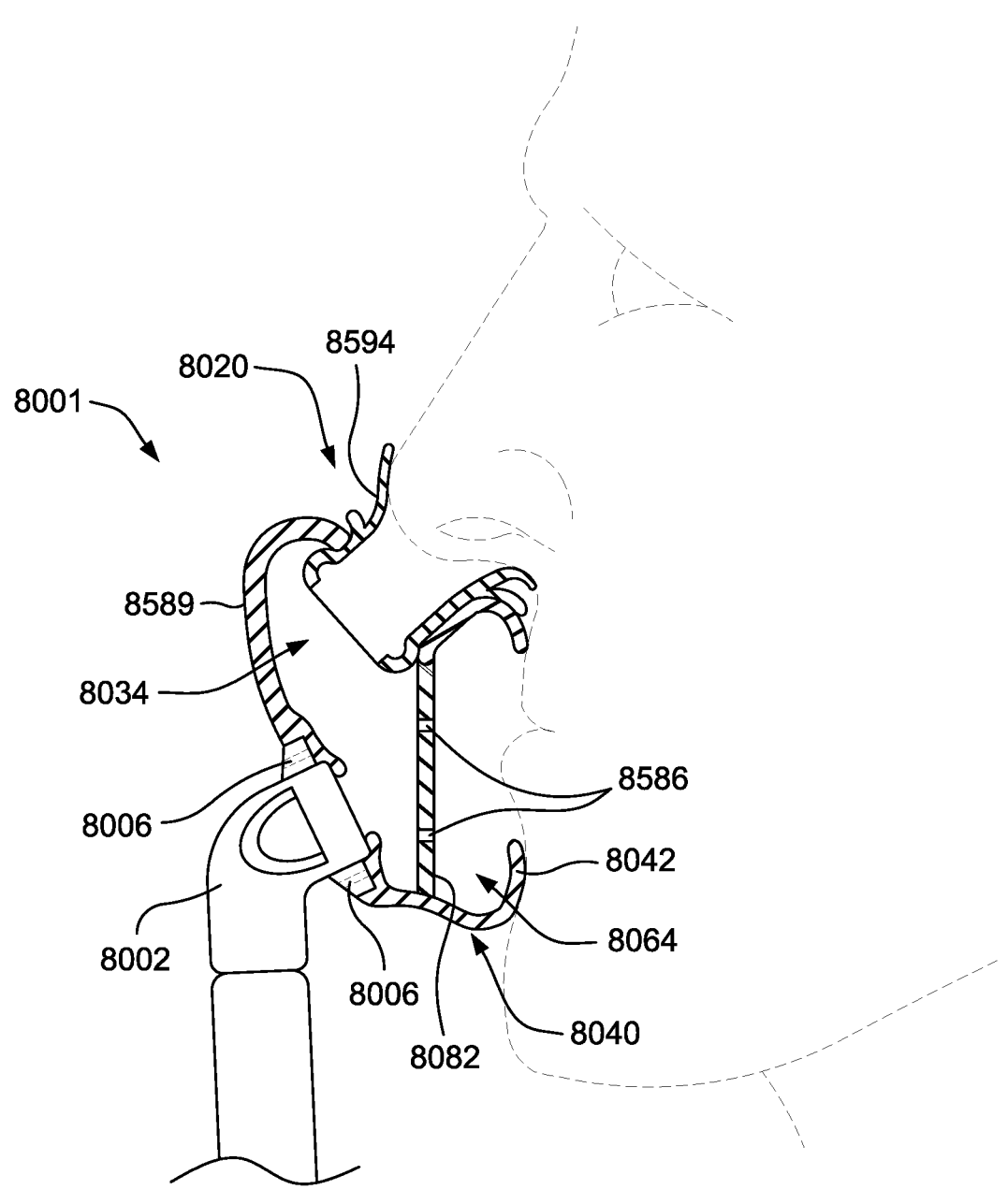

FIG. 26 is a partial cross-sectional view showing a patient interface being worn by a patient in accordance with another example of the present technology.

Figure 27:
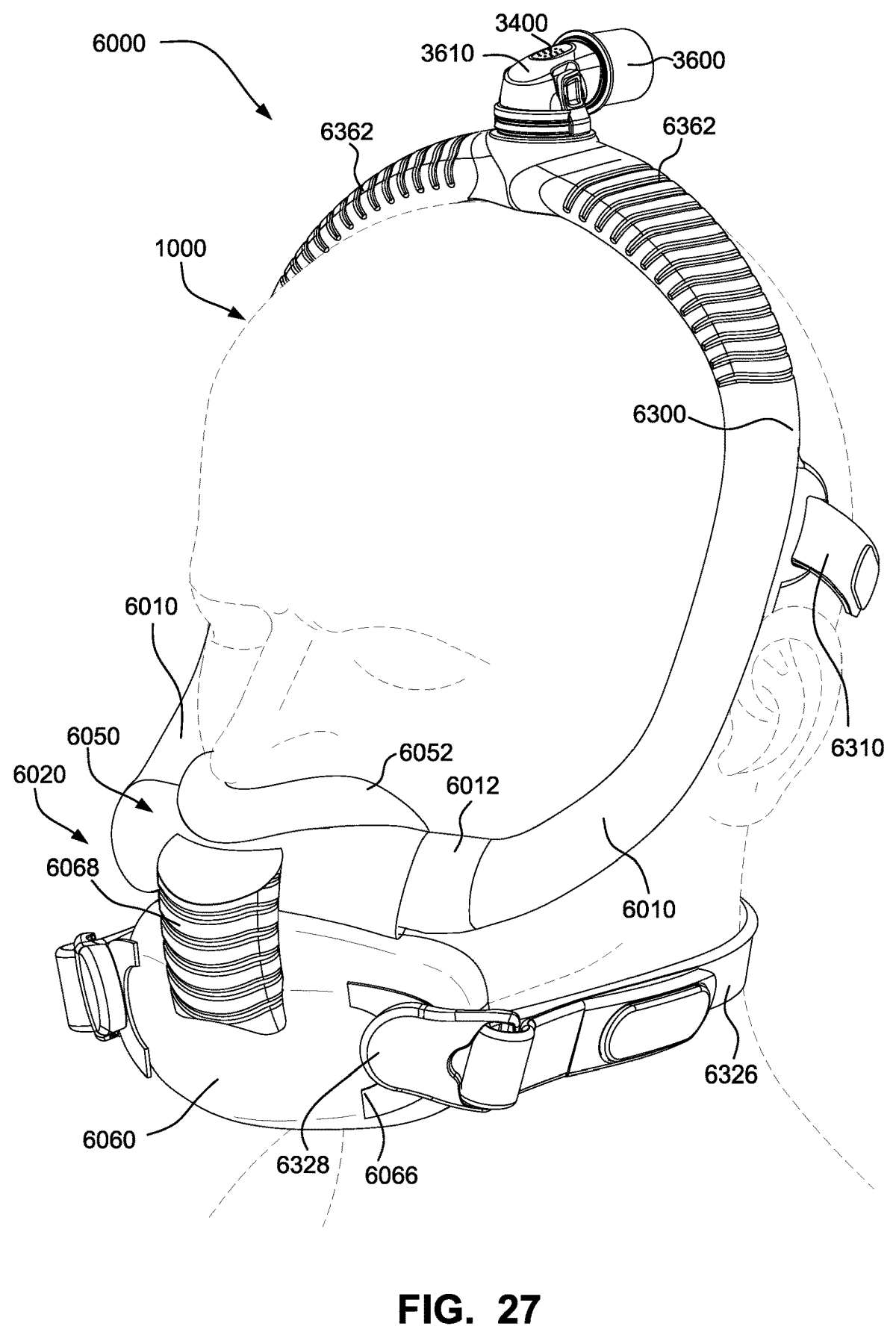

FIG. 27 shows a patient interface being worn by a patient in accordance with another example of the present technology.

Figure 28:
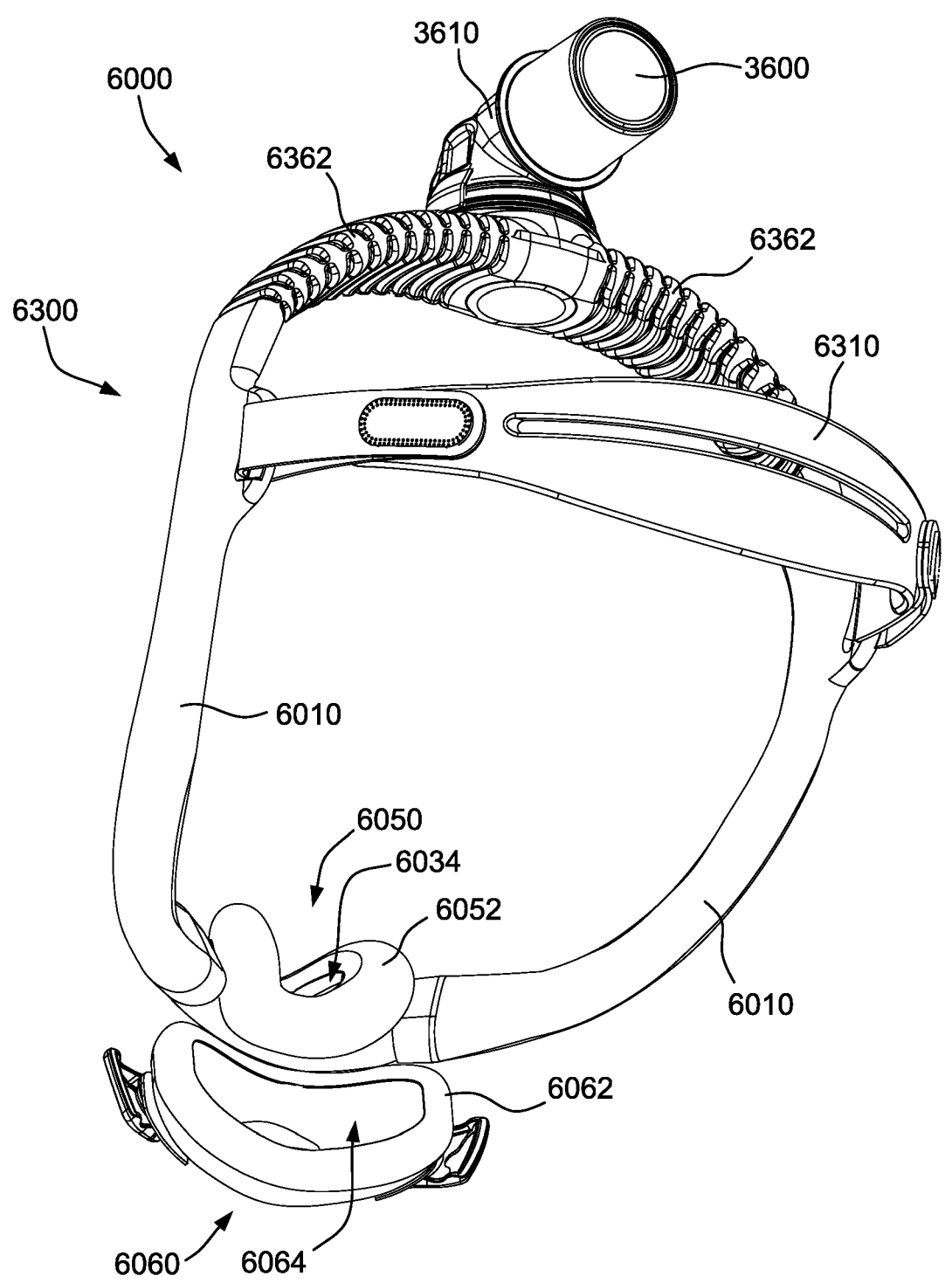

FIG. 28 is a rear perspective view of the patient interface of FIG. 27.

Figure 29:
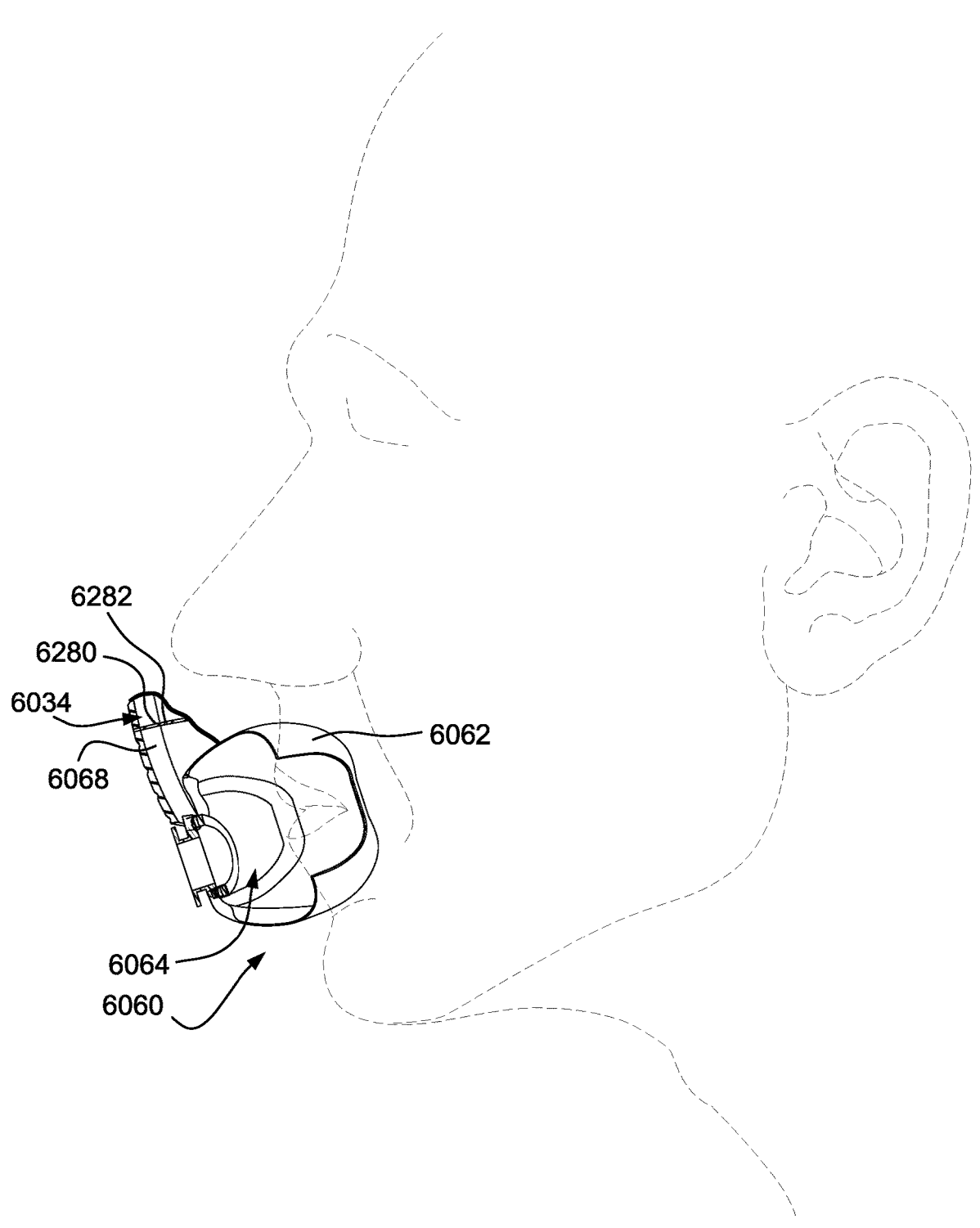

FIG. 29 is a partial cross-sectional view showing the patient interface of FIG. 27 being worn by a patient.

Figure 30:
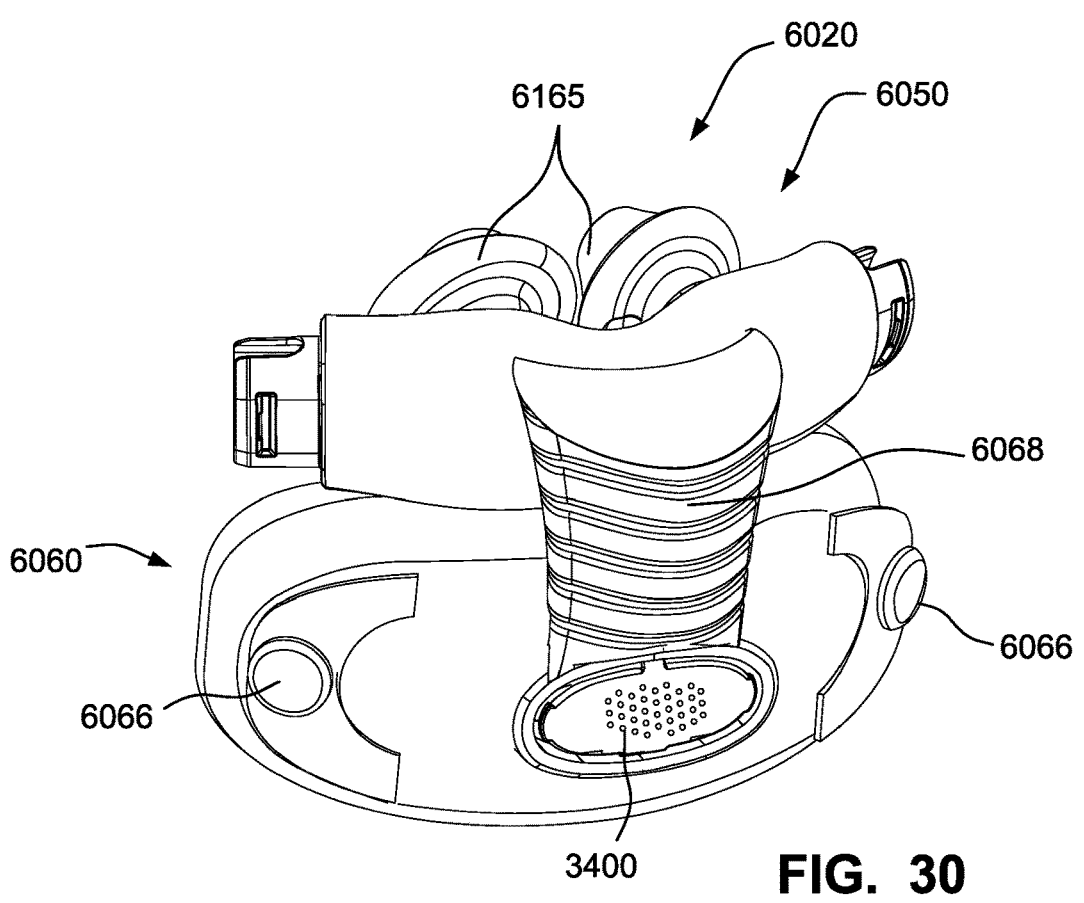

FIG. 30 is a front perspective view of a cushion assembly in accordance with another example of the present technology.

Figure 31:
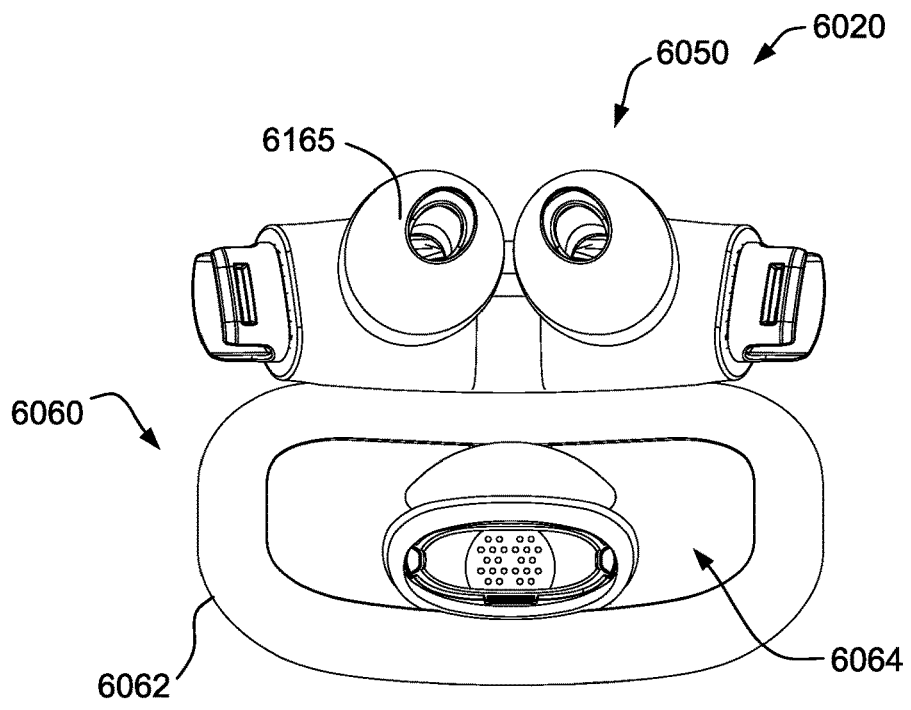

FIG. 31 is rear perspective view of the cushion assembly of FIG. 30.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000 or 3800.

5.3 Patient Interface

Referring, for example, to FIGS. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

In some examples of the present technology (e.g., FIG. 12), the plenum chamber 3200 is at least partially formed by a shell 3210 and the seal-forming structure 3100. The plenum chamber 3200 may comprise or be referred to as a cushion module or cushion assembly, for example. The shell 3210 may function as a chassis for the seal-forming structure 3100.

An unsealed patient interface 3800, in the form of a nasal cannula, includes nasal prongs 3810*a*, 3810*b* which can deliver air to respective nares of the patient 1000 via respective orifices in their tips. Such nasal prongs do not generally form a seal with the inner or outer skin surface of the nares. This type of interface results in one or more gaps that are present in use by design (intentional) but they are typically not fixed in size such that they may vary unpredictably by movement during use. This can present a complex pneumatic variable for a respiratory therapy system when pneumatic control and/or assessment is implemented, unlike other types of mask-based respiratory therapy systems. The air to the nasal prongs may be delivered by one or more air supply lumens 3820*a*, 3820*b* that are coupled with the nasal cannula-type unsealed patient interface 3800. The lumens 3820*a*, 3820*b* lead from the nasal cannula-type unsealed patient interface 3800 to a respiratory therapy device via an air circuit. The unsealed patient interface 3800 is particularly suitable for delivery of flow therapies, in which the RPT device generates the flow of air at controlled flow rates rather than controlled pressures. The "vent" or gap at the unsealed patient interface 3800, through which excess airflow escapes to ambient, is the passage between the end of the prongs 3810*a* and 3810*b* of the nasal cannula-type unsealed patient interface 3800 via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material (e.g., silicone).

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

Referring to FIGS. 11 to 19-4, patient interface 3000 may include a cushion assembly (plenum chambers 3200, 3200A) having a seal-forming structure 3100 that is configured to seal separately around the patient's nares and mouth, i.e., an oro-nasal (or full face) cushion assembly. The cushion assemblies shown in FIGS. 11 to 19-4 maybe referred to as ultra-compact full face masks as they seal below or at the pronasale rather than extending over the patient's nose. The seal-forming structure 3100 may include a nasal portion 3230 having a pair of nasal portion holes 3272 to seal with the patient's nares. The seal-forming structure 3100 may include an oral portion 3260 having an oral portion hole 3271 to seal with the patient's mouth.

The plenum chamber 3200 is at least partially formed by a shell 3210 and the seal-forming structure 3100 that is attached to the shell in accordance with examples of the present technology. The seal-forming structure may be oriented on a patient contacting side 3202 of the plenum chamber 3200 and the shell 3210 may be oriented on a non-patient contacting side 3204 of the plenum chamber, as shown for example in FIG. 13. A plurality of vent holes 3400 may be formed in the shell 3210 to discharge exhaust gases. Additionally, an anti-asphyxia valve (AAV) 3270 may be formed in the plenum chamber 3200. The AAV may be configured to open in the absence of pressure within the plenum chamber 3200 in order to allow a flow of air between the interior of the plenum chamber 3200 and ambient.

In some examples the seal-forming structure 3100 is overmoulded to the shell 3210. The seal-forming structure 3100 may alternatively be formed separately from the shell 3210 and be configured to permanently or removably connect to the shell 3210. The seal-forming structure 3100 and shell 3210 may be integrally formed. The plenum chamber may be referred to as a cushion assembly that includes, for example, the shell and the seal-forming structure.

In examples, the shell 3210 may be formed from polycarbonate and the seal-forming structure 3100 may be formed from silicone. The silicone may have a Shore A hardness of 30 or 40 Durometer. A silicone or similar material with this hardness is advantageous for comfort and flexibility to conform and seal to the patient's face. The use of polycarbonate (or other stiffer material), with its higher hardness and stiffness than silicone is advantageous in providing portions of higher resistance to deformation with less material than would be required to provide the same resistance with silicone. The seal-forming structure 3100 may alternatively be formed from a suitable foam or any suitable thermoplastic elastomer.

The cushion assembly (e.g., shell 3210) may comprise one or more plenum chamber inlet ports 3240. In the illustrated examples, e.g., FIG. 13, the plenum chamber 3200 comprises two inlet ports 3240. The inlet ports 3240 are provided to lateral sides of the shell 3210. The inlet ports 3240 in these examples are configured to connect to conduits which connect to a decoupling component located above the patient's head where the conduits are connected to the air circuit. The conduits may form part of the positioning and stabilising structure 3300, i.e., they may be "headgear conduits." In other examples, the plenum chamber 3200 may comprise a single inlet port (e.g., provided centrally in the shell 3210.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

The patient interface 3000 according to examples of the present technology may include conduits (e.g., headgear tubes 3340) to provide the flow of pressurized air from a connection port 3600 to the plenum chamber 3200, as shown in FIGS. 11 and 12. The headgear tubes 3340 may be joined superior to the patient's head and may pass along lateral sides of the patient's head between corresponding ones of the patient's eyes and ears. The headgear tubes 3340 may be connected to the plenum chamber 3200 via headgear tube connectors 3344 (FIG. 16), to provide the flow of pressurized air to the plenum chamber, as shown in FIG. 12. The headgear tubes 3340 may include an expandable concertina section 3904 (e.g., including one or more folding portions, pleats, corrugations or bellows to form a flexible and length extendable portion of the headgear conduits).

The positioning and stabilising structure 3300 comprises a conduit headgear inlet 3390 at the junction of the two headgear tubes 3340, as shown in FIG. 12. The conduit headgear inlet 3390 is configured to receive a pressurised flow of gas, for example via a swivel elbow comprising the connection port 3600, and allow the flow of gas into hollow interiors of the headgear tubes 3340.

The positioning and stabilising structure 3300 may comprise one or more straps in addition to the headgear tubes 3340, as shown in FIG. 12. In an example, the positioning and stabilising structure 3300 comprises a pair of upper straps 3310 and a pair of lower straps 3320. The posterior ends of the upper straps 3310 and lower straps 3320 are joined together. The junction between the upper straps 3310 and lower strap 3320 is configured to lie against a posterior surface of the patient's head in use, providing an anchor for the upper strap 3310 and lower straps 3320. Anterior ends of the upper straps 3310 connect to the headgear tubes 3340. In this example, each headgear tube 3340 comprises a tab 3342 having an opening through which a respective upper strap 3310 can be passed through and then looped back and secured onto itself to secure the upper headgear strap 3310 to the headgear tube 3340. The positioning and stabilising structure 3300 also comprises a lower strap clip 3326 provided to the anterior end of each of the lower straps 3320. Each of the lower strap clips 3326 is configured to connect to a lower connection point 3325 on the plenum chamber 3200. In this example, the lower strap clips 3326 are secured magnetically to the lower connection points 3325. In some examples, there is also a mechanical engagement between the lower strap clips 3326 and the lower connection points 3325.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example, the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. Suitable for a small sized head, but not a large sized head.

5.3.4 Dual Chamber Cushion Assembly

The dual chamber cushion assembly according to examples of the present technology may promote and increase nasal breathing of a patient during treatment for sleep disordered breathing such as sleep apnea. There are numerous benefits associated with breathing primarily through the nasal passageway versus breathing through the oral passageway.

For example, the nose acts as a filter and retains small particles in the air, including pollen. Further, the nose may add moisture to the air inhaled, and thereby may prevent dryness in the lungs and bronchial tubes. Another advantage of nasal breathing is that the oxygen may also be more optimally absorbed during exhalation. The back pressure created in the lungs with the slower exhalation of nose breathing may allow more time for the lungs to transfer oxygen to the blood. By contrast, exhaling through the mouth may blow the required carbon dioxide out too quickly, thereby resulting in less oxygen being absorbed. A further reason nasal breathing may result in more oxygen being absorbed, is that nitric oxide may be produced in the nasal cavity which may increase the efficiency of oxygen exchange (e.g., by up to 18 percent). By contrast, there is no nitric oxide inhaled through mouth breathing, and this may result in less oxygen being absorbed. Ultimately, when less oxygen is absorbed, there may be a cascade of sleep, stamina, energy level and ADHD problems.

Further, a person that does not breathe through their nose may aggravate snoring or obstructive sleep apnea. Several ailments may affect a person that relies on mouth breathing. With less oxygen being delivered to the brain, muscles and all the cells of the body, the body may function less than optimally. Also, sleep may be disturbed and of poor quality. Chronic mouth breathing may also cause halitosis, gum disease, and may worsen symptoms of other illnesses.

It is typically understood that the oral passageway to the lungs has less resistance than the nasal passageway. Thus, when using a conventional oro-nasal (i.e., full face) mask for treatment of sleep disordered breathing, most of the air inhaled by the patient is through the patient's oral passageway.

As shown in FIG. 7-1, a cushion assembly or plenum chamber 3200 according to the present technology may be constructed to have a dual chamber configuration such that a nasal chamber is separated from an oral chamber so that the two chambers may be pressurized to different levels. The nasal chamber may provide pressurized air to the patient's nasal airways and the oral chamber may provide pressurized air to the patient's mouth. This arrangement may encourage and increase nasal breathing by providing a higher pressure in the nasal chamber than in the oral chamber. As shown in FIG. 9, the pressure gradient generated by the pressure differential in the nasal and oral chambers moves the soft palate 12 anteriorly which tends to occlude the oral passage thus promoting and increasing nasal breathing.

Since the oral chamber has relatively reduced pressure, the cushion assembly as a whole may exert less force against the patient's face as compared to conventional full face masks and thus may require less holding force by the positioning and stabilizing structure to secure the cushion on the patient's face. As a result, comfort may be enhanced. Additionally, minimized headgear may be possible (e.g., a single strap headgear). In other examples, minimized headgear may be used in conjunction with a cushion that uses an adhesive to adhere to the patient's face. In other examples, the adhesive cushion may be used without any headgear. Further, relatively smaller flow generators may be used (e.g., a wearable flow generator).

As shown in FIG. 7-1, the flow of air from the flow generator may be provided only to the nasal chamber. An air passage between the nasal chamber and the oral chamber may be provided to allow the flow of air to be conveyed from the nasal chamber to the oral chamber. The air passage may be formed by a hole or plurality of holes (e.g., 2, 3, 4, 5, 1 to 5, 1 to 10, or 5 or more) in a partition or dividing wall between the chambers and may be constructed to allow a desired level of flow to the oral chamber so that a desired pressure differential is achieved. The holes may be constructed or arranged (e.g., number of holes and placement of the holes) to maintain a pressure in the oral chamber that is at a desired level lower than a pressure in the nasal chamber to promote nasal breathing.

In the illustrated example of FIGS. 13 to 15-4, a partition 3280 may be disposed in the plenum chamber 3200 to form distinct nasal 3234 and oral 3264 chambers. The partition 3280 may have a hole or a plurality of holes (e.g., air passages) formed therein to convey the flow of air from the nasal chamber to the oral chamber. The partition may form a wall arranged such that a first surface of the wall is disposed in the nasal chamber and a second surface of the wall is disposed in the oral chamber.

The partition 3280 may extend across an interior of the cushion assembly from the patient contacting side 3202 to the non-patient contacting side 3204 of the plenum chamber and may be formed as part of the seal-forming structure 3100. In the illustrated example, the partition extends from an inner edge of the seal-forming structure that forms the oral hole 3271, as shown in FIGS. 15-2 and 15-2A. However, in other examples, such as shown in FIGS. 15-2B, the partition 3280 may extend from a portion of the seal-forming structure that is spaced from the inner edge. The partition 3280 connects with the non-patient contacting side 3204 (e.g., shell 3210) of the plenum chamber below the inlet ports 3240 so that the flow of air from the headgear tubes 3340 is delivered to the nasal chamber 3234.

It is noted that the partition 3280 may be formed of silicone or other suitable materials. The partition 3280 may be formed integrally in one piece (e.g., molded together) with the seal-forming structure and/or the plenum chamber 3200 or may be attached thereto (e.g., by gluing or other suitable methods). Additionally, it is noted that a thickness of the partition may vary in different portions of the partition. For example, the portion of the partition 3280 that connects (or is adjacent) to the patient contacting side 3202 of the plenum chamber may have a reduced thickness in order to increase compliance and flexibility of the partition 3280 in this area to enhance patient comfort.

In other examples, instead of holes in the partition, the air passage between the nasal chamber and the oral chamber may be provided by a fixed or adjustable flow regulator (e.g., a valve 10 (FIG. 8)). In other examples, the holes in the partition may be provided in conjunction with an adjustable air passage provided by a flow regulator such that the pressure differential may be further adjusted from a default differential. An adjustable flow regulator may allow the pressure in the oral chamber to be adjusted to an individual patient's needs. For example, a "light mouth breather" may be able to reduce headgear tension, thus enhancing comfort, by adjusting the regulator to decrease pressure in the oral chamber.

In the illustrated example of FIGS. 16 to 19-4, the adjustable flow regulator may be in the form of a regulator valve 3250. The regulator valve 3250 may interface with the partition 3280 such that the size of an air passage (e.g., formed as a connecting passage 3256) between the nasal and oral chambers may be adjusted (see FIGS. 17-2, 17-3 and 19-3). A first opening into the connecting passage 3256 may be disposed in the nasal chamber 3234 and a second opening into the connecting passage may be disposed in the oral chamber 3264. As shown in FIGS. 16 to 17-3, the regulator valve 3250 may comprise an outer housing 3252 that rotatably supports an adjustment mechanism 3253 (e.g., a dial). The dial may be rotated to adjust the size of the connecting passage 3256 from a minimum size, as shown in FIG. 17-2, to a maximum size as shown in FIG. 17-3 to select a desired pressure differential. A portion of the regulator valve (e.g., the outer housing 3252) may be formed integrally with the plenum chamber (e.g., shell 3210) or may be attached thereto. The dial may protrude from the non-patient contacting side 3204 of the plenum chamber for manual adjustment by the patient. It is noted that other adjustable flow regulators, such as the valve 10, or other suitable flow regulators may be used. It is also noted that the partition in FIGS. 18 to 19-4 may also have holes formed therein in addition to the regulator valve 3250.

In examples, the flow regulator may be automatically controlled to adjust the flow of air through the air passage. For example, if resistance in the nasal passages increases beyond a threshold (e.g., because the patient's nasal passages are occluded), the flow regulator may be adjusted to increase the flow of air into the oral chamber to a level sufficient to allow breathing through the patient's mouth. In other examples, the flow regulator may be operative to adjust automatically in responsive to conditions (e.g., pressure and/or flow rate) in the patient interface. This may be through the use of sensors with an electronic valve system, or a mechanical system that responds to changes in pressure or flow rate, for example.

The cushion assembly may include exhaust vents in the nasal chamber and/or the oral chamber. The vents and the pressure differential in the chambers may be tuned so that the cushion assembly provides sufficient $CO_2$ washout from the mask. Additionally, a benefit of the dual chamber cushion assembly is that the relatively lower pressure in the oral chamber makes it easier to exhale through the mouth.

Referring to FIG. 7-2, another example of a plenum chamber 3200 having a dual chamber configuration is shown. The plenum chamber 3200 in FIG. 7-2 is similar to the plenum chamber in FIG. 7-1 except that the flow of air from the flow generator may be provided to both the nasal chamber and the oral chamber (e.g., through separate conduits (e.g., headgear conduits) and/or connections to a supply tube). It is noted that any of the examples described herein made be configured such that the flow of air from the flow generator is provided to both the nasal chamber and the oral chamber as described here and shown in FIG. 7-2. A flow regulator (e.g., valve 10 (FIG. 8) may be disposed to control the flow to the chambers. For example, to reduce pressure in the oral chamber, the flow regulator may be adjusted to restrict flow to the oral chamber to encourage or promote nasal breathing. In other examples, the flow regulator in the air supply path and the flow regulator between the nasal and oral chambers may be adjusted in concert to achieve a desired pressure differential.

Turning to FIG. 10, example pressure ranges for the nasal and oral chambers are shown. For example, the air passage(s) and/or flow regulator(s) may be tuned such that when the flow generator (FG) is set to deliver a pressure of 10 $cmH_2O$, the dual chamber cushion assembly provides a pressure of 10 $cmH_2O$ to nasal chamber and a pressure of about 5 $cmH_2O$ to the oral chamber. At the same tuning, when the flow generator (FG) is set to deliver a pressure of 20 $cmH_2O$, the dual chamber cushion assembly provides a pressure of 20 $cmH_2O$ to the nasal chamber and a pressure of about 10.25 $cmH_2O$ to the oral chamber (other examples at this example tuning are readily apparent from FIG. 10). In other examples, the air passage(s) and/or flow regulator(s) may be tuned differently to provide a smaller or larger pressure differential.

For example, the cushion assembly may be configured to provide a therapeutic pressure in the nasal chamber at a level that is at least 2 $cmH_2O$ above a pressure in the oral chamber to promote nasal breathing. In other examples, the pressure in the nasal chamber may be at least 3 $cmH_2O$, at least 4 $cmH_2O$, at least 5 $cmH_2O$, at least 10 $cmH_2O$, 2-10 $cmH_2O$, 3-8 $cmH_2O$, or 4-7 $cmH_2O$ above the pressure in the oral chamber.

It should also be appreciated that one or more aspects of the present technology may be combinable with one or more aspects of: WO 2019/183680, filed Mar. 28, 2019, which is hereby incorporated herein by reference in its entirety.

For instance, the plenum chamber, seal-forming structure and positioning and stabilizing structure of the present technology may include any of the features of the plenum chamber, seal-forming structure and positioning and stabilizing structure in any of the examples in the '680 application. Additionally, the plenum chamber, seal-forming structure and positioning and stabilizing structure disclosed herein may replace any of the plenum chamber, seal-forming structure and positioning and stabilizing structures in any of the patient interfaces disclosed in the '680 application, and the plenum chamber, seal-forming structure and positioning and stabilizing structure of the present technology may include any of the features of the plenum chamber, seal-forming structure and positioning and stabilizing structure in any of the examples in the '680 application.

5.3.4.1 Nasal Breathing Training

The dual chamber cushion assembly may also be used to train a patient to increase nasal breathing and/or to breathe primarily through the nasal passageways. For example, for a mouth breather, the pressure differential may be gradually increased (e.g., by adjusting the air passage/flow regulator(s)) over the course of treatment to reduce the pressure in the oral chamber thereby promoting nasal breathing. For example, over the course of several weeks or several months, the pressure differential may be gradually increased to train the patient to breathe through the nasal passageways thereby increasing the patient's nasal breathing over the course of the treatment. Eventually, all or nearly all of the flow of air from the flow generator may remain in the nasal chamber for inhalation through the patient's nasal passageways.

In an example, during a first treatment or treatments, the cushion assembly may be tuned to provide a therapeutic pressure in the oral chamber that enables the patient to breathe through the patient's mouth. For example, during the first treatment(s), the oral chamber may be pressurized to the same level as the nasal chamber (or a level less than the nasal chamber but sufficient to allow oral breathing). Then, during subsequent treatments, the cushion assembly may be tuned to gradually decrease the therapeutic pressure in the oral chamber to train the patient to increase nasal breathing and/or to breathe primarily through the patient's nasal passageways.

In an example, during a first treatment, the therapeutic pressure in the oral chamber may be greater than or the same as the therapeutic pressure in the nasal chamber. For example, during the first treatment, the therapeutic pressure in the nasal chamber may be in a range of 6 to 30 $cmH_2O$ above ambient air pressure, and the therapeutic pressure in the oral chamber may be in a range of 6 to 30 $cmH_2O$ above ambient air pressure.

In examples, during the subsequent treatments, the therapeutic pressure in the oral chamber may gradually decrease to a level below 15 cmH$_2$O above ambient air pressure. In other examples, during the subsequent treatments, the therapeutic pressure in the oral chamber may gradually decrease to a level below 10 cmH$_2$O, below 7 cmH$_2$O, or below 5 cmH$_2$O above ambient air pressure.

5.3.4.2 Additional Illustrated Examples of Dual Chamber Cushion Assemblies

The partitions and/or flow regulators (and any other features) discussed in the examples above may be utilized in other patient interfaces such as the example patient interfaces described below.

5.3.4.2.1 Over-the-Nose Full Face Mask

FIGS. 20 to 23 show a patient interface 7000 according to another example of the present technology. The patient interface includes a frame assembly 7100, a cushion assembly 7175 including a seal-forming structure 7200, an air delivery connector (e.g., elbow assembly 7600), and a positioning and stabilising structure (e.g., headgear 7800 including upper side straps 7802, lower side straps 7804, and crown strap 7806). The frame assembly 7100 includes a shroud or wall member 7110, a pair (i.e., right and left) of upper headgear connector arms 7134 extending from respective sides of an upper portion of the shroud 7110, and a pair (i.e., right and left) of lower headgear connector arms 7154 extending from respective sides of a lower portion of the shroud 7110. In the illustrated example, the shroud 7110 (e.g., constructed of a relatively hard plastic material such as polycarbonate) has an opening 7105 formed therein.

The cushion assembly 7175 may connect to the frame assembly 7100 independently of the elbow assembly 7600, and the elbow assembly 7600 may connect to the frame assembly 7100 independently of the cushion assembly 7175.

Each lower headgear strap 7804 may include a headgear clip 7160 configured to connect to a respective lower headgear connector arm 7154 (e.g., with mating magnetic connectors).

In the illustrated example, each lower headgear connector arm 16154 includes a lower headgear connection point in the form of a magnetic connector 16155 structured to locate and connect to a magnet associated with a headgear clip 16160 provided to a respective lower headgear strap 16804 of the headgear. However, it should be appreciated that the upper and lower headgear connector arms 16134, 16154 may be connected with headgear straps of the headgear in other suitable manners.

The cushion assembly 7175 is a full-face cushion assembly configured to deliver pressurized air to the patient's nasal and oral passages. The seal-forming structure 7200 is configured to encircle the patient's nose and mouth and may seal above the patient's pronasale (e.g., along the patient's nasal bridge).

As shown in FIGS. 21-23, the cushion assembly 7175 may include a partition 7280 to form distinct nasal 7234 and oral 7264 chambers. The partition 7280 may include any of the features described above with respect to FIGS. 7-1 to 19-4. For example, the partition 7280 may have a plurality of holes 7282 formed therein, as shown in FIG. 22. Additionally, the cushion assembly 7175 may include flow regulator(s) in accordance with the examples described above.

It should also be appreciated that one or more aspects of the present technology may be combinable with one or more aspects of: US 2018/0250486, filed Mar. 12, 2018, which is hereby incorporated herein by reference in its entirety.

For instance, the frame assembly, elbow assembly and headgear of the present technology may be identical to the frame assembly, elbow assembly and headgear in any of the examples in the '486 application. Additionally, the cushion assembly disclosed herein may replace any of the cushion assemblies in any of the patient interfaces disclosed in the '486 application, and the cushion assembly of the present technology may include any of the features of the cushion assemblies in any of the examples in the '486 application.

5.3.4.2.2 Full Face Mask with Separate Nasal and Oral Cushions

FIGS. 24 to 26 show a patient interface 8000 according to another example of the present technology. The patient interface includes a cushion assembly 8001 having a nares portion 8020 and an oral portion 8040. The nares portion 8020 may at least partially form a nasal chamber 8034 and the oral portion 8040 may at least partially form an oral chamber 8064, as shown in FIG. 25. A supply tube may be connected to a swivel elbow assembly 8002, to direct the pressurized, breathable gas to at least the nares portion 8020 of the cushion assembly. The swivel elbow may include vent holes 8006 and may connect to an anterior non-patient contacting side of the cushion assembly via an aperture 8052, as shown in FIG. 25. However, in other examples, the oral portion 8040 and/or the nares portion 8020 may include vent holes.

The nares portion 8020 may include a nares sealing portion 8022 adapted to form a seal with the patient's nares, a decoupling portion 8025, and headgear connectors 8021 adapted to connect to headgear 8060. In the illustrated example of FIGS. 24 and 25, the nares sealing portion 8022 may comprise a pair of nasal pillows. The decoupling portion 8025 (e.g., a thin walled section) may function to decouple forces applied to the nares portion 8020 from the nares sealing portion 8022.

The oral portion 8040 may include an oral sealing portion 8042 adapted to seal around the patient's mouth, a decoupling portion 8045 to decouple forces applied to the oral portion 8040 from the oral sealing portion, and lower headgear connectors 8041 adapted to connect to the headgear 8060.

The headgear 8060 may include straps adapted to secure the cushion assembly 8001 on the patient's face. The straps may include a side headgear strap 8061, a lower headgear strap 8063, a rear headgear portion 8065 and a crown headgear portion 8066. The side headgear straps 8061 may include side headgear connectors 8062 for connection with the headgear connectors 8021 of the nares portion 8020.

Referring to the example shown in FIG. 26, the nares portion 8020 includes a nares sealing portion 8594 arranged to seal with the patient's nares. In contrast to the nasal pillows arrangement of FIGS. 24 and 25, the nares sealing portion 8594 may seal against an underside of the patient's nose or, as illustrated, may seal above the patient's pronasale but below the nasal bridge. A frame 8589 may be connected to the nares portion 8020 and/or the oral portion 8040 and may comprise a rigid structure or a flexible structure (e.g., silicone).

As shown in FIGS. 24-26, the cushion assembly 8001 may include a partition 8082 to form distinct nasal 8034 and oral 8064 chambers. The partition 8082 may include any of the features described above with respect to FIGS. 7-1 to 19-4. For example, the partition 8082 may have a plurality of holes 8586 (FIG. 26) formed therein. Additionally, the cushion assembly 8001 may include flow regulator(s) in accordance with the examples described above.

It should also be appreciated that one or more aspects of the present technology may be combinable with one or more aspects of: U.S. Pat. No. 9,737,678, filed Mar. 28, 2013, which is hereby incorporated herein by reference in its entirety.

For instance, the nares cushion, oral cushion (i.e., mouth cushion) and positioning and stabilizing structure (headgear) of the present technology may include any of the features of the nasal cushion, oral cushion (i.e., mouth cushion) and headgear in any of the examples in the '678 application. Additionally, the nares cushion, oral cushion and headgear disclosed herein may replace any of the nares cushions, oral (mouth) cushions and headgear in any of the patient interfaces disclosed in the '678 application, and the nares cushion, oral cushion and headgear of the present technology may include any of the features of the nares cushion, oral cushion and headgear in any of the examples in the '678 application.

5.3.4.2.3 Modular Mask with Connectable Nasal and Oral Cushions

FIGS. 27-31 show a patient interface 6000 providing a modular configuration in accordance with one aspect of the present technology. The patient interface 6000 may be convertible between a nasal (e.g., "under the nose") seal mask and an oro-nasal mask, depending on whether a nasal cushion 6050 and/or an oral cushion 6060 is/are coupled to a headgear section. That is, a cushion assembly 6020 may comprise a nasal cushion 6050 and an oral cushion 6060. The nasal cushion 6050 may comprise a nasal seal-forming structure 6052 constructed and arranged to form a seal with a region of a patient's face surrounding the entrance to a patient's nares. The seal-forming structure 6052 may be connected to a rigid or flexible (e.g., silicone) frame. An oral cushion 6060 may comprise an oral seal-forming structure 6062 constructed and arranged to form a seal with a region of a patient's face surrounding the entrance to a patient's mouth. A vent insert 3400 may be provided in the oral cushion, as shown FIG. 30. The nasal cushion may also include a suitable vent structure. Examples of the present technology provide for independent sealing of the nose and mouth.

The seal-forming structure 6052 may comprise a nasal cradle cushion and provide a flow of gas to the patient's nares by sealing against at least the underside of the patient's nose. The exemplary seal-forming structures 6052 will engage the patient's face below the bridge of the nose and some examples, depending on the size and shape of the patient's nose, may engage the patient's nose below the pronasale.

The interchangeability of the nasal cushion 6050 and the oral cushion 6060 allows a nose-breathing patient to undergo therapy with only the nasal cushion 6050 attached. Additionally, the oral cushion 6060 may be used with the nasal cushion 6050 for mouth breathing patients or while training patients to breathe through the nose. In addition, examples of the present technology allow for movement of both the oral seal-forming structure 6062 and the nasal seal-forming structure 3052 independent from one another to provide a comfortable fit and effective seal.

A positioning and stabilizing structure 6300 may include a pair of headgear tubes 6010 to deliver a flow of breathable gas from connection port 3600 to the nasal cushion 6050. The headgear tubes 6010 may be configured to extend along respective sides of the patient's face between the eye and ear and may include an expandable concertina section 6362 (e.g., including one or more folding portions, pleats, corrugations or bellows to form a flexible and length extendable portion of the headgear conduits). Each headgear tube 6010 may include a cushion interface 6012 for connection to a respective side of the nasal cushion 6050. A swivel elbow assembly 3610 may connect the headgear tubes 6010 to the connection port 3600.

In the example of FIG. 27, a lower strap 6326 may be adapted to pass under the patient's ears and include a pair of ends attachable to the oral cushion 6060. Each end of the lower strap 6326 may include a connector 6328 (e.g., including a magnet and/or a clip) configured to removable engage a corresponding lower headgear connector 6066 on the oral cushion 6060.

The oral cushion 6060 and the nasal cushion 6050 may be releasably connected to one another via a joint 6068. The joint 3068 may be removably coupled to the nasal cushion 6050 and the oral cushion 6060 via openings in the nasal cushion and oral cushion, or may be permanently connected to the oral cushion. The joint 6068 may have a hollow interior to fluidly connect the nasal cushion 6050 and the oral cushion 6060. The joint 6068 may include a flexible structure (e.g., silicone material and/or bellows structure) to allow for independent adjustment of the nasal cushion 6050 and the oral cushion 6060 position.

Thus, the flow of breathable gas may be provided from the headgear tubes 6010 to the nasal cushion 6050 and from the nasal cushion 6050 to the oral cushion 6060 via the joint 6068.

A partition may be provided in the cushion assembly 6020 to form a nasal chamber 6034 and an oral chamber 6064 such that the nasal chamber may be pressurized differently than the oral chamber. The partition may be provided at any suitable location in the nasal cushion 6050, the oral cushion 6060 or the joint 6068 provided the flow of air from the headgear tubes is provided directly to the nasal chamber 6034. The partition may include any of the features described above with respect to FIGS. 7-1 to 19-4. For example, the partition may have a plurality of holes formed therein. Additionally, the cushion assembly 6020 may include flow regulator(s) in accordance with the examples described above. In the illustrated example of FIG. 29, the partition 6280 is provided in the joint 6068 and includes a plurality of holes 6282 formed therein.

In another example, the nasal cushion 6050 may comprise a pair of nasal puffs, or nasal pillows, each nasal puff or nasal pillow being constructed and arranged to form a seal with a respective naris of the nose of a patient. In an example shown in FIGS. 30 and 31, the nasal cushion 6050 has a nasal seal-forming structure provided by a pair of nasal pillows 6165. Nasal pillows 3165 in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the nasal cushion 3050 and/or the oral cushion 3060 include a textile sealing surface mounted on a silicone body.

It should also be appreciated that one or more aspects of the present technology may be combinable with one or more aspects of: U.S. Provisional Application No. 62/928,213, filed Oct. 30, 2019, which is hereby incorporated herein by reference in its entirety.

For instance, the nasal cushion, oral cushion (i.e., mouth cushion) and positioning and stabilizing structure of the present technology may include any of the features of the nasal cushion, oral cushion (i.e., mouth cushion) and positioning and stabilizing structure in any of the examples in the '213 application. Additionally, the nasal cushion, oral cushion and joint disclosed herein may replace any of the nasal cushions, oral (mouth) cushions and joints in any of the patient interfaces disclosed in the '213 application, and the nasal cushion, oral cushion and joint of the present technology may include any of the features of the nasal cushion, oral cushion and joint in any of the examples in the '213 application.

5.3.5 Vent

In one form, the patient interface includes a vent constructed and arranged to allow for the washout of exhaled gases, e.g. carbon dioxide.

In certain forms the vent 3400 is configured to allow a continuous vent flow from an interior of the plenum chamber to ambient whilst the pressure within the plenum chamber is positive with respect to ambient. The vent is configured such that the vent flow rate has a magnitude sufficient to reduce rebreathing of exhaled $CO_2$ by the patient while maintaining the therapeutic pressure in the plenum chamber in use.

In one example, the patient interface comprises at least one vent 3400 in the nasal cushion 6050 (e.g., in the plenum chamber), the oral cushion 6060, and/or the joint 6068.

One form of vent in accordance with the present technology comprises a plurality of holes, for example, about 20 to about 80 holes, or about 40 to about 60 holes, or about 45 to about 55 holes.

The vent may be located in the plenum chamber. Alternatively, the vent is located in a decoupling structure, e.g., a swivel.

5.3.6 Decoupling Structure(s)

In one form the patient interface includes at least one decoupling structure, for example, a swivel or a ball and socket.

5.3.7 Connection Port

Connection port (e.g., connection port 3600) allows for connection to the air circuit 4170.

5.3.8 Forehead Support

In one form, the patient interface 3000 includes a forehead support 3700.

5.3.9 Anti-Asphyxia Valve

In one form, the patient interface includes an anti-asphyxia valve.

5.3.10 Ports

In one form of the present technology, a patient interface includes one or more ports that allow access to the volume within the cushion assembly or plenum chamber. In one form this allows a clinician to supply supplementary oxygen. In one form, this allows for the direct measurement of a property of gases within the cushion assembly or plenum chamber, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10 cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

5.4.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or 3800.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 and representing a pressure is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 which may be implemented with processor-control instructions, expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally, or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs, such as with processor control instructions to be executed by one or more processor(s), stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the vent flow rate $Q$ v, the respiratory flow rate $Q$ r, and the leak flow rate $Q$ l.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

5.4.3.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate $Q$ d). The device flow rate $Q$ d, absent any supplementary gas 4180, may be used as the total flow rate $Q$ t. The interface pressure algorithm 4312 estimates the pressure drop ΔP through the air circuit 4170. The dependence of the pressure drop ΔP on the total flow rate $Q$ t may be modelled for the particular air circuit 4170 by a pressure drop characteristic ΔP ($Q$). The interface pressure estimation algorithm, 4312 then provides as an output an estimated pressure, Pm, in the patient interface 3000 or 3800. The pressure, Pm, in the patient interface 3000 or 3800 may be estimated as the device pressure Pd minus the air circuit pressure drop ΔP.

5.4.3.1.2 Vent Flow Rate Estimation

In one form of the present technology, a vent flow rate estimation algorithm 4314 receives as an input an estimated pressure, Pm, in the patient interface 3000 or 3800 from the interface pressure estimation algorithm 4312 and estimates a vent flow rate of air, $Q$ v, from a vent 3400 in a patient interface 3000 or 3800. The dependence of the vent flow rate $Q$ v on the interface pressure Pm for the particular vent 3400 in use may be modelled by a vent characteristic $Q$ v(Pm).

5.4.3.1.3 Leak Flow Rate Estimation

In one form of the present technology, a leak flow rate estimation algorithm 4316 receives as an input a total flow rate, $Q$ t, and a vent flow rate $Q$ v, and provides as an output an estimate of the leak flow rate $Q$ l. In one form, the leak flow rate estimation algorithm estimates the leak flow rate $Q$ l by calculating an average of the difference between total flow rate $Q$ t and vent flow rate $Q$ v over a period sufficiently long to include several breathing cycles, e.g. about 10 seconds.

In one form, the leak flow rate estimation algorithm 4316 receives as an input a total flow rate $Q$ t, a vent flow rate $Q$ v, and an estimated pressure, Pm, in the patient interface 3000 or 3800, and provides as an output a leak flow rate $Q$ l, by calculating a leak conductance, and determining a leak flow rate $Q$ l to be a function of leak conductance and pressure, Pm. Leak conductance is calculated as the quotient of low pass filtered non-vent flow rate equal to the difference between total flow rate $Q$ t and vent flow rate $Q$ v, and low pass filtered square root of pressure Pm, where the low pass filter time constant has a value sufficiently long to include several breathing cycles, e.g. about 10 seconds. The leak flow rate $Q$ l may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, $Q$ t, a vent flow rate, $Q$ v, and a leak flow rate, $Q$ l, and estimates a respiratory flow rate of air, $Q$ r, to the patient, by subtracting the vent flow rate $Q$ v and the leak flow rate $Q$ l from the total flow rate $Q$ t.

5.4.3.2 Therapy Engine Module

In one form of the present technology, a therapy engine module 4320 receives as inputs one or more of a pressure, Pm, in a patient interface 3000 or 3800, and a respiratory flow rate of air to a patient, $Q$ r, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, $Q$ r, and provides as an output a phase Φ of a current breathing cycle of a patient 1000.

In some forms, known as discrete phase determination, the phase output □ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate $Q$ r has a value that exceeds a positive threshold, and a discrete value of 0.5 revolutions (thereby "cycling" the RPT device 4000) when a respiratory flow rate $Q$ r has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate $Q$ r. A continuous value of phase determined in this implementation is often referred to as "fuzzy phase". In one implementation of a fuzzy phase determination algorithm 4321, the following rules are applied to the respiratory flow rate $Q$ r:

1. If $Q$ r is zero and increasing fast then Φ is 0 revolutions.

2. If $Q$ r is large positive and steady then Φ is 0.25 revolutions.

3. If $Q$ r is zero and falling fast, then Φ is 0.5 revolutions.

4. If $Q$ r is large negative and steady then Φ is 0.75 revolutions.

5. If $Q$ r is zero and steady and the 5-second low-pass filtered absolute value of $Q$ r is large then Φ is 0.9 revolutions.

6. If $Q$ r is positive and the phase is expiratory, then Φ is 0 revolutions.

7. If $Q$ r is negative and the phase is inspiratory, then Φ is 0.5 revolutions.

8. If the 5-second low-pass filtered absolute value of $Q$ r is large, Φ is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase Φ is first discretely estimated from the respiratory flow rate $Q$ r as described above, as are the inhalation time Ti and the exhalation time Te. The continuous phase Φ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template Π(Φ).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\prod(\Phi, t) = \begin{cases} \prod_i(t), & \Phi = 0 \\ \prod_e(t - T_i), & \Phi = 0.5 \end{cases}$$

where Πi(t) and Πe(t) are inspiratory and expiratory portions of the waveform template Π(Φ, t). In one such form, the inspiratory portion Πi(t) of the waveform template is a smooth rise from 0 to 1 parametrised by a rise time, and the expiratory portion Πe(t) of the waveform template is a smooth fall from 1 to 0 parametrised by a fall time.

5.4.3.2.3 Ventilation Determination

In one form of the present technology, a ventilation determination algorithm 4323 receives an input a respiratory flow rate $Q$ r, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, $Q$ r, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate $Q$ peak over the inspiratory portion of the cycle. This and many other procedures involving sampling the respiratory flow rate $Q$ r produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where $0<K<1$. There is an arbitrarily large number of measures that are exactly proportional to ventilation if the flow rate shape is constant.

5.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal $Q$ r and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty-five scaled data points are generated by the central controller 4230, and represent a moving average of the preceding several inspiratory events, e.g., three events. The moving average of continuously updated values of the (e.g., sixty-five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty-two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal $Q$ r and provides as an output a flag that indicates that an apnea or a hypopnea has been detected.

In one form, an apnea will be said to have been detected when a function of respiratory flow rate $Q$ r falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate $Q$ r falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal $Q$ r and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal $Q$ r to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal $Q$ r, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal $Q$ r, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \tag{1}$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure P0 may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 or 3800 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)

Transducer fault detection

Failure to detect the presence of a component

Operating parameters outside recommended ranges (e.g. pressure, flow rate, temperature, $PaO_2$)

Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm

Sending a message to an external device

Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000 or 3800.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate $Q$ peak 0.4 L/s, exhalation time Te 2.4 s, peak expiratory flow rate $Q$ peak –0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Respiratory Therapy Modes

Various respiratory therapy modes may be implemented by the disclosed respiratory therapy system.

5.8.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure P0 throughout the respiratory cycle. Such implementations are generally grouped under the heading of CPAP therapy. In such implementations, there is no need for the therapy engine module 4320 to determine phase Φ or the waveform template Π(Φ).

In CPAP therapy, the base pressure P0 may be a constant value that is hard-coded or manually entered to the RPT device 4000. Alternatively, the central controller 4230 may repeatedly compute the base pressure P0 as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

FIG. 4E is a flow chart illustrating a method 4500 carried out by the central controller 4230 to continuously compute the base pressure P0 as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure P0 by a predetermined pressure increment ΔP, provided the resulting treatment pressure Pt would not exceed a maximum treatment pressure Pmax. In one implementation, the predetermined pressure increment ΔP and maximum treatment pressure Pmax are 1 cmH2O and 25 cmH2O respectively. In other implementations, the pressure increment ΔP can be as low as 0.1 cmH2O and as high as 3 cmH2O, or as low as 0.5 cmH2O and as high as 2 cmH2O. In other implementations, the maximum treatment pressure Pmax can be as low as 15 cmH2O and as high as 35 cmH2O, or as low as 20 cmH2O and as high as 30 cmH2O. The method 4500 then returns to step 4520.

At step 4560, the central controller 4230 decreases the base pressure P0 by a decrement, provided the decreased base pressure P0 would not fall below a minimum treatment pressure Pmin. The method 4500 then returns to step 4520. In one implementation, the decrement is proportional to the value of P0–Pmin, so that the decrease in P0 to the minimum treatment pressure Pmin in the absence of any detected events is exponential. In one implementation, the constant of proportionality is set such that the time constant τ of the exponential decrease of P0 is 60 minutes, and the minimum treatment pressure Pmin is 4 cmH2O. In other implementations, the time constant τ could be as low as 1 minute and as high as 300 minutes, or as low as 5 minutes and as high as 180 minutes. In other implementations, the minimum treatment pressure Pmin can be as low as 0 cmH2O and as high as 8 cmH2O, or as low as 2 cmH2O and as high as 6 cmH2O. Alternatively, the decrement in P0 could be predetermined, so the decrease in P0 to the minimum treatment pressure Pmin in the absence of any detected events is linear.

5.8.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm 4329 increases the treatment pressure Pt to P0+A (known as the IPAP) at the start of, or during, or inspiration and decreases the treatment pressure Pt to the base pressure P0 (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH2O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure P0 in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure P0 plus the pressure support A, and the EPAP is the base pressure P0.

In some forms of pressure support ventilation therapy, known as fixed pressure support ventilation therapy, the pressure support A is fixed at a predetermined value, e.g. 10 cmH2O. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = Gf(\text{Vent} - Vtgt)dt \qquad (2)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH2O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations. In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure P0. As with the base pressure P0 in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure P0 in constant CPAP therapy.

Alternatively, the therapy parameter determination algorithm 4329 may repeatedly compute the base pressure P0 during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.8.3 High Flow Therapy

In other forms of respiratory therapy, the pressure of the flow of air is not controlled as it is for respiratory pressure therapy. Rather, the central controller 4230 controls the pressure generator 4140 to deliver a flow of air whose device flow rate $Q$ d is controlled to a treatment or target flow rate $Q$ tgt that is typically positive throughout the patient's breathing cycle. Such forms are generally grouped under the heading of flow therapy. In flow therapy, the treatment flow rate $Q$ tgt may be a constant value that is hard-coded or manually entered to the RPT device 4000. If the treatment flow rate $Q$ tgt is sufficient to exceed the patient's peak inspiratory flow rate, the therapy is generally referred to as high flow therapy (HFT). Alternatively, the treatment flow rate may be a profile $Q$ tgt(t) that varies over the respiratory cycle.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol $Q$. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, $Q$ d, is the flow rate of air leaving the RPT device. Total flow rate, $Q$ t, is the flow rate of air and any supplementary gas reaching the patient interface via the air circuit. Vent flow rate, $Q$ v, is the flow rate of air leaving a vent to allow washout of exhaled gases. Leak flow rate, $Q$ l, is the flow rate of leak from a patient interface system or elsewhere. Respiratory flow rate, $Q$ r, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g$-$f$/$cm^2$ and hectopascal. 1 $cmH_2O$ is equal to 1 $g$-$f$/$cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(ii) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate ($Q$ peak): The maximum value of flow rate during the inspiratory portion of the respiratory flow waveform.

Respiratory flow rate, patient airflow rate, respiratory airflow rate ($Q$ r): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP–EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

5.9.4 Anatomy 5.9.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion.

Anatomy of the Skull

Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.9.4.2 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.9.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.9.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.9.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.9.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g.

a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.9.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.10 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

-continued

| 5.11 REFERENCE SIGNS LIST | |
|---|---|
| patient contacting side | 3202 |
| non-patient contacting side | 3204 |
| shell | 3210 |
| nasal portion | 3230 |
| nasal chamber | 3234 |
| inlet port | 3240 |
| regulator valve | 3250 |
| outer housing | 3252 |
| adjustment mechanism (e.g., turn dial) | 3253 |
| connecting passage | 3256 |
| oral portion | 3260 |
| oral chamber | 3264 |
| anti-Asphyxia valve (AAV) | 3270 |
| oral hole | 3271 |
| nasal holes | 3272 |
| oronasal transition | 3275 |
| partition | 3280 |
| partition | 3280A |
| holes | 3282 |
| positioning and stabilising structure | 3300 |
| upper strap | 3310 |
| lower strap | 3320 |
| lower connection point | 3325 |
| lower strap clip | 3326 |
| headgear tube | 3340 |
| tab | 3342 |
| headgear tube connector | 3344 |
| conduit headgear inlet | 3390 |
| vent | 3400 |
| connection port | 3600 |
| swivel elbow assembly | 3610 |
| forehead support | 3700 |
| concertina section | 3904 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| heated air circuit | 4171 |
| supplemental oxygen | 4180 |
| electrical components | 4200 |
| Printed Circuit Board Assembly (PCBA) | 4202 |
| electrical power supply | 4210 |
| input devices | 4220 |
| transducers | 4270 |
| output devices | 4290 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| heating element | 5240 |
| humidifier controller | 5250 |
| central humidifier controller | 5251 |
| heating element controller | 5252 |

| 5.11 REFERENCE SIGNS LIST | |
|---|---|
| valve | 10 |
| soft palate | 12 |
| patient | 1000 |
| bed partner | 1100 |
| patient interface | 3000 |
| seal-forming structure | 3100 |
| plenum chamber | 3200 |
| plenum chamber | 3200A |

-continued

5.11 REFERENCE SIGNS LIST

| | |
|---|---|
| air circuit controller | 5254 |
| patient interface | 6000 |
| headgear tube | 6010 |
| cushion interface | 6012 |
| cushion assembly | 6020 |
| nasal chamber | 6034 |
| nasal cushion | 6050 |
| nasal seal-forming structure | 6052 |
| oral cushion | 6060 |
| oral seal-forming structure | 6062 |
| oral chamber | 6064 |
| lower headgear connectors | 6066 |
| joint | 6068 |
| nasal pillows | 6165 |
| partition | 6280 |
| holes | 6282 |
| positioning and stabilizing structure | 6300 |
| nasal headgear strap | 6310 |
| lower strap | 6326 |
| connector | 6328 |
| concertina section | 6362 |
| patient interface | 7000 |
| frame assembly | 7100 |
| opening | 7105 |
| shroud | 7110 |
| upper headgear connector arms | 7134 |
| lower headgear connector arms | 7154 |
| cushion assembly | 7175 |
| headgear clip | 7160 |
| seal-forming structure | 7200 |
| nasal chamber | 7234 |
| oral chamber | 7264 |
| partition | 7280 |
| holes | 7282 |
| elbow assembly | 7600 |
| headgear | 7800 |
| upper headgear strap | 7802 |
| lower headgear strap | 7804 |
| crown strap | 7806 |
| patient interface | 8000 |
| cushion assembly or mask system | 8001 |
| elbow | 8002 |
| vent holes | 8006 |
| nares portion | 8020 |
| headgear connectors | 8021 |
| nares sealing portion | 8022 |
| decoupling portion | 8025 |
| nasal chamber | 8034 |
| oral or mouth portion | 8040 |
| lower headgear connectors | 8041 |
| oral sealing portion | 8042 |
| decoupling portion | 8045 |
| aperture | 8052 |
| headgear | 8060 |
| side headgear straps | 8061 |
| side headgear connectors | 8062 |
| lower headgear strap | 8063 |
| oral chamber | 8064 |
| rear portion | 8065 |
| crown strap portion | 8066 |
| partition | 8082 |
| holes | 8586 |
| frame | 8589 |
| nares sealing portion | 8594 |

The invention claimed is:

1. A patient interface for sealed delivery of a flow of air at a continuously positive pressure with respect to ambient air pressure to an entrance to a patient's airways including at least an entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing, the patient interface comprising:

a cushion assembly configured to deliver a flow of air to the patient's airways, the cushion assembly including:

a nasal chamber pressurisable to a therapeutic pressure of at least 6 cmH$_2$O above ambient air pressure, the nasal chamber configured to, in use, deliver the flow of air to the patient's nasal passageways;

an oral chamber pressurisable to a different level than the nasal chamber, the oral chamber configured to, in use, deliver the flow of air to the patient's mouth;

at least one inlet port sized and structured to receive the flow of air into at least the nasal chamber;

a seal-forming structure constructed and arranged to form a seal with a region of the patient's face surrounding an entrance to the patient's airways, said seal-forming structure having at least one hole formed therein such that the flow of air is delivered to at least an entrance to the patient's nares; and a partition forming a wall extending between and separating the nasal chamber and the oral chamber, wherein a first surface of the wall is disposed in the nasal chamber and a second surface of the wall that is opposite the first surface is disposed in the oral chamber, wherein a plurality of holes is formed in the wall extending through the first surface and the second surface to, in use, allow the flow of air to flow from the nasal chamber to the oral chamber in a manner that maintains a pressure in the oral chamber at a level lower than a pressure in the nasal chamber to promote nasal breathing.

2. The patient interface of claim 1, wherein the plurality of holes comprises at least three holes.

3. The patient interface of claim 1, wherein the pressure in the nasal chamber is at least 2 cmH$_2$O above the pressure in the oral chamber.

4. The patient interface of claim 1, wherein the pressure in the nasal chamber is at least 5 cmH$_2$O above the pressure in the oral chamber.

5. The patient interface of claim 1, said cushion assembly further comprising a flow regulator including a passageway fluidly connecting the nasal chamber and the oral chamber to allow the flow of air to flow from the nasal chamber to the oral chamber, wherein the flow regulator is configured to adjust a size of the passageway to control a volume of the flow of air that flows from the nasal chamber to the oral chamber.

6. The patient interface of claim 5, wherein the flow regulator is an adjustable valve.

7. The patient interface of claim 5, wherein the size of the passageway is manually adjustable.

8. The patient interface of claim 7, wherein the flow regulator further comprises a rotatable dial to manually adjust the size of the passageway.

9. The patient interface of claim 5, wherein the size of the passageway is automatically adjustable.

10. The patient interface of claim 5, further comprising a sensor to determine a level of resistance in the patient's nasal passageways, wherein, in use, when the level of resistance in the patient's nasal passageways exceeds a first threshold, the flow regulator is configured to automatically adjust the flow of air to increase pressure in the oral chamber.

11. The patient interface of claim 1, wherein the partition comprises silicone.

12. The patient interface of claim 1, wherein the seal-forming structure includes a nasal seal comprising the at least one hole such that the flow of air is delivered to at least an entrance to the patient's nares.

13. The patient interface of claim 1, wherein the seal-forming structure includes an oral seal having a hole formed therein to deliver the flow of air to the patient's mouth.

14. The patient interface of claim 1, wherein the cushion assembly is an oro-nasal cushion assembly and the seal-forming structure is configured to, in use, form a seal below the patient's pronasale.

15. The patient interface of claim 14, further comprising a pair of headgear tubes configured to deliver the flow of air to the cushion assembly, the pair of headgear tubes being configured to, in use, extend along respective sides of the patient's face between the patient's eye and ear.

16. The patient interface of claim 1, wherein the cushion assembly is a full-face cushion assembly and the seal-forming structure is configured to, in use, form a seal above the patient's pronasale.

17. The patient interface of claim 16, wherein the seal-forming structure is configured to, in use, form a seal along the patient's nasal bridge.

18. The patient interface of claim 1, wherein the wall extends from a first interior surface of the cushion assembly on a patient-contacting side of the cushion assembly to a second interior surface of the cushion assembly on a non-patient contacting side of the cushion assembly, and wherein the wall is non-removably attached to the first interior surface of the cushion assembly, and the wall is non-removably attached to the second interior surface of the cushion assembly.

19. The patient interface of claim 1, wherein the wall forms an upper surface of the mouth chamber and a lower surface of the nasal chamber.

20. The patient interface of claim 1, wherein the cushion assembly further comprises a nasal cushion and a separate oral cushion, wherein the seal-forming structure includes a nasal seal comprising the at least one hole such that the flow of air is delivered to at least an entrance to the patient's nares, the nasal cushion comprising the nasal seal, wherein the seal-forming structure includes an oral seal having a hole formed therein to deliver the flow of air to the patient's mouth, the oral cushion comprising the oral seal.

21. The patient interface of claim 20, wherein the wall is disposed in the nasal cushion, in the oral cushion, or in a fluidly connecting structure therebetween.

22. The patient interface of claim 20, further comprising a joint forming a hollow interior to fluidly connect the nasal cushion and the oral cushion, wherein the wall is disposed in the hollow interior of the joint.

23. The patient interface of claim 1, wherein the cushion assembly is configured such that, in use, the nasal chamber is pressurized in a range of 8 to 14 $cmH_2O$ above ambient air pressure while the oral chamber is pressurized in a range of 4 to 7.5 $cmH_2O$ above ambient air pressure.

24. The patient interface of claim 1, wherein the cushion assembly is configured such that, in use, the nasal chamber is pressurized in a range of 14 to 20 $cmH_2O$ above ambient air pressure while the oral chamber is pressurized in a range of 7.5 to 10.5 $cmH_2O$ above ambient air pressure.

25. The patient interface of claim 1, further comprising a positioning and stabilizing structure to provide a force to hold the seal-forming structure in a therapeutically effective position on the patient's head, the positioning and stabilising structure being constructed and arranged so that at least a portion overlies a region of the patient's head superior to an otobasion superior of the patient's head in use.

26. The patient interface of claim 1, wherein, in use, the first surface of the wall is configured to impede passage of the flow of air from the nasal chamber to the oral chamber, only allowing the flow of air to pass through the plurality of holes formed in the wall.

* * * * *